US011690560B2

(12) United States Patent
Bower et al.

(10) Patent No.: US 11,690,560 B2
(45) Date of Patent: Jul. 4, 2023

(54) COGNITIVE PLATFORM CONFIGURED AS A BIOMARKER OR OTHER TYPE OF MARKER

(71) Applicant: Akili Interactive Labs, Inc., Boston, MA (US)

(72) Inventors: Jeffrey Bower, Norwood, MA (US); Titiimaea Alailima, Cambridge, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 856 days.

(21) Appl. No.: 16/344,074

(22) PCT Filed: Oct. 24, 2017

(86) PCT No.: PCT/US2017/058103
§ 371 (c)(1),
(2) Date: Apr. 23, 2019

(87) PCT Pub. No.: WO2018/081134
PCT Pub. Date: May 3, 2018

(65) Prior Publication Data
US 2020/0060603 A1 Feb. 27, 2020

Related U.S. Application Data

(60) Provisional application No. 62/412,215, filed on Oct. 24, 2016.

(51) Int. Cl.
*A61B 5/00* (2006.01)
*G16H 50/50* (2018.01)
(Continued)

(52) U.S. Cl.
CPC .......... *A61B 5/4088* (2013.01); *A61B 5/0024* (2013.01); *A61B 5/0075* (2013.01);
(Continued)

(58) Field of Classification Search
CPC ....... A61B 5/4088; A61B 5/246; A61B 5/377; A61B 5/0024; A61B 5/0075;
(Continued)

(56) References Cited

U.S. PATENT DOCUMENTS

2004/0175683 A1  9/2004  Duffy et al.
2008/0280276 A1  11/2008  Raber et al.
(Continued)

FOREIGN PATENT DOCUMENTS

JP  2005-137629 A  6/2005
JP  2011-083403 A  4/2011
(Continued)

OTHER PUBLICATIONS

International Search Report, International application No. PCT/US2017/058103, dated Dec. 28, 2017. ISA/US, Alexandria, VA.
(Continued)

*Primary Examiner* — Daniel L Cerioni
(74) *Attorney, Agent, or Firm* — Gregory Finch; Finch Paolino, LLC

(57) ABSTRACT

Example systems, methods, and apparatus are provided for using data collected from the responses of an individual with the computerized tasks of a cognitive platform to derive performance metrics as an indicator of cognitive abilities, and applying predictive models to generate an indication of neurodegenerative condition. The example systems, methods, and apparatus also can be configured to adapt the computerized tasks to enhance the individual's cognitive abilities, and for using data collected from the responses of an individual with the adapted computerized tasks to derive performance metrics and applying predictive models to generate the indication of neurodegenerative condition.

9 Claims, 22 Drawing Sheets

(51) Int. Cl.
  *G16H 50/30* (2018.01)
  *G16H 50/70* (2018.01)
  *G16H 50/20* (2018.01)
  *G16H 40/63* (2018.01)
  *G16H 20/70* (2018.01)
  *A61B 5/0533* (2021.01)
  *A61B 5/16* (2006.01)
  *G09B 5/06* (2006.01)
  *G09B 7/02* (2006.01)
  *A61B 5/246* (2021.01)
  *A61B 5/377* (2021.01)

(52) U.S. Cl.
  CPC ............ *A61B 5/0533* (2013.01); *A61B 5/165* (2013.01); *A61B 5/167* (2013.01); *A61B 5/246* (2021.01); *A61B 5/377* (2021.01); *A61B 5/4082* (2013.01); *A61B 5/6868* (2013.01); *A61B 5/7267* (2013.01); *A61B 5/7275* (2013.01); *A61B 5/7475* (2013.01); *G09B 5/065* (2013.01); *G09B 7/02* (2013.01); *G16H 20/70* (2018.01); *G16H 40/63* (2018.01); *G16H 50/20* (2018.01); *G16H 50/30* (2018.01); *G16H 50/50* (2018.01); *G16H 50/70* (2018.01)

(58) Field of Classification Search
  CPC ....... A61B 5/0533; A61B 5/165; A61B 5/167; A61B 5/4082; A61B 5/6868; A61B 5/7267; A61B 5/7275; A61B 5/7475; A61B 5/7264; G16H 50/50; G16H 50/30; G16H 50/70; G16H 50/20; G16H 40/63; G16H 20/70; G09B 5/065; G09B 7/02
  USPC ........................................................ 600/544
  See application file for complete search history.

(56) References Cited

U.S. PATENT DOCUMENTS

| | | |
|---|---|---|
| 2012/0108909 A1 | 5/2012 | Slobounov et al. |
| 2012/0190968 A1 | 7/2012 | Raber |
| 2014/0276130 A1 | 9/2014 | Mirelman et al. |
| 2014/0315169 A1 | 10/2014 | Bohbot |
| 2014/0370479 A1* | 12/2014 | Gazzaley ................. G09B 5/02 434/322 |
| 2016/0078780 A1 | 3/2016 | Alexander et al. |
| 2016/0125748 A1 | 5/2016 | Ashford |
| 2016/0262680 A1* | 9/2016 | Martucci .............. A61B 5/4833 |
| 2018/0284138 A1 | 10/2018 | Yang |
| 2018/0284141 A1 | 10/2018 | Ayton et al. |

FOREIGN PATENT DOCUMENTS

| | | |
|---|---|---|
| JP | 2016-179193 A | 10/2016 |
| JP | 2018-512202 A | 5/2018 |
| WO | 2015066037 A1 | 5/2015 |
| WO | 2015179522 A1 | 11/2015 |
| WO | 2016118811 A2 | 7/2016 |

OTHER PUBLICATIONS

Written Opinion of the International Searching Authority, International application No. PCT/US2017/058103, dated Dec. 28, 2017. ISA/US, Alexandria, VA.
Extended European Search Report, European application No. 17865415, dated Mar. 25, 2020 European Patent Office, Munich, DE.
Office Action, European application No. 17865415.8, dated Aug. 30, 2022. European Patent Office, Rijswijk, NL.
Examination Report, Australian application No. 2017347975, dated Jul. 29, 2022. IP Australia, Woden, AU.
Examination Report, Australian application No. 2017347975, dated Aug. 18, 2022. IP Australia, Woden, AU.

* cited by examiner

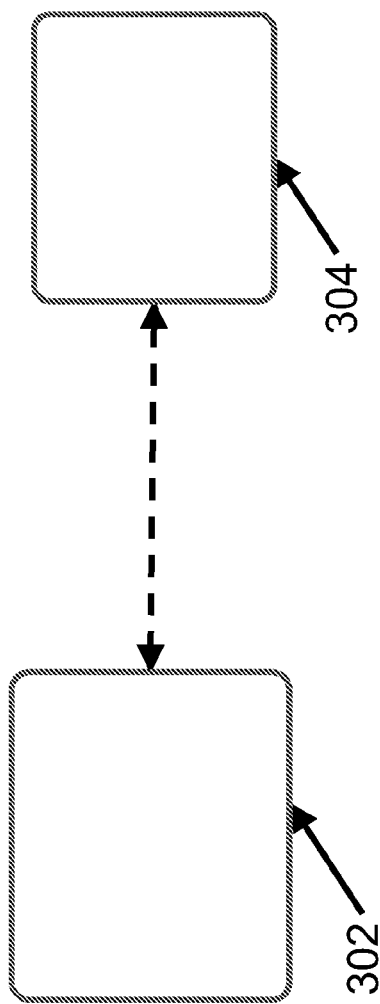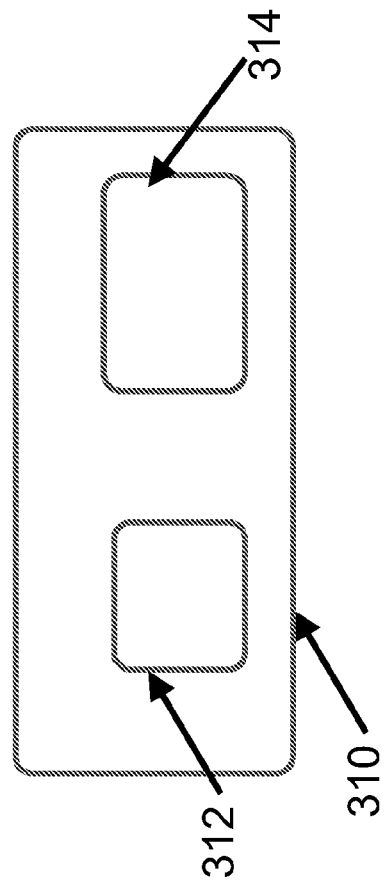
FIG. 3A
FIG. 3B

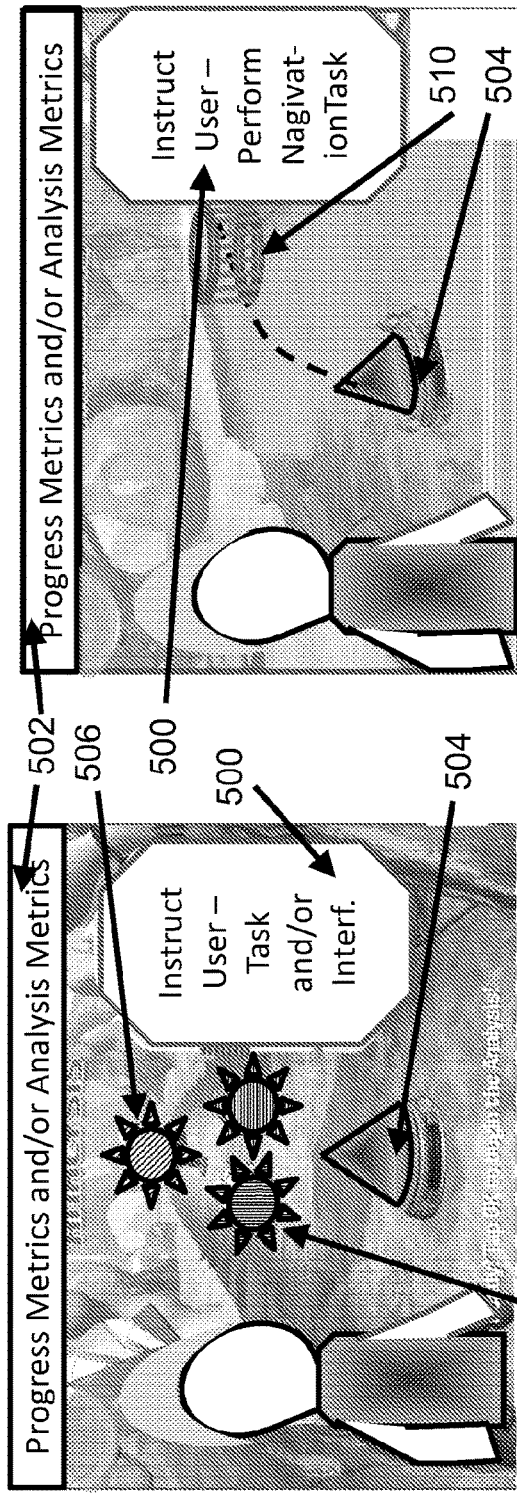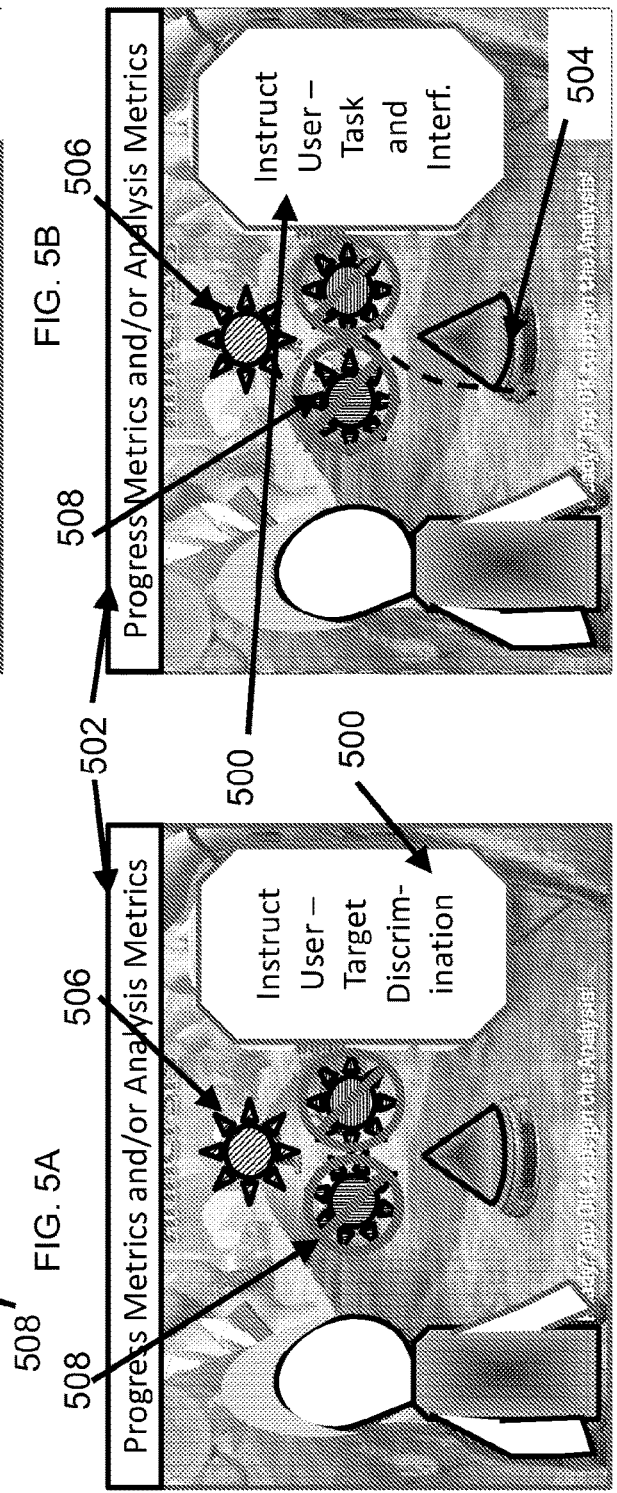

| Parameter | | Methylphenidate (N=28) | | Placebo (N=26) | |
|---|---|---|---|---|---|
| | | Amyloid (+) | Amyloid (−) | Amyloid (+) | Amyloid (−) |
| Age (years) | 70-74 | 11 | 7 | 11 | 7 |
| | 75-79 | 3 | 4 | 6 | 2 |
| | ≥80 | 3 | 0 | 0 | 0 |
| | N | 17 | 11 | 17 | 9 |
| | Mean | 73.9 | 73.6 | 73.4 | 73.2 |
| | Std. Dev. | 3.44 | 2.34 | 3.12 | 2.86 |
| Gender | Female (%) | 10 (58.82) | 6 (54.55) | 12 (70.59) | 6 (66.67) |
| | Male (%) | 7 (41.18) | 5 (45.45) | 5 (29.41) | 3 (33.33) |
| ApoE Status | Carrier (%) | 7 (46.67) | 1 (9.09) | 9 (52.94) | 2 (25.00) |
| | Non-Carrier (%) | 8 (53.33) | 10 (90.91) | 8 (47.06) | 6 (75.00) |
| Cortical thickness in AD Signature regions | N | 17 | 11 | 17 | 9 |
| | Mean | 2.865 | 2.727 | 2.800 | 2.750 |
| | Std. Dev. | 0.1256 | 0.1580 | 0.1876 | 0.1147 |

N is the number of subjects in Per Protocol Analysis Set 2. n is the number of subjects in Per Protocol Analysis Set 2 and having valid values.
Per Protocol Analysis Set 2 consists of all subjects randomized who have completed sufficient daily training on the cognitive platform and have received randomized treatment on both day 0 and day 28.
ApoE E4 carrier: E2/E4, E3/E4, E4/E4 paired alleles. ApoE E4 non-carrier: E2/E2, E2/E3, E3/E3 paired alleles.
Alzheimer's Disease (AD) Signature is the arithmetic mean of thickness of chubs-ifc, chubs-ipc, chubs-ips, chubs-lateral temporal, chubs-mtl, chubs-retrosplenial, chubs-tp.

FIG. 8A

| Parameter | | Methylphenidate (N=28) | | Placebo (N=26) | |
|---|---|---|---|---|---|
| | | Amyloid (+) | Amyloid (−) | Amyloid (+) | Amyloid (−) |
| Normalized Bilateral Hippocampal Volumes | N | 17 | 11 | 17 | 9 |
| | Mean | 0.0058 | 0.0053 | 0.0058 | 0.0057 |
| | Std. Dev. | 0.00062 | 0.00066 | 0.00077 | 0.00109 |
| Normalized Bilateral Whole-Brain Volumes | N | 17 | 11 | 17 | 9 |
| | Mean | 0.7212 | 0.6994 | 0.7245 | 0.7063 |
| | Std. Dev. | 0.04648 | 0.04340 | 0.03849 | 0.06988 |
| SUVR | N | 17 | 11 | 17 | 9 |
| | Mean | 1.264 | 0.958 | 1.329 | 1.008 |
| | Std. Dev. | 0.1109 | 0.0445 | 0.1453 | 0.0578 |
| MRI Microbleed Count – Deep | N | 16 | 11 | 17 | 9 |
| | Mean | 0.1 | 1.0 | 0.1 | 0.0 |
| | Std. Dev. | 0.34 | 3.32 | 0.24 | 0.00 |
| MRI Microbleed Count – Lobar | N | 16 | 11 | 17 | 9 |
| | Mean | 0.0 | 1.5 | 0.1 | 0.0 |
| | Std. Dev. | 0.00 | 3.36 | 0.24 | 0.00 |
| N is the number of subjects. Normalized volume means dividing the volume by the intracranial volume. Standard uptake value ratios (SUVR) computed following positron emission tomography (PET) imaging | | | | | |

FIG. 8B

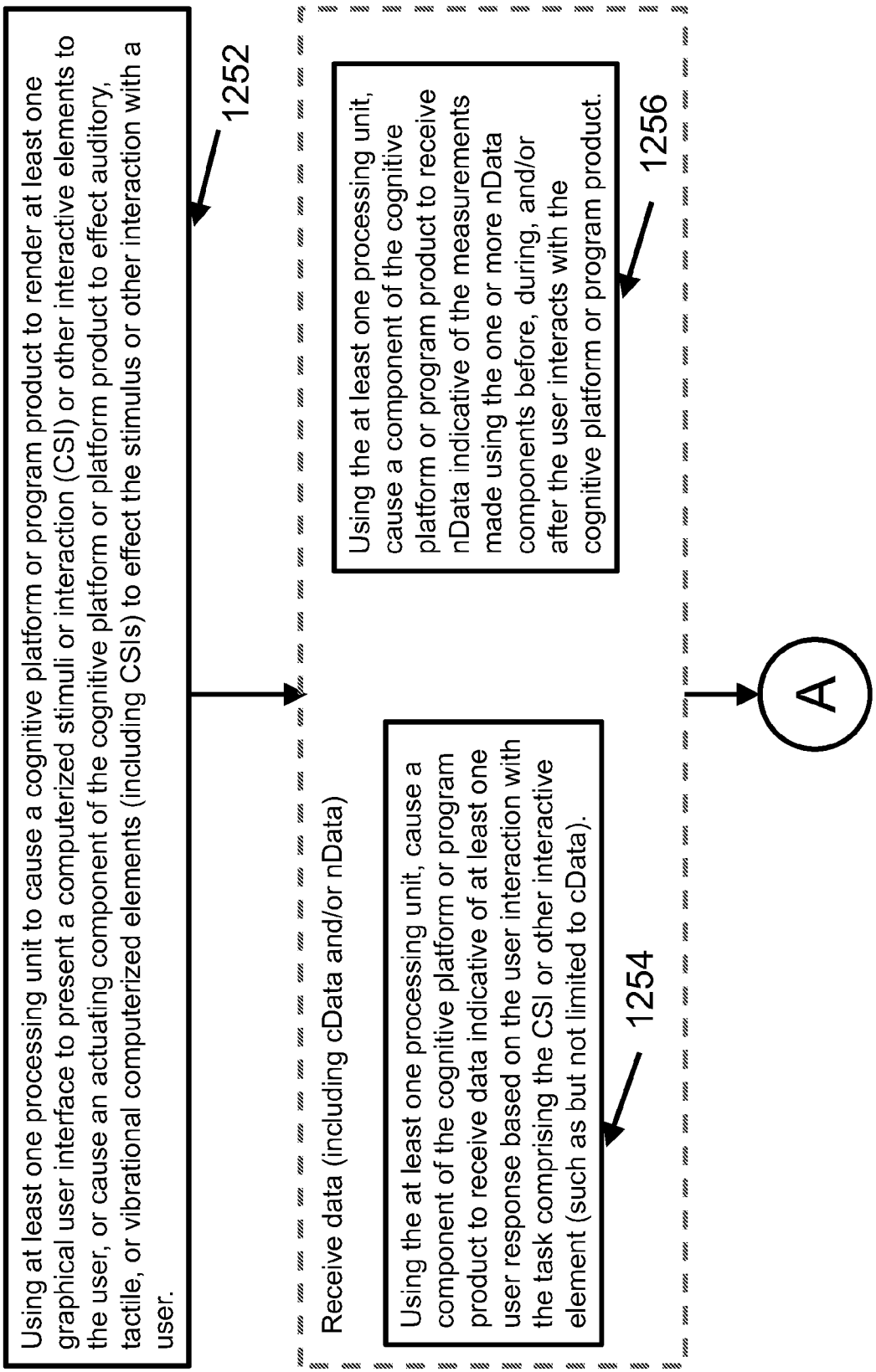

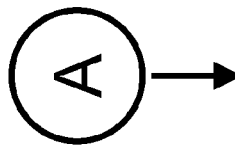

Using the at least one processing unit to: analyze the cData and/or nData to provide a measure of the individual's physiological condition and/or cognitive condition, and/or analyze the differences in the individual's performance based on determining the differences between the user's responses (including based on differences in the cData) and differences in the associated the nData, and/or adjust the difficulty level of the task(s) comprising the CSI or other interactive elements based on the analysis of the cData and/or nData (including the measures of the individual's performance and/or physiological condition determined in the analysis), and/or provide an output or other feedback from the platform product that can be indicative of the individual's performance, and/or cognitive assessment, and/or response to cognitive treatment, and/or assessed measures of cognition, and/or to classify an individual as to amyloid group, and/or APOE expression group (or other expression group based on the expression level of other protein(s) that can be of clinical interest in a neurodegenerative condition), and/or potential efficacy of use of the cognitive platform or platform product when the individual is administered a drug, biologic or other pharmaceutical agent, and/or an expected score from the individual's performance of a TOVA® test and/or a RAVLT™ test, and/or to classify an individual as to likelihood of onset and/or stage of progression of a neurodegenerative condition, and/or to determine a change in dosage of a drug, biologic or other pharmaceutical agent to the individual or to determine an optimal type or combination of drug, biologic or other pharmaceutical agent to the individual.

COGNITIVE PLATFORM CONFIGURED AS A BIOMARKER OR OTHER TYPE OF MARKER

CROSS-REFERENCE TO RELATED APPLICATIONS

This application claims priority to and benefit from international patent application number PCT/US2017/058103, filed Oct. 24, 2017, which claims priority to and benefit from U.S. provisional application No. 62/412,215, entitled "COGNITIVE PLATFORM FOR IDENTIFICATION OF BIOMARKERS AND OTHER TYPES OF MARKERS" filed on Oct. 24, 2016. The entire disclosure of each of these two applications is incorporated herein in its entirety, including drawings.

BACKGROUND OF THE DISCLOSURE

Neurodegenerative conditions can cause individuals to experience a certain amount of cognitive decline. This can cause an individual to experience increased difficulty in challenging situations, such as time-limited, attention-demanding conditions. In both older and younger individuals, certain cognitive conditions, diseases, or executive function disorders can result in compromised performance at tasks that require attention, memory, motor function, reaction, executive function, decision-making skills, problem-solving skills, language processing, or comprehension. Alzheimer's disease and Huntington's disease, among other types of neurodegenerative conditions, eventually cause diminished cognitive abilities.

To detect the potential onset or stage of progression of a neurodegenerative condition, medical and healthcare practitioners use physiological techniques. But such physiological measurements can require massive equipment and, be expensive and time-consuming, and some can be painful.

SUMMARY OF THE DISCLOSURE

In view of the foregoing, apparatus, systems and methods are provided for generating an assessment of one or more cognitive skills in an individual as an indication of a neurodegenerative condition of the individual. In a general aspect, an apparatus for generating an assessment of one or more cognitive skills in an individual as an indication of a neurodegenerative condition of the individual is provided. The apparatus includes a user interface; a memory to store processor-executable instructions; and a processing unit communicatively coupled to the user interface and the memory. Upon execution of the processor-executable instructions by the processing unit, the processing unit is configured to: render a first instance of a primary task at the user interface, requiring a first primary response from the individual to the first instance of the primary task; render a first instance of a secondary task at the user interface, requiring a first secondary response from the individual to the first instance of the secondary task; and render at the user interface a second instance of the primary task with an interference, requiring a second primary response from the individual to the second instance of the primary task in the presence of the interference, in which the interference is configured to divert the individual's attention from the second instance of the primary task and is configured as a second instance of the secondary task that is rendered as an interruptor or a distraction. The processing unit is configured to, using the user interface, instruct the individual not to respond to the interference that is configured as a distraction and to respond to the interference that is configured as an interruptor; receive data indicative of the first primary response, the first secondary response, the second primary response, and the response to the interference; analyze the differences in the individual's performance from performing the primary task without interference and with interference at least in part by determining differences between the data indicative of the first primary response and the second primary response, and also analyzing one or both of the first secondary response or the response to the interference, to determine at least one indicator of the cognitive ability of the individual; and generate a scoring output indicative of a likelihood of onset of a neurodegenerative condition of the individual and/or a stage of progression of the neurodegenerative condition based at least in part on applying the first predictive model to the at least one indicator.

Implementations can include one or more of the following features. The first predictive model can be trained using a plurality of training datasets, each training dataset corresponding to a previously classified individual of a plurality of individuals, and each training dataset including data representing the at least one indicator of the cognitive ability of the classified individual and data indicative of a diagnosis of a status or progression of the neurodegenerative condition in the classified individual. The first predictive model can include one or more of a linear/logistic regression, principal component analysis, a generalized linear mixed model, a random decision forest, a support vector machine, or an artificial neural network. Prior to rendering the first instance of a primary task at the user interface, the processing unit can be configured to receive data indicative of one or more of an amount, concentration, or dose titration of a pharmaceutical agent, drug, or biologic being or to be administered to an individual. The processing unit can be configured to, based at least in part on the scoring output, generate an output to the user interface indicative of one or more of: (i) a likelihood of the individual experiencing an adverse event in response to administration of the pharmaceutical agent, drug, or biologic, (ii) a likelihood of the individual experiencing an adverse event in response to a change in one or more of the amount, concentration, or dose titration of the pharmaceutical agent, drug, or biologic, (iii) a change in the individual's cognitive response capabilities, (iv) a recommended treatment regimen, (v) a recommendation of at least one of a behavioral therapy, counseling, or physical exercise, or (vi) a determination of a degree of effectiveness of at least one of a behavioral therapy, counseling, or physical exercise. The processing unit can be configured to generate an output to the user interface indicative of a likelihood of the individual experiencing an adverse event in response to administration of the pharmaceutical agent, drug, or biologic, or a likelihood of the individual experiencing an adverse event in response to a change in one or more of the amount, concentration, or dose titration of the pharmaceutical agent, drug, or biologic. The biologic, drug or other pharmaceutical agent can include one or more of methylphenidate (MPH), scopolamine, donepezil hydrochloride, rivastigmine tartrate, memantine HCl, solanezumab, aducanumab, or crenezumab.

The neurodegenerative condition can be selected from the group consisting of Alzheimer's disease, dementia, Parkinson's disease, cerebral amyloid angiopathy, familial amyloid neuropathy, or Huntington's disease. The first predictive model can be trained to classify the individual as to a level of expression of one or more of an amyloid, an cystatin, an alpha-synuclein, a huntingtin protein, a tau protein, or an apolipoprotein E. The apparatus can include one or more sensor components, and the processing unit can be configured to control the one or more sensor components to measure the data indicative of one or both of the first primary response and the second primary response. The one or more sensor components can include one or more of a gyroscope, an accelerometer, a motion sensor, a position sensor, a pressure sensor, an optical sensor, a video camera, an auditory sensor, or a vibrational sensor. The processing unit can be further configured to use the scoring output for one or more of: (i) identifying a likelihood of the individual experiencing an adverse event in response to a change of one or more of a recommended amount, concentration, or dose titration of the pharmaceutical agent, drug, or biologic, (ii) identifying a likelihood of the individual experiencing an adverse event in response to administration of the pharmaceutical agent, drug, or biologic, (iii) identifying a change in the individual's cognitive capabilities, (iv) recommending a treatment regimen, (v) recommending at least one of a behavioral therapy, counseling, or physical exercise, or (vi) determining a degree of effectiveness of at least one of a behavioral therapy, counseling, or physical exercise.

The processing unit can be configured to transmit the scoring output to the user and/or display the scoring output on the user interface. The first predictive model can serve as an intelligent proxy for subsequent measures of the neurodegenerative condition of the individual. The processing unit can be configured to render the first instance of the primary task as a continuous visuo-motor tracking task, and the first instance of the primary task can be a first time interval of the continuous visuo-motor task. The processing unit can be configured to control the user interface to render the interference as a target discrimination interference. The processing unit can be configured to: (i) receive a secondary response to the interference at substantially the same time as the processing unit receives the second primary response; or (ii) receive the secondary response to the interference that is an interruptor at substantially the same time as the processing unit receives the first primary response and not receive the secondary response to the interference that is a distraction at substantially the same time that processing unit receives the first primary response. The at least one indicator can be computed as an interference cost. The at least one indicator can include an indicator of a projected response of the individual to a cognitive treatment being or to be delivered. The processing unit can be further configured to render a feature including user instructions instructing the individual not to respond to the interference that is configured as a distraction and to respond to the interference that is configured as an interruptor.

The system can be configured as at least one of a virtual reality system, an augmented reality system, or a mixed reality system. The apparatus can be configured as at least one of a smartphone, a tablet, a slate, an electronic-reader (e-reader), a digital assistant, a portable computing device, a wearable computing device, or a gaming device. A system can include one or more physiological components and an apparatus described above, in which upon execution of the processor-executable instructions by the processing unit, the processing unit can be configured to: receive data indicative of one or more measurements of the physiological component; and analyze the data indicative of the first primary response and the second primary response, and the data indicative of the one or more measurements of the physiological component to compute the at least one indicator.

In another general aspect, a computer-implemented method for enhancing one or more cognitive skills in an individual to provide an indication of a neurodegenerative condition of the individual is provided, the method being implemented using a computing device comprising a processing unit and an input device. The method includes: using the processing unit, executing a first trial at a first time interval, the first trial comprising: rendering a first instance of a primary task, requiring a first primary response from the individual to the first instance of the primary task using the input device; rendering a second instance of the primary task with a first interference, requiring a second primary response from the individual, using the input device, to the second instance of the primary task in the presence of the first interference; wherein the first interference is configured to divert the individual's attention from the second instance of the primary task and is rendered as an interruptor or a distraction; and wherein the individual is instructed not to respond to the first interference that is configured as a distraction and to respond to the first interference that is configured as an interruptor. The method includes: using the processing unit, executing a second trial at a second time interval that is subsequent to the first time interval, the second trial comprising: rendering a third instance of the primary task, requiring a third primary response from the individual to the third instance of the primary task using the input device; rendering a fourth instance of the primary task with a second interference, requiring a fourth primary response from the individual using the input device, to the fourth instance of the primary task in the presence of the second interference; wherein the second interference is configured to divert the individual's attention from the fourth instance of the primary task and is rendered as the interruptor or the distraction; and wherein the individual is instructed not to respond to the second interference that is configured as the distraction and to respond to the second interference that is configured as the interruptor; and receiving data indicative of the first primary response, the second primary response, the third primary response, and the fourth primary response. The method includes: using the processing unit, analyze the differences in the individual's performance from performing the primary task without interference and with interference at least in part by determining differences between the data indicative of the first primary response, the second primary response, the third primary response, and the fourth primary response, to determine at least a first indicator of the cognitive ability of the individual; and using the processing unit, generate a scoring output indicative of a likelihood of onset of a neurodegenerative condition of the individual and/or a stage of progression of the neurodegenerative condition based at least in part on applying the first predictive model to the at least the first indicator.

Implementations can include one or more of the following features. The first predictive model can be trained using a plurality of training datasets, each training dataset corresponding to a previously classified individual of a plurality of individuals, and each training dataset comprising data representing the at least the first indicator of the cognitive ability of the classified individual and data indicative of a diagnosis of a status or progression of the neurodegenerative condition in the classified individual. The first time interval and the second time interval can be separated by about 5 minutes, about 7 minutes, about 15 minutes, about 1 hour, about 12 hours, about 1 day, about 5 days, about 10 days, about 15 days, about 20 days, about 28 days, about a month, or greater than a month.

The first predictive model can include one or more of a linear/logistic regression, principal component analysis, a generalized linear mixed model, a random decision forest, a support vector machine, or an artificial neural network. The processing unit can be further configured to execute instructions and perform: applying at least one adaptive procedure to modify the primary task and/or the first interference, such that analysis of the data indicative of the third primary response and/or the fourth primary response indicates a modification of the at least the first indicator. The neurodegenerative condition can be selected from the group consisting of Alzheimer's disease, dementia, Parkinson's disease, cerebral amyloid angiopathy, familial amyloid neuropathy, or Huntington's disease. The first predictive model can be trained to classify the individual as to a level of expression of one or more of an amyloid, an cystatin, an alpha-synuclein, a huntingtin protein, a tau protein, or an apolipoprotein E.

The processing unit can be configured to control one or more sensor components to measure the data indicative of one or more of the first primary response, the second primary response, the third primary response, or the fourth primary response. The one or more sensor components can include one or more of a gyroscope, an accelerometer, a motion sensor, a position sensor, a pressure sensor, an optical sensor, a video camera, an auditory sensor, or a vibrational sensor. The processing unit can be further configured to use the scoring output for one or more of: (i) identifying a likelihood of the individual experiencing an adverse event in response to a change of one or more of a recommended amount, concentration, or dose titration of the pharmaceutical agent, drug, or biologic, (ii) identifying a likelihood of the individual experiencing an adverse event in response to administration of the pharmaceutical agent, drug, or biologic, (iii) identifying a change in the individual's cognitive capabilities, (iv) recommending a treatment regimen, (v) recommending at least one of a behavioral therapy, counseling, or physical exercise, or (vi) determining a degree of effectiveness of at least one of a behavioral therapy, counseling, or physical exercise. The processing unit can be configured to generate an output to the user interface indicative of a likelihood of the individual experiencing an adverse event in response to administration of the pharmaceutical agent, drug, or biologic, or a likelihood of the individual experiencing an adverse event in response to a change in one or more of the amount, concentration, or dose titration of the pharmaceutical agent, drug, or biologic. The biologic, drug or other pharmaceutical agent can include one or more of methylphenidate (MPH), scopolamine, donepezil hydrochloride, rivastigmine tartrate, memantine HCl, solanezumab, aducanumab, or crenezumab.

The processing unit can be configured to transmit the scoring output to the user and/or display the scoring output on a user interface. The first predictive model can serve as an intelligent proxy for subsequent measures of the neurodegenerative condition of the individual. The processing unit can be configured to render the first instance of the primary task as a continuous visuo-motor tracking task, and wherein the first instance of the primary task and the second instance of the primary task can be a first time interval of the continuous visuo-motor task. The processing unit can be configured to render the first interference and second interference as a target discrimination interference. The processing unit can be configured to: (i) receive a secondary response to the first interference at substantially the same time as the processing unit receives the second primary response; or (ii) receive the secondary response to the first interference that is an interruptor at substantially the same time as the processing unit receives the first primary response and not receive the secondary response to the first interference that is a distraction at substantially the same time that processing unit receives the first primary response.

The method can further include adjusting a difficulty of one or both of the primary task or the first interference such that the apparatus renders at a second difficulty level one or more of: the third instance of the primary task, the fourth instance of the primary task, or the second interference. The method can further include using the computing device, executing a third trial at a third time interval that is subsequent to the second time interval, the third trial including: rendering a fifth instance of the primary task, requiring a fifth primary response from the individual to the fifth instance of the primary task using the input device; rendering a sixth instance of the primary task with a third interference, requiring a sixth primary response from the individual using the input device, to the sixth instance of the primary task in the presence of the third interference; wherein the third interference is configured to divert the individual's attention from the sixth instance of the primary task and is rendered as the interruptor or the distraction; and wherein the individual is instructed not to respond to the third interference that is configured as the distraction and to respond to the third interference that is configured as the interruptor.

The method can further include receiving data indicative of the fifth primary response and the sixth primary response; using the computing device, analyzing the differences in the individual's performance from performing the primary task without interference and with interference at least in part by determining differences between the data indicative of the first primary response, the second primary response, the third primary response, the fourth primary response, the fifth primary response, and the sixth primary response, to determine at least a second indicator of the cognitive ability of the individual; and using the computing device, generating the scoring output indicative of the likelihood of onset of the neurodegenerative condition of the individual and/or the stage of progression of the neurodegenerative condition, based at least in part on applying the first predictive model to the at least the second indicator. The method can further include adjusting a difficulty of one or both of the primary task or the second interference such that the apparatus renders at a second difficulty level one or more of: the fifth instance of the primary task, the sixth instance of the primary task, or the third interference. The at least one indicator can be computed as an interference cost.

In another general aspect, an apparatus including a computing device is provided, the computing device including: an input device; a memory to store processor-executable instructions; and a processing unit communicatively coupled to the user interface and the memory, wherein upon execution of the processor-executable instructions by the processing unit, the processing unit is configured to execute the method described above.

Implementations can include one or more of the following features. A system including the apparatus described above is provided, in which the system can be configured as at least one of a virtual reality system, an augmented reality system, or a mixed reality system. A system including the apparatus described above is provided, in which the apparatus can be configured as at least one of a smartphone, a tablet, a slate, an electronic-reader (e-reader), a digital assistant, a portable computing device, a wearable computing device, or a gaming device.

In another general aspect, an apparatus for enhancing one or more cognitive skills in an individual to provide an indication of a neurodegenerative condition of the individual is provided. The apparatus includes: a user interface; a memory to store processor-executable instructions; and a processing unit communicatively coupled to the user interface and the memory, wherein upon execution of the processor-executable instructions by the processing unit, the processing unit is configured to: render a first instance of a primary task at the user interface, requiring a first primary response from the individual to the first instance of the primary task; render a first instance of a secondary task at the user interface, requiring a first secondary response from the individual to the first instance of the secondary task; using the user interface, instruct the individual not to respond to an interference with the primary task that is configured as a distraction and to respond to an interference with the primary task that is configured as an interruptor; render at the user interface a second instance of the primary task with a first interference, requiring a second primary response from the individual to the second instance of the primary task in the presence of the first interference; wherein the first interference is configured to divert the individual's attention from the second instance of the primary task and is configured as a second instance of the secondary task that is rendered as an interruptor or a distraction. The processing unit is further configured to: receive data indicative of the first primary response, the first secondary response, the second primary response, and the response to the interference; adjust a difficulty of one or both of the primary task or the interference such that the apparatus renders one or both of a third instance of the primary task or a second interference at a second difficulty level; render at the user interface a third instance of the primary task with the second interference, requiring a third primary response from the individual to the third instance of the primary task in the presence of the second interference; receive data indicative of the third primary response and the response to the second interference; analyze the differences in the individual's performance from performing the primary task without interference and with interference at least in part by determining differences between the data indicative of two or more of the first primary response, the second primary response, and the third primary response, and also analyzing at least one of the first secondary response, the response to the first interference, or the response to the second interference, to determine at least one indicator of the cognitive ability of the individual; and generate a scoring output indicative of a likelihood of onset of a neurodegenerative condition of the individual and/or a stage of progression of the neurodegenerative condition, based at least in part on applying a first predictive model to the at least one indicator.

Implementations can include one or more of the following features. The first predictive model can be trained using a plurality of training datasets, each training dataset corresponding to a previously classified individual of a plurality of individuals, and each training dataset comprising data representing the at least one indicator of the cognitive ability of the classified individual and data indicative of a diagnosis of a status or progression of the neurodegenerative condition in the classified individual. The first predictive model can include one or more of a linear/logistic regression, principal component analysis, a generalized linear mixed model, a random decision forest, a support vector machine, or an artificial neural network. Prior to rendering the first instance of a primary task at the user interface, the processing unit can be configured to receive data indicative of one or more of an amount, concentration, or dose titration of a pharmaceutical agent, drug, or biologic being or to be administered to an individual. The processing unit can be configured to, based at least in part on the scoring output, generate an output to the user interface indicative of one or more of: (i) a likelihood of the individual experiencing an adverse event in response to a change one or more of a recommended amount, concentration, or dose titration of the pharmaceutical agent, drug, or biologic, (ii) a likelihood of the individual experiencing an adverse event in response to administration of the pharmaceutical agent, drug, or biologic, (iii) a change in the individual's cognitive capabilities, (iv) a recommended treatment regimen, (v) a recommendation of at least one of a behavioral therapy, counseling, or physical exercise, or (vi) a determination of a degree of effectiveness of at least one of a behavioral therapy, counseling, or physical exercise.

The processing unit can be configured to generate an output to the user interface indicative of a likelihood of the individual experiencing an adverse event in response to administration of the pharmaceutical agent, drug, or biologic, or a likelihood of the individual experiencing an adverse event in response to a change in one or more of the amount, concentration, or dose titration of the pharmaceutical agent, drug, or biologic. The biologic, drug or other pharmaceutical agent can include one or more of methylphenidate (MPH), scopolamine, donepezil hydrochloride, rivastigmine tartrate, memantine HCl, solanezumab, aducanumab, or crenezumab. The neurodegenerative condition can be selected from the group consisting of Alzheimer's disease, dementia, Parkinson's disease, cerebral amyloid angiopathy, familial amyloid neuropathy, or Huntington's disease. The first predictive model can be trained to classify the individual as to a level of expression of one or more of an amyloid, an cystatin, an alpha-synuclein, a huntingtin protein, a tau protein, or an apolipoprotein E. The apparatus can include one or more sensor components, and the processing unit can be configured to control the one or more sensor components to measure the data indicative of one or both of the first primary response and the second primary response. The one or more sensor components can include one or more of a gyroscope, an accelerometer, a motion sensor, a position sensor, a pressure sensor, an optical sensor, a video camera, an auditory sensor, or a vibrational sensor.

The processing unit can be further configured to use the scoring output for one or more of: (i) identifying a likelihood of the individual experiencing an adverse event in response to a change in one or more of a recommended amount, concentration, or dose titration of the pharmaceutical agent, drug, or biologic, (ii) identifying a likelihood of the individual experiencing an adverse event in response to administration of the pharmaceutical agent, drug, or biologic, (iii) identifying a change in the individual's cognitive capabilities, (iv) recommending a treatment regimen, (v) recommending at least one of a behavioral therapy, counseling, or physical exercise, or (vi) determining a degree of effectiveness of at least one of a behavioral therapy, counseling, or physical exercise. The processing unit can be configured to transmit the scoring output to the user and/or display the scoring output on the user interface. The first predictive model can serve as an intelligent proxy for subsequent measures of the neurodegenerative condition of the individual. The processing unit can be configured to render the first instance of the primary task as a continuous visuo-motor tracking task, and the first instance of the primary task can be a first time interval of the continuous visuo-motor task.

The processing unit can be configured to control the user interface to render one or both of the first interference or the second interference as a target discrimination interference. The processing unit can be configured to: (i) receive a secondary response to the first interference at substantially the same time as the processing unit receives the second primary response; or (ii) receive the secondary response to the first interference that is an interruptor at substantially the same time as the processing unit receives the first primary response and not receive the secondary response to the first interference that is a distraction at substantially the same time that processing unit receives the first primary response. The at least one indicator can be computed as an interference cost. The at least one indicator can include an indicator of a projected response of the individual to a cognitive treatment being or to be delivered. The processing unit can be further configured to render a feature including user instructions instructing the individual not to respond to the interference that is configured as a distraction and to respond to the interference that is configured as an interruptor.

A system including an apparatus described above, in which the system can be configured as at least one of a virtual reality system, an augmented reality system, or a mixed reality system. A system including an apparatus described above, in which the apparatus can be configured as at least one of a smartphone, a tablet, a slate, an electronic-reader (e-reader), a digital assistant, a portable computing device, a wearable computing device, or a gaming device. A system including one or more physiological components and an apparatus described above, in which upon execution of the processor-executable instructions by the processing unit, the processing unit is configured to: receive data indicative of one or more measurements of the physiological component; and analyze the data indicative of the first primary response and the second primary response, and the data indicative of the one or more measurements of the physiological component to compute the at least one indicator.

The details of one or more of the above aspects and implementations are set forth in the accompanying drawings and the description below. Other features, aspects, and advantages will become apparent from the description, the drawings, and the claims.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIGS. 3A-3B show example systems, according to the principles herein.

FIGS. 5A-5D show example user interfaces with instructions to a user that can be rendered to an example user interface, according to the principles herein.

FIGS. 8A-8B show example physiological measurement data from a plurality of individuals, according to the principles herein.

FIGS. 12A-12C show flowcharts of example methods, according to the principles herein.

DETAILED DESCRIPTION

Figure 1:
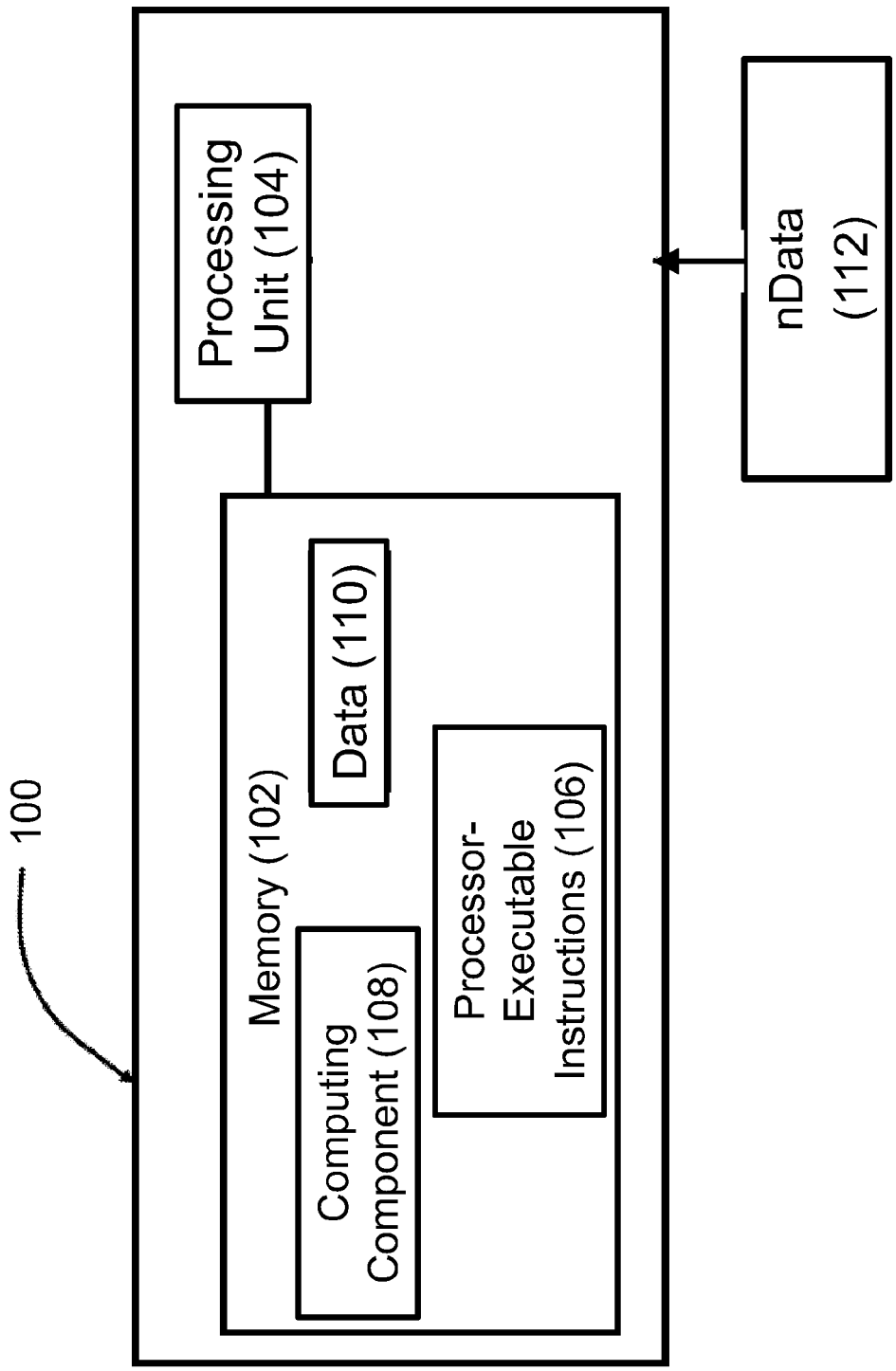
FIG. 1 shows a block diagram of an example apparatus, according to the principles herein.

Non-limiting example computer-implemented cognitive platform described herein can be configured for generating an assessment of one or more cognitive skills of an individual, as a biomarker or other marker for the cognitive condition of an individual. Non-limiting example computer-implemented cognitive platform described herein also can be configured for enhancing the cognitive skills of the individual, and serving as a biomarker or other marker for any change in the cognitive condition of the individual as a result of the enhanced cognitive skills. The cognitive condition can be a neurodegenerative condition, such that the example computer-implemented cognitive platform can be configured to serve as a biomarker or other marker for the likelihood of onset of the neurodegenerative condition and/or the stage of progression of the neurodegenerative condition in the individual.

An example system or apparatus including the computer-implemented cognitive platforms can be configured to apply a predictive model to an indicator of the individual's performance that is derived based on data collected using components of the cognitive platform. For example, the cognitive platform can be configured to render a primary task and/or a secondary task, collect data indicative of the measured response(s) from the individual to the instance of the primary task, and analyze the collected data to determine at least one indicator of the cognitive ability of the individual. The example system or apparatus is configured to apply the predictive model to the at least one indicator to generate a scoring output indicative of the likelihood of onset of the neurodegenerative condition and/or the stage of progression of the neurodegenerative condition, thereby facilitating use of the cognitive platform as a biomarker or other marker.

Methods for training the example predictive model are also described. For example, the predictive model can be computed based on datasets including (i) data indicative of the responses of each individual of a plurality of individuals from their performance of the primary task and/or secondary task, and (ii) data indicative of one or more physiological measurement from the individuals. The one or more physiological measurements can be made either before or after the individual interacts with the cognitive platform, and/or during at least a portion of time periods during which the individual is interacting with the cognitive platform. With the trained predictive model established, the cognitive platform can be implemented to present one or more computer-implemented task(s) to a user, collect data indicative of the user's responses to the one or more computer-implemented task(s), and compute the at least one indicator of the individual's performance. Application of the predictive model to the at least one indicator provides the scoring output that serves as a biomarker or other marker of the neurodegenerative condition, by providing an indication of the likelihood of onset of the neurodegenerative condition and/or the stage of progression of the neurodegenerative condition in the individual.

An advantage of the example systems and apparatus herein including the cognitive platform is that presenting the computer-implemented task(s) to the user and collecting the user's response to the computer-implemented task(s) is comparatively easier and more convenient to the user. In some examples, the indication of the user's cognitive skills and the markers of neurodegenerative condition (derived based on a scoring using the predictive model) can be evaluated without performing physiological measurements (such as but not limited to collecting samples of tissue or fluid from the user, or performing positron emission tomography (PET) scans). The computer-implemented task(s) presented by the cognitive platform can be made interesting, engaging, and fun so that the user is motivated to interact with the cognitive platform regularly, e.g., on a daily basis, or several days in a given month. This allows the indication of the cognitive skills of the user, and the markers of neurodegenerative condition of the user (derived based on a scoring using the predictive model), to be evaluated regularly in a convenient manner. The cognitive platform can track the at least one indicator of the user's cognitive skills over time, and the scoring using the predictive model may be used as a marker of the likelihood of onset of the neurodegenerative condition and/or the stage of progression of the neurodegenerative condition in the individual. In an example where the scoring may be used to facilitate an early detection of a neurodegenerative condition in an individual, remedial measures may be performed relative to the individual's cognitive condition.

The computer-implemented cognitive platform provides a technical solution to the technical problem of using computers or machines to assist a medical practitioner or healthcare provider to evaluate the individual's cognitive condition (including the neurodegenerative condition of the individual). The use of the computer-implemented cognitive platform provides several improvements over conventional methods that may rely on physiological measurement data to detect a neurodegenerative condition or track the progression of the neurodegenerative condition of the user. Since the physiological measurements (e.g., measurements of types of protein and/or conformation of proteins in the tissue or fluid of an individual, or PET scans) often need to be performed by medical professionals, the physiological measurement data are updated infrequently, e.g., perhaps once or twice a year. For an individual with a neurodegenerative condition that progresses rapidly, such a delay could prove detrimental, and in the time delay between the annual or semi-annual checkups, the individual's cognitive skills or neurodegenerative condition may be markedly degraded.

By contrast, the example cognitive platform according to the principles herein are configured for ease of use, and the example cognitive platform can be operated by the users in a more comfortable setting (such as at home) and can be more conveniently administered. In an example where the measures of the individual's cognitive abilities using the cognitive platform may provide an early sign of a biomarker or other marker of a likelihood of onset of the neurodegenerative condition and/or the stage of progression of the neurodegenerative condition, with the individual's consent, an output message may be transmitted to a medical practitioner or healthcare provider. The cognitive platform can be used in a user's home so that the individualized treatment can be conveniently administered to the user.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems including a cognitive platform configured for coupling with one or more other types of measurement components (such as but not limited to one or more physiological component), and for analyzing data indicative of at least one measurement of the one or more other types of measurement components. As non-limiting examples, the cognitive platform can be configured for cognitive training and/or for clinical purposes. According to the principles herein, the cognitive platform may be coupled to (including being in communication with), or integrated with, one or more physiological or monitoring components and/or one or more cognitive testing components.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, the term "including" means including but not limited to. The term "based on" means based at least in part on.

As used herein, the term "stimulus" refers to a sensory event configured to evoke a specified functional response from an individual. The degree and type of response can be quantified based on the individual's interactions with a measuring component (including using sensor devices or other measuring components). For example, the degree of response can be generated based on a degree of an action measured using a sensor (such as but not limited to the degree or rotation measured using a motion sensor or a gyroscope). Non-limiting examples of a stimulus include a navigation path (with an individual being instructed to control an avatar or other processor-rendered guide to navigate the path), or a discrete object, whether a target or a non-target, rendered to a user interface (with an individual being instructed to control a computing component to provide input or other indication relative to the discrete object). In any example herein, the task and/or interference includes a stimulus, which can be a time-varying feature as described hereinbelow.

As used herein, the term "target" refers to a type of stimulus that is specified to an individual (e.g., in instructions) to be the focus for an interaction. A target differs from a non-target in at least one characteristic or feature. Two targets may differ from each other by at least one characteristic or feature, but overall are still instructed to an individual as a target, in an example where the individual is instructed/required to make a response that indicates a choice.

As used herein, the term "non-target" refers to a type of stimulus that is not to be the focus for an interaction, whether indicated explicitly or implicitly to the individual.

As used herein, the term "task" refers to a goal and/or objective to be accomplished by an individual. Using the example systems, methods, and apparatus described herein, the computerized task is rendered using programmed computerized components, and the individual is instructed (e.g., using a computing device) as to the intended goal or objective from the individual for performing the computerized task. The task may require the individual to provide or withhold a response to a particular stimulus, using at least one component of the computing device (e.g., one or more sensor components of the computing device). The "task" can be configured as a baseline cognitive function that is being measured.

As used herein, the term "interference" refers to a type of stimulus presented to the individual such that it interferes with the individual's performance of a primary task. In any example herein, an interference is a type of task that is presented/rendered in such a manner that it diverts or interferes with an individual's attention in performing another task (including the primary task). In some examples herein, the interference is configured as an instance of a secondary task that is presented simultaneously with a primary task, either over a discrete time period (e.g., a short, discrete time period) or over an extended time period (e.g., less than the time frame over which the primary task is presented), or over the entire period of time of the primary task. In any example herein, the interference can be presented/rendered continuously, or continually (i.e., repeated in a certain frequency, irregularly, or somewhat randomly). For example, the interference can be presented at the end of the primary task or at discrete, interim periods during presentation of the primary task. The degree of interference can be modulated based on the type, amount, and/or temporal length of presentation of the interference relative to the primary task.

As used herein, a "trial" includes at least one iteration of rendering of a task and/or interference (either or both with time-varying feature) and at least one receiving of the individual's response(s) to the task and/or interference (either or both with time-varying feature). As non-limiting examples, a trial can include at least a portion of a single-tasking task and/or at least a portion of a multi-tasking task. For example, a trial can be a period of time during a navigation task (including a visuo-motor navigation task) in which the individual's performance is assessed, such as but not limited to, assessing whether or the degree of success to which an individual's actions in interacting with the platform result in a guide (including a computerized avatar) navigating along at least a portion of a certain path or in an environment for a time interval (such as but not limited to, fractions of a second, a second, several seconds, or more) and/or causes the guide (including computerized avatar) to cross (or avoid crossing) performance milestones along the path or in the environment. In another example, a trial can be a period of time during a targeting task in which the individual's performance is assessed, such as but not limited to, assessing whether or the degree of success to which an individual's actions in interacting with the platform result in identification/selection of a target versus a non-target (e.g., red object versus yellow object), or discriminates between two different types of targets. In these examples, the segment of the individual's performance that is designated as a trial for the navigation task does not need to be co-extensive or aligned with the segment of the individual's performance that is designated as a trial for the targeting task.

In any example herein, an object may be rendered as a depiction of a physical object (including a polygonal or other object), a face (human or non-human), or a caricature, other type of object.

In any of the examples herein, instructions can be provided to the individual to specify how the individual is expected to perform the task and/or interference (either or both with time-varying feature) in a trial and/or a session. In non-limiting examples, the instructions can inform the individual of the expected performance of a navigation task (e.g., stay on this path, go to these parts of the environment, cross or avoid certain milestone objects in the path or environment), a targeting task (e.g., describe or show the type of object that is the target object versus the non-target object, or describe or show the type of object that is the target object versus the non-target object, or two different types of target object that the individual is expected to choose between, and/or describe how the individual's performance is to be scored. In examples, the instructions may be provided visually (e.g., based on a rendered user interface) or via sound. In various examples, the instructions may be provided once prior to the performance two or more trials or sessions, or repeated each time prior to the performance of a trial or a session, or some combination thereof.

While some example systems, methods, and apparatus described herein are based on an individual being instructed/required to decide/select between a target versus a non-target may, in other example implementations, the example systems, methods, and apparatus can be configured such that the individual is instructed/required to decide/choose between two different types of targets (such as but not limited to between two different degrees of a facial expression or other characteristic/feature difference).

In addition, while example systems, methods, and apparatus may be described herein relative to an individual, in other example implementations, the example systems, methods, and apparatus can be configured such that two or more individuals, or members of a group (including a clinical population), perform the tasks and/or interference (either or both with time-varying feature), either individually or concurrently.

The example platform products and cognitive platforms according to the principles described herein can be applicable to many different types of conditions, such as but not limited to Alzheimer's disease, dementia, Parkinson's disease, cerebral amyloid angiopathy, familial amyloid neuropathy, Huntington's disease, or other neurodegenerative condition.

As described in greater detail below, the computing device can include an application (an "App program") to perform such functionalities as analyzing the data. For example, the data from the at least one sensor component can be analyzed as described herein by a processor executing the App program on an example computing device to receive (including to measure) substantially simultaneously to the response from the individual to a primary task and a secondary response of the individual to a secondary task rendered as an interference with the primary task. As another example, the data from the at least one sensor component can be analyzed as described herein by a processor executing the App program on an example computing device to analyze the data indicative of the response of the individual to the primary task and to the secondary task to compute at least one performance metric including at least one indicator of cognitive condition.

An example system according to the principles herein can be configured to implement a predictive model (including using a machine learning predictive model, such as but not limited to a machine learning classifier) to enable an assessment of cognitive skills in an individual using a predictive model and/or to enhance cognitive skills in an individual. In an example implementation, the example system employs an App program executing on a mobile communication device or other hand-held devices. Non-limiting examples of such mobile communication devices or hand-held device include a smartphone, such as but not limited to an iPhone®, a BlackBerry®, or an Android-based smartphone, a tablet, a slate, an electronic-reader (e-reader), a digital assistant, or other electronic reader or hand-held, portable, or wearable computing device, or any other equivalent device, an Xbox®, a Wii®, or other computing system that can be used to render game-like elements. In some example implementations, the example system can include a head-mounted device, such as smart eyeglasses with built-in displays, a smart goggle with built-in displays, or a smart helmet with built-in displays, and the user can hold a controller or an input device having one or more sensors in which the controller or the input device communicates wirelessly with the head-mounted device. In some example implementations, the computing system may be stationary, such as a desktop computing system that includes a main computer and a desktop display (or a projector display), in which the user provides inputs to the App program using a keyboard, a computer mouse, a joystick, handheld consoles, wristbands, or other wearable devices having sensors that communicate with the main computer using wired or wireless communication. In other examples herein, the example system may be a virtual reality system, an augmented reality system, or a mixed reality system. In examples herein, the sensors can be configured to measure movements of the user's hands, feet, and/or any other part of the body. In some example implementations, the example system can be formed as a virtual reality (VR) system (a simulated environment including as an immersive, interactive 3-D experience for a user), an augmented reality (AR) system (including a live direct or indirect view of a physical, real-world environment whose elements are augmented by computer-generated sensory input such as but not limited to sound, video, graphics and/or GPS data), or a mixed reality (MR) system (also referred to as a hybrid reality which merges the real and virtual worlds to produce new environments and visualizations where physical and digital objects co-exist and interact substantially in real time).

As used herein, the term "predictive model" encompasses models trained and developed based on continuous output values and/or models based on discrete labels. In any example herein, the predictive model encompasses a classifier model. For example, the predictive model can be configured to determine scoring outputs that are continuous output values (such as but not limited to values of a psychometric curve) or discrete values (such as but not limited to a classification output). In another example, the systems, methods, and apparatus, scoring outputs that are continuous output values can be binned into two or more bins (each bin corresponding to a pre-set range of output values), to provide the classification output.

Any example predictive model according to the principles herein can be trained using a plurality of training datasets. Each training dataset corresponds to a previously measured individual of a plurality of individuals. Each training dataset includes data representing at least one indicator of the cognitive ability of the previously measured individual, generated based on the data indicative of the individual's responses from previous interactions with the tasks and/or interference executed by the cognitive platform, and nData indicative of a diagnosis of a status or progression of the neurodegenerative condition in the classified individual. The trained predictive model can be applied to the at least one indicator of the cognitive ability of the individual (derived from the data indicative of the individual's interactions with the tasks and/or interference executed by the cognitive platform), to generate a scoring output. The scoring output can be used to provide an indication of a likelihood of onset of a neurodegenerative condition and/or a stage of progression of the neurodegenerative condition of an individual.

The instant disclosure is directed to computer-implemented devices formed as example platform products configured to implement software and/or other processor-executable instructions for the purpose of measuring data indicative of a user's performance at one or more tasks, to provide a user performance metric. The example performance metric can be used to derive an assessment of a user's cognitive abilities and/or to measure a user's response to a cognitive treatment, and/or to provide data or other quantitative indicia of a user's condition (including physiological condition and/or cognitive condition). Non-limiting example cognitive platforms or platform products according to the principles herein can be configured to classify an individual as to amyloid group, and/or apolipoprotein E (APOE Expression Group) based on APOE expression level (or other expression group based on the expression level of other protein(s) that can be of clinical interest in a neurodegenerative condition), and/or potential efficacy of use of the cognitive platform or platform product when the individual is administered a drug, biologic or other pharmaceutical agent, and/or expected score from the individual's performance of a TOVA® test and/or a RAVLT™ test, based on the data collected from the individual's interaction with the cognitive platform or platform product and/or metrics computed based on the analysis (and associated computations) of that data. Yet other non-limiting example cognitive platforms or platform products according to the principles herein can be configured to classify an individual as to likelihood of onset and/or stage of progression of a neurodegenerative condition, based on the data collected from the individual's interaction with the cognitive platform or platform product and/or metrics computed based on the analysis (and associated computations) of that data. The neurodegenerative condition can be, but is not limited to, Alzheimer's disease, dementia, Parkinson's disease, cerebral amyloid angiopathy, familial amyloid neuropathy, or Huntington's disease.

Any scoring output of a predictive model (including a classification output of a classifier model) for an individual providing an indication as to likelihood of onset and/or stage of progression of a neurodegenerative condition according to the principles herein can be transmitted as a signal to a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in dosage of a drug, biologic or other pharmaceutical agent to the individual or to determine an optimal type or combination of drug, biologic or other pharmaceutical agent to the individual.

In any example herein, the platform product or cognitive platform can be configured as any combination of a medical device platform, a monitoring device platform, a screening device platform, or other device platform.

The instant disclosure is also directed to example systems that include platform products and cognitive platforms that are configured for coupling with one or more physiological or monitoring component and/or cognitive testing component. In some examples, the systems include platform products and cognitive platforms that are integrated with the one or more other physiological or monitoring component and/or cognitive testing component. In other examples, the systems include platform products and cognitive platforms that are separately housed from and configured for communicating with the one or more physiological or monitoring component and/or cognitive testing component, to receive data indicative of measurements made using such one or more components.

As used herein, the term "cData" refers to data collected from measures of an interaction of a user with a computer-implemented device formed as a platform product.

As used herein, the term "nData" refers to other types of data that can be collected according to the principles herein. Any component used to provide nData is referred to herein as a nData component.

In any example herein, the data (including cData and nData) is collected with user consent.

In any example herein, the cData and/or nData can be collected in real-time.

In non-limiting examples, the nData can be collected from measurements using one or more physiological or monitoring components and/or cognitive testing components. In any example herein, the one or more physiological components are configured for performing physiological measurements. The physiological measurements provide quantitative measurement data of physiological parameters and/or data that can be used for visualization of physiological structure and/or functions.

As a non-limiting example, nData can be collected from measurements of types of protein and/or conformation of proteins in the tissue or fluid (including blood) of an individual and/or in tissue or fluid (including blood) collected from the individual. In some examples, the tissue and/or fluid can be in or taken from the individual's brain. In other examples, the measurement of the conformation of the proteins can provide an indication of amyloid formation (e.g., whether the proteins are forming aggregates). For example, nData can be collected from measurements made using a positron emission tomography (PET) scanner to provide data indicative of an individual's amyloid level, and/or using a test to measure the type and level of expression of a protein of clinical interest (e.g., a DNA test to provide data indicative of an individual's genotype and/or expression level of the apolipoprotein E ε4 allele (referred to herein as "APOE expression group"). The expression group can be defined based on a threshold expression level of the protein of clinical interest in the neurodegenerative condition, where a measured value of expression level above a pre-specified threshold defines a first expression group and a measured value of expression level below the pre-specified threshold defines a second expression group.

As a non-limiting example, the nData can be collected from measurements of beta amyloid, cystatin, alpha-synuclein, huntingtin protein, and/or tau proteins. In some examples, the nData can be collected from measurements of other types of proteins that may be implicated in the onset and/or progression of a neurodegenerative condition, such as but not limited to Alzheimer's disease, dementia, Parkinson's disease, cerebral amyloid angiopathy, familial amyloid neuropathy, or Huntington's disease.

In a non-limiting example, nData can be used to provide a classification or other grouping that can be assigned to an individual based on measurement data from the one or more physiological or monitoring components and/or cognitive testing components. For example, an individual can be classified in an amyloid group of amyloid positive (A+) or amyloid negative (A−) based on analysis of an image from a PET scan. In an example, certain cData collected from the individual's interaction with the cognitive platform or platform product can co-vary or otherwise correlate with the type of amyloid group the individual may be classified to.

A non-limiting example system, method and apparatus according to the principles herein can be executed to measure cData indicative of the response of the individual(s) to the tasks and/or interference presented to the individual(s), analyze the cData to generate at least one indicator of the cognitive ability of the individual, and apply a predictive model to the at least one indicator of the cognitive ability of the individual derived from the cData, to provide a scoring output indicative of a likelihood of onset and/or stage of progression of a neurodegenerative condition of the individual(s). As a non-limiting example, using a predictive model configured as a classifier model trained to provide a classification output of amyloid status (or grouping), an example system, method and apparatus could be implemented to classify an individual according to amyloid status (or grouping).

An example system, method and apparatus according to the principles herein can be used as an intelligent proxy for a nData measurement or analysis. For example, the system, method and apparatus can be implemented as an intelligent proxy for nData measurement or analysis indicative of a likelihood of onset and/or stage of progression of a neurodegenerative condition of the individual(s), through use of the predictive model to provide the scoring output.

In some examples, the nData can be an identification of a type of biologic, drug or other pharmaceutical agent administered or to be administered to an individual, and/or data collected from measurements of a level of the biologic, drug or other pharmaceutical agent in the tissue or fluid (including blood) of an individual, whether the measurement is made in situ or using tissue or fluid (including blood) using collected from the individual. Non-limiting examples of a biologic, drug or other pharmaceutical agent applicable to any example described herein include methylphenidate (MPH), scopolamine, donepezil hydrochloride, rivastigmine tartrate, memantine HCl, solanezumab, aducanumab, and crenezumab.

It is understood that reference to "drug" herein encompasses a drug, a biologic and/or other pharmaceutical agent.

In a non-limiting example, the physiological instrument can be a fMRI, and the nData can be measurement data indicative of the cortical thickness, brain functional activity changes, or other measure.

In other non-limiting examples, nData can include any data that can be used to characterize an individual's status, such as but not limited to age, gender or other similar data.

In another non-limiting example, the nData can be data indicative of an individual's performance using a testing component, such as but not limited to the Rey Auditory Verbal Learning Test (RAVLT™) by Western Psychological Services (Torrance, Calif.) and/or the Test of Variables of Attention (T.O.V.A.®) by The TOVA Company (Los Alamitos, Calif.).

In any example herein, the data (including cData and nData) is collected with the individual's consent.

In any example herein, the one or more physiological components can include any means of measuring physical characteristics of the body and nervous system, including electrical activity, heart rate, blood flow, and oxygenation levels, to provide the nData. This can include camera-based heart rate detection, measurement of galvanic skin response, blood pressure measurement, electroencephalogram, electrocardiogram, magnetic resonance imaging, near-infrared spectroscopy, and/or pupil dilation measures, to provide the nData.

Other examples of physiological measurements to provide nData include, but are not limited to, the measurement of body temperature, heart or other cardiac-related functioning using an electrocardiograph (ECG), electrical activity using an electroencephalogram (EEG), event-related potentials (ERPs), functional magnetic resonance imaging (fMRI), blood pressure, electrical potential at a portion of the skin, galvanic skin response (GSR), magneto-encephalogram (MEG), eye-tracking device or other optical detection device including processing units programmed to determine degree of pupillary dilation, functional near-infrared spectroscopy (fNIRS), and/or a positron emission tomography (PET) scanner. An EEG-fMRI or MEG-fMRI measurement allows for simultaneous acquisition of electrophysiology (EEG/MEG) nData and hemodynamic (fMRI) nData.

The fMRI also can be used to provide measurement data (nData) indicative of neuronal activation, based on the difference in magnetic properties of oxygenated versus de-oxygenated blood supply to the brain. The fMRI can provide an indirect measure of neuronal activity by measuring regional changes in blood supply, based on a positive correlation between neuronal activity and brain metabolism.

A PET scanner can be used to perform functional imaging to observe metabolic processes and other physiological measures of the body through detection of gamma rays emitted indirectly by a positron-emitting radionuclide (a tracer). The tracer can be introduced into the user's body using a biologically-active molecule. Indicators of the metabolic processes and other physiological measures of the body can be derived from the scans, including from computer reconstruction of two- and three-dimensional images from nData of tracer concentration from the scans. The nData can include measures of the tracer concentration and/or the PET images (such as two- or three-dimensional images).

In any example herein, the cognitive platform and systems including the cognitive platform can be configured to present computerized tasks and platform interactions that inform cognitive assessment (screening or monitoring) or deliver treatment.

In any example herein, a task can involve one or more activities that a user is required to engage in. Any one or more of the tasks can be computer-implemented as computerized stimuli or interaction (described in greater detail below). For a targeting task, the cognitive platform may require temporally-specific and/or position-specific responses from a user. For a navigation task, the cognitive platform may require position-specific and/or motion-specific responses from the user. For a facial expression recognition or object recognition task, the cognitive platform may require temporally-specific and/or position-specific responses from the user. The multi-tasking tasks can include any combination of two or more tasks. In non-limiting examples, the user response to tasks, such as but not limited to targeting and/or navigation and/or facial expression recognition or object recognition task(s), can be recorded using an input device of the cognitive platform. Non-limiting examples of such input devices can include a touch, swipe or other gesture relative to a user interface or image capture device (such as but not limited to a touch-screen or other pressure sensitive screen, or a camera), including any form of user interface configured for recording a user interaction. In other non-limiting examples, the user response recorded using the cognitive platform for tasks, such as but not limited to targeting and/or navigation and/or facial expression recognition or object recognition task(s), can include user actions that cause changes in a position, orientation, or movement of a computing device including the cognitive platform. Such changes in a position, orientation, or movement of a computing device can be recorded using an input device disposed in or otherwise coupled to the computing device, such as but not limited to a sensor. Non-limiting examples of sensors include a motion sensor, a position sensor, and/or an image capture device (such as but not limited to a camera).

In an example implementation involving multi-tasking tasks, the computing device is configured (such as using at least one specially-programmed processing unit) to cause the cognitive platform to present to a user two or more different types of tasks, such as but not limited to, targeting and/or navigation and/or facial expression recognition or object recognition tasks, during a short time frame (including in real-time and/or substantially simultaneously). The computing device is also configured (such as using at least one specially-programmed processing unit) to collect data indicative of the type of user response received to the multi-tasking tasks, within the short time frame (including in real-time and/or substantially simultaneously). In these examples, the two or more different types of tasks can be presented to the individual within the short time frame (including in real-time and/or substantially simultaneously), and the computing device can be configured to receive data indicative of the user response(s) relative to the two or more different types of tasks within the short time frame (including in real-time and/or substantially simultaneously).

In some examples, the short time frame (including substantially simultaneously) can be of any time interval at a resolution of up to about 1.0 millisecond or greater. The time intervals can be, but are not limited to, durations of time of any division of a periodicity of about 2.0 milliseconds or greater, up to any reasonable end time. The time intervals can be, but are not limited to, about 3.0 millisecond, about 5.0 millisecond, about 10 milliseconds, about 25 milliseconds, about 40 milliseconds, about 50 milliseconds, about 60 milliseconds, about 70 milliseconds, about 100 milliseconds, or greater. In other examples, the short time frame can be, but is not limited to, fractions of a second, about a second, between about 1.0 and about 2.0 seconds, or up to about 2.0 seconds, or more.

In some examples, the platform product or cognitive platform can be configured to collect data indicative of a reaction time of a user's response relative to the time of presentation of the tasks. For example, the computing device can be configured to cause the platform product or cognitive platform to provide smaller or larger reaction time window for a user to provide a response to the tasks as a way of adjusting the difficulty level.

In a non-limiting example implementation, the example platform product herein may be formed as, be based on, or be integrated with, an AKILI® platform product (also referred to herein as an "APP") by Akili Interactive Labs, Inc., Boston, Mass.

As used herein, the term "computerized stimuli or interaction" or "CSI" refers to a computerized element that is presented to a user to facilitate the user's interaction with a stimulus or other interaction. As non-limiting examples, the computing device can be configured to present auditory stimulus or initiate other auditory-based interaction with the user, and/or to present vibrational stimuli or initiate other vibrational-based interaction with the user, and/or to present tactile stimuli or initiate other tactile-based interaction with the user, and/or to present visual stimuli or initiate other visual-based interaction with the user.

Any task according to the principles herein can be presented to a user via a computing device, actuating component, or other device that is used to implement one or more stimuli or other interactive element. For example, the task can be presented to a user by rendering a user interface to present the computerized stimuli or interaction (CSI) or other interactive elements. In other examples, the task can be presented to a user as auditory, tactile, or vibrational computerized elements (including CSIs) using an actuating component. Description of use of (and analysis of data from) one or more CSIs in the various examples herein also encompasses use of (and analysis of data from) tasks including the one or more CSIs in those examples.

In an example where the computing device is configured to present visual CSI, the CSI can be rendered using at least one user interface to be presented to a user. In some examples, at least one user interface is configured for measuring responses as the user interacts with CSI computerized element rendered using the at least one user interface. In a non-limiting example, the user interface can be configured such that the CSI computerized element(s) are active, and may require at least one response from a user, such that the user interface is configured to measure data indicative of the type or degree of interaction of the user with the platform product. In another example, the user interface can be configured such that the CSI computerized element(s) are passive and are presented to the user using the at least one user interface but may not require a response from the user. In this example, the at least one user interface can be configured to exclude the recorded response of an interaction of the user, to apply a weighting factor to the data indicative of the response (e.g., to weight the response to lower or higher values), or to measure data indicative of the response of the user with the platform product as a measure of a misdirected response of the user (e.g., to issue a notification or other feedback to the user of the misdirected response).

In an example, the platform product can be configured as a processor-implemented system, method or apparatus that includes and at least one processing unit. In an example, the at least one processing unit can be programmed to render at least one user interface to present the computerized stimuli or interaction (CSI) or other interactive elements to the user for interaction. In other examples, the at least one processing unit can be programmed to cause an actuating component of the platform product to effect auditory, tactile, or vibrational computerized elements (including CSIs) to effect the stimulus or other interaction with the user. The at least one processing unit can be programmed to cause a component of the program product to receive data indicative of at least one user response based on the user interaction with the CSI or other interactive element (such as but not limited to cData), including responses provided using the input device. In an example where at least one user interface is rendered to present the computerized stimuli or interaction (CSI) or other interactive elements to the user, the at least one processing unit can be programmed to cause the user interface to receive the data indicative of at least one user response. The at least one processing unit also can be programmed to: analyze the cData to provide a measure of the individual's cognitive condition, and/or analyze the differences in the individual's performance based on determining the differences between the user's responses (including based on differences in the cData), and/or adjust the difficulty level of the auditory, tactile, or vibrational computerized elements (including CSIs), the CSIs or other interactive elements based on the analysis of the cData (including the measures of the individual's performance determined in the analysis), and/or provide an output or other feedback from the platform product that can be indicative of the individual's performance, and/or cognitive assessment, and/or response to cognitive treatment, and/or assessed measures of cognition. In non-limiting examples, the at least one processing unit also can be programmed to classify an individual as to amyloid group, and/or APOE expression group (or other expression group based on the expression level of other protein(s) that can be of clinical interest in a neurodegenerative condition), and/or potential efficacy of use of the cognitive platform or platform product when the individual is administered a drug, biologic or other pharmaceutical agent, and/or expected score from the individual's performance of a TOVA® test and/or a RAVLT™ test, based on the cData collected from the individual's interaction with the cognitive platform or platform product and/or metrics computed based on the analysis (and associated computations) of that cData. In non-limiting examples, the at least one processing unit also can be programmed to classify an individual as to likelihood of onset and/or stage of progression of a neurodegenerative condition, based on the cData collected from the individual's interaction with the cognitive platform or platform product and/or metrics computed based on the analysis (and associated computations) of that cData. The neurodegenerative condition can be, but is not limited to, Alzheimer's disease, dementia, Parkinson's disease, cerebral amyloid angiopathy, familial amyloid neuropathy, or Huntington's disease.

In other examples, the platform product can be configured as a processor-implemented system, method or apparatus that includes a display component, an input device, and the at least one processing unit. The at least one processing unit can be programmed to render at least one user interface, for display at the display component, to present the computerized stimuli or interaction (CSI) or other interactive elements to the user for interaction. In other examples, the at least one processing unit can be programmed to cause an actuating component of the platform product to effect auditory, tactile, or vibrational computerized elements (including CSIs) to effect the stimulus or other interaction with the user.

Non-limiting examples of an input device include a touch-screen, or other pressure-sensitive or touch-sensitive surface, a motion sensor, a position sensor, a pressure sensor, and/or an image capture device (such as but not limited to a camera).

The analysis of the individual's performance may include using the computing device to compute percent accuracy, number of hits and/or misses during a session or from a previously completed session. Other indicia that can be used to compute performance measures is the amount time the individual takes to respond after the presentation of a task (e.g., as a targeting stimulus). Other indicia can include, but are not limited to, reaction time, response variance, number of correct hits, omission errors, false alarms, learning rate, spatial deviance, subjective ratings, and/or performance threshold, etc.

In a non-limiting example, the user's performance can be further analyzed to compare the effects of two different types of tasks on the user's performances, where these tasks present different types of interferences (e.g., a distraction or an interruptor). The computing device is configured to present the different types of interference as CSIs or other interactive elements that divert the user's attention from a primary task. For a distraction, the computing device is configured to instruct the individual to provide a primary response to the primary task and not to provide a response (i.e., to ignore the distraction). For an interruptor, the computing device is configured to instruct the individual to provide a response as a secondary task, and the computing device is configured to obtain data indicative of the user's secondary response to the interruptor within a short time frame (including at substantially the same time) as the user's response to the primary task (where the response is collected using at least one input device). The computing device is configured to compute measures of one or more of a user's performance at the primary task without an interference, performance with the interference being a distraction, and performance with the interference being an interruption. The user's performance metrics can be computed based on these measures. For example, the user's performance can be computed as a cost (performance change) for each type of interference (e.g., distraction cost and interruptor/multi-tasking cost). The user's performance level on the tasks can be analyzed and reported as feedback, including either as feedback to the cognitive platform for use to adjust the difficulty level of the tasks, and/or as feedback to the individual concerning the user's status or progression.

In a non-limiting example, the computing device can also be configured to analyze, store, and/or output the reaction time for the user's response and/or any statistical measures for the individual's performance (e.g., percentage of correct or incorrect response in the last number of sessions, over a specified duration of time, or specific for a type of tasks (including non-target and/or target stimuli, a specific type of task, etc.).

In a non-limiting example, the computerized element includes at least one task rendered at a user interface as a visual task or presented as an auditory, tactile, or vibrational task. Each task can be rendered as interactive mechanics that are designed to elicit a response from a user after the user is exposed to stimuli for the purpose of cData and/or nData collection.

In a non-limiting example, the computerized element includes at least one platform interaction (gameplay) element of the platform rendered at a user interface, or as auditory, tactile, or vibrational element of a program product. Each platform interaction (gameplay) element of the platform product can include interactive mechanics (including in the form of videogame-like mechanics) or visual (or cosmetic) features that may or may not be targets for cData and/or nData collection.

As used herein, the term "gameplay" encompasses a user interaction (including other user experience) with aspects of the platform product.

In a non-limiting example, the computerized element includes at least one element to indicate positive feedback to a user. Each element can include an auditory signal and/or a visual signal emitted to the user that indicates success at a task or other platform interaction element, i.e., that the user responses at the platform product has exceeded a threshold success measure on a task or platform interaction (gameplay) element.

In a non-limiting example, the computerized element includes at least one element to indicate negative feedback to a user. Each element can include an auditory signal and/or a visual signal emitted to the user that indicates failure at a task or platform interaction (gameplay) element, i.e., that the user responses at the platform product has not met a threshold success measure on a task or platform interaction element.

In a non-limiting example, the computerized element includes at least one element for messaging, i.e., a communication to the user that is different from positive feedback or negative feedback.

In a non-limiting example, the computerized element includes at least one element for indicating a reward. A reward computer element can be a computer generated feature that is delivered to a user to promote user satisfaction with the CSIs and as a result, increase positive user interaction (and hence enjoyment of the user experience).

In a non-limiting example, the cognitive platform can be configured to render multi-task interactive elements. In some examples, the multi-task interactive elements are referred to as multi-task gameplay (MTG). The multi-task interactive elements include interactive mechanics configured to engage the user in multiple temporally-overlapping tasks, i.e., tasks that may require multiple, substantially simultaneous responses from a user.

In a non-limiting example, the cognitive platform can be configured to render single-task interactive elements. In some examples, the single-task interactive elements are referred to as single-task gameplay (STG). The single-task interactive elements include interactive mechanics configured to engage the user in a single task in a given time interval.

According to the principles herein, the term "cognition" or "cognitive" refers to the mental action or process of acquiring knowledge and understanding through thought, experience, and the senses. This includes, but is not limited to, psychological concepts/domains such as, executive function, memory, perception, attention, emotion, motor control, and interference processing. An example computer-implemented device according to the principles herein can be configured to collect data indicative of user interaction with a platform product, and to compute metrics that quantify user performance. The quantifiers of user performance can be used to provide measures of cognition (for cognitive assessment) or to provide measures of status or progress of a cognitive treatment.

According to the principles herein, the term "treatment" or "treat" refers to any manipulation of CSI in a platform product (including in the form of an APP) that results in a measurable change of the measures of cognitive abilities of a user, such as but not limited to improvements related to cognition, a user's mood, emotional state, and/or level of engagement or attention to the cognitive platform. The degree or level of change can be quantified based on user performance measures as describe herein. In an example, the term "treatment" may also refer to a therapy.

According to the principles herein, the term "session" refers to a discrete time period, with a clear start and finish, during which a user interacts with a platform product to receive assessment or treatment from the platform product (including in the form of an APP). A session can include two or more trials, including up to multiple trials.

According to the principles herein, the term "segment" refers to a portion of a trial that is less than the full trial.

According to the principles herein, the term "assessment" refers to at least one session of user interaction with CSIs or other feature or element of a platform product. The data collected from one or more assessments performed by a user using a platform product (including in the form of an APP) can be used as to derive measures or other quantifiers of cognition, or other aspects of a user's abilities.

According to the principles herein, the term "cognitive load" refers to the amount of mental resources that a user may need to expend to complete a task. This term also can be used to refer to the challenge or difficulty level of a task or gameplay.

In an example, the program platform includes a computing device that is configured to present to a user a cognitive platform based on interference processing. In an example system, method and apparatus that implements interference processing, at least one processing unit is programmed to render at least one first user interface or cause an actuating component to generate an auditory, tactile, or vibrational signal, to present first CSIs as a first task that requires a first type of response from a user. The example system, method and apparatus is also configured to cause the at least one processing unit to render at least one second user interface or cause the actuating component to generate an auditory, tactile, or vibrational signal, to present second CSIs as a first interference with the first task, requiring a second type of response from the user to the first task in the presence of the first interference. In a non-limiting example, the second type of response can include the first type of response to the first task and a secondary response to the first interference. In another non-limiting example, the second type of response may not include, and be quite different from, the first type of response. The at least one processing unit is also programmed to receive data indicative of the first type of response and the second type of response based on the user interaction with the platform product (such as but not limited to cData), such as but not limited to by rendering the at least one user interface to receive the data. The platform product also can be configured to receive nData indicative of measurements made before, during, and/or after the user interacts with the cognitive platform (including nData from measurements of physiological or monitoring components and/or cognitive testing components). The at least one processing unit also can be programmed to: analyze the cData and/or nData to provide a measure of the individual's condition (including physiological and/or cognitive condition), and/or analyze the differences in the individual's performance based on determining the differences between the measures of the user's first type and second type of responses (including based on differences in the cData) and differences in the associated nData. The at least one processing unit also can be programmed to: adjust the difficulty level of the first task and/or the first interference based on the analysis of the cData and/or nData (including the measures of the individual's performance and/or condition (including physiological and/or cognitive condition) determined in the analysis), and/or provide an output or other feedback from the platform product that can be indicative of the individual's performance, and/or cognitive assessment, and/or response to cognitive treatment, and/or assessed measures of cognition. In non-limiting examples, the at least one processing unit also can be programmed to classify an individual as to amyloid group, and/or APOE expression group (or other expression group based on the expression level of other protein(s) that can be of clinical interest in a neurodegenerative condition), and/or potential efficacy of use of the cognitive platform or platform product when the individual is administered a drug, biologic or other pharmaceutical agent, and/or expected score from the individual's performance of a TOVA® test and/or a RAVLT™ test, based on nData and the cData collected from the individual's interaction with the cognitive platform or platform product and/or metrics computed based on the analysis (and associated computations) of that cData and the nData. In non-limiting examples, the at least one processing unit also can be programmed to classify an individual as to likelihood of onset and/or stage of progression of a neurodegenerative condition, based on nData and the cData collected from the individual's interaction with the cognitive platform or platform product and/or metrics computed based on the analysis (and associated computations) of that cData and the nData. The neurodegenerative condition can be, but is not limited to, Alzheimer's disease, dementia, Parkinson's disease, cerebral amyloid angiopathy, familial amyloid neuropathy, or Huntington's disease.

In an example, the feedback from the differences in the individual's performance based on determining the differences between the measures of the user's first type and second type of responses and the nData can be used as an input in the cognitive platform that indicates real-time performance of the individual during one or more session(s). The data of the feedback can be used to as an input to a computation component of the computing device to determine a degree of adjustment that the cognitive platform makes to a difficulty level of the first task and/or the first interference that the user interacts within the same ongoing session and/or within a subsequently-performed session.

As a non-limiting example, the cognitive platform based on interference processing can be the Project: EVO™ platform by Akili Interactive Labs, Inc., Boston, Mass.

In an example system, method and apparatus according to the principles herein that is based on interference processing, the user interface is configured such that, as a component of the interference processing, one of the discriminating features of the targeting task that the user responds to is a feature in the platform that displays an emotion, a shape, a color, and/or a position that serves as an interference element in interference processing.

An example system, method, and apparatus according to the principles herein includes a platform product (which may include an APP) that is configured to set baseline metrics of CSI levels/attributes in APP session(s) based on measurements nData indicative of physiological condition and/or cognition condition (including indicators of neuropsychological disorders), to increase accuracy of assessment and efficiency of treatment. The CSIs may be used to calibrate a nData component to individual user dynamics of nData.

An example system, method, and apparatus according to the principles herein includes a platform product (which may include an APP) that is configured to use nData to detect states of attentiveness or inattentiveness to optimize delivery of CSIs related to treatment or assessment.

An example system, method, and apparatus according to the principles herein includes a platform product (which may include an APP) that is configured to use analysis of nData with CSI cData to detect and direct attention to specific CSIs related to treatment or assessment through subtle or overt manipulation of CSIs.

An example system, method, and apparatus according to the principles herein includes a platform product (which may include an APP) that is configured to use analysis of CSIs patterns of cData with nData within or across assessment or treatment sessions to generate user profiles (including profiles of ideal, optimal, or desired user responses) of cData and nData and manipulate CSIs across or within sessions to guide users to replicate these profiles.

An example system, method, and apparatus according to the principles herein includes a platform product (which may include an APP) that is configured to monitor nData for indicators of parameters related to user engagement and to optimize the cognitive load generated by the CSIs to align with time in an optimal engaged state to maximize neural plasticity and transfer of benefit resulting from treatment. As used herein, the term "neural plasticity" refers to targeted re-organization of the central nervous system. As a non-limiting example, an EEG measurement of the individual can be used to provide nData measures indicative of an attention of the individual as the individual interacts with the task and/or interference.

An example system, method, and apparatus according to the principles herein includes a platform product (which may include an APP) that is configured to monitor nData indicative of anger and/or frustration to promote continued user interaction (also referred to as "play") with the cognitive platform by offering alternative CSIs or disengagement from CSIs.

An example system, method, and apparatus according to the principles herein includes a platform product (which may include an APP) that is configured to change CSI dynamics within or across assessment or treatment sessions to optimize nData related to cognition or other physiological or cognitive aspects of the user.

An example system, method, and apparatus according to the principles herein includes a platform product (which may include an APP) that is configured to adjust the CSIs or CSI cognitive load if nData signals of task automation are detected, or the physiological measurements that relate to task learning show signs of attenuation.

An example system, method, and apparatus according to the principles herein includes a platform product (which may include an APP) that is configured to combine signals from CSI cData with nData to optimize individualized treatment promoting improvement of indicators of cognitive abilities, and thereby, cognition.

An example system, method, and apparatus according to the principles herein includes a platform product (which may include an APP) that is configured to use a profile of nData to confirm/verify/authenticate a user's identity.

An example system, method, and apparatus according to the principles herein includes a platform product (which may include an APP) that is configured to use nData to detect positive emotional response to CSIs in order to catalog individual user preferences to customize CSIs to optimize enjoyment and promote continued engagement with assessment or treatment sessions.

An example system, method, and apparatus according to the principles herein includes a platform product (which may include an APP) that is configured to generate user profiles of cognitive improvement (such as but not limited to, user profiles associated with users classified or known to exhibit improved working memory, attention, processing speed, and/or perceptual detection/discrimination), and deliver a treatment that adapts CSIs to optimize the profile of a new user as confirmed by profiles from nData.

An example system, method, and apparatus according to the principles herein includes a platform product (which may include an APP) that is configured to provide to a user a selection of one or more profiles configured for cognitive improvement.

An example system, method, and apparatus according to the principles herein includes a platform product (which may include an APP) that is configured to monitor nData from auditory and visual physiological measurements to detect interference from external environmental sources that may interfere with the assessment or treatment being performed by a user using an APP.

An example system, method, and apparatus according to the principles herein includes a platform product (which may include an APP) that is configured to use cData and/or nData (including metrics from analyzing the data) as a determinant or to make a decision as to whether a user (including a patient using a medical device) is likely to respond or not to respond to a treatment (such as but not limited to a cognitive treatment and/or a treatment using a biologic, a drug or other pharmaceutical agent). For example, the system, method, and apparatus can be configured to select whether a user (including a patient using a medical device) should receive treatment based on specific physiological or cognitive measurements that can be used as signatures that have been validated to predict efficacy of the cognitive platform in a given individual or certain individuals of the population (e.g., individual(s) classified to a given group based on amyloid status). Such an example system, method, and apparatus configured to perform the analysis (and associated computation) described herein can be used as a biomarker to perform monitoring and/or screening. As a non-limiting example, the example system, method and apparatus configured to provide a quantitative measure of the degree of efficacy of a cognitive treatment (including the degree of efficacy in conjunction with use of a biologic, a drug or other pharmaceutical agent) for a given individual or certain individuals of the population (e.g., individual(s) classified to a given group based on amyloid status). In some examples, the individual or certain individuals of the population may be classified as having a certain neurodegenerative condition.

An example system, method, and apparatus according to the principles herein includes a platform product (which may include an APP) that is configured to use nData to monitor a user's ability to anticipate CSI(s) and manipulate CSIs patterns and/or rules to disrupt user anticipation of response to CSIs, to optimize treatment or assessment in an APP.

Non-limiting examples of analysis (and associated computations) that can be performed based on various combinations of different types of nData and cData are described. The following example analyses and associated computations can be implemented using any example system, method and apparatus according to the principles herein.

In a non-limiting example, the example analyses (and associated computations) can be implemented by applying one or more ANCOVA (analysis of covariance) models to the data (including data and metrics derived from the cData and/or nData). ANCOVA provides a linear model that blends ANOVA and regression. As a non-limiting example, the analysis can be based on a covariate adjustment of comparisons of data between individuals using a single dependent variable or multiple variables.

In a non-limiting example, the example analyses (and associated computations) can be implemented by applying one or more linear mixed model regression models to the data (including data and metrics derived from the cData and/or nData). As a non-limiting example, the analysis can be based on a covariate adjustment of comparisons of data for given individuals, i.e., an analysis of factors with multiple measurements (usually longitudinal) for each individual. As a non-limiting example, the analysis can be configured to account for the correlation between measurements, since the data originates from the same source. In this example as well, the analysis can be based on a covariate adjustment of comparisons of data between individuals using a single dependent variable or multiple variables.

Table 1 shows non-limiting examples of the combinations of the various types of collected data (cData and/or nData) that can be used in the data analysis (and associated computations) described herein. Table 1 also shows non-limiting examples of the types of metrics that can result from the data analysis performed using the various combinations of the collected data (labeled impl. 1 through 6). According to the principles herein, the data and analysis of any one or more of impl. 1 through 6 can be used to train a predictive model as a biomarker or other marker of a likelihood of onset of a neurodegenerative condition and/or a stage of progression of the neurodegenerative condition. The trained predictive model can be used to provide a scoring that serves as a marker (including as a biomarker) of an amyloid status (A+ or A−) or a level of expression of APOE protein, which can provide an indication of the likelihood of onset of a neurodegenerative condition of the individual and/or the stage of progression of the neurodegenerative condition.

challenge session and/or the second challenge session, and/or during the first training session and/or the second training session. For one or more of the sessions (i.e., one or more challenge sessions, and/or assessment sessions, and/or training sessions), the example cognitive platform or platform product can be configured to present computerized tasks and platform interactions that inform cognitive assessment (screening or monitoring) or deliver treatment. The tasks can be single-tasking tasks and/or multi-tasking tasks. One or more of the tasks can include CSIs.

In the non-limiting example of Impl. 1 (and any other example implementation herein), the initial assessment session can include an interaction of the individual with a primary task in the absence of and in the presence of an interference, with the at least one indicator being computed based on the data indicating the response of the individual to the primary task and/or the interference. The first challenge session can include two or more interactions of the individual with a primary task in the absence of and in the presence of an interference, with the difficulty level of the task and/or the interference being adjusted prior to the individual's interaction with the second or later instances of the primary task and/or the interference, and with the at least one indicator being computed based on the data indicating the response of the individual to the two or more instances of the primary task and/or the interference. Each of the first training session and the second training session can involve multiple interactions of the individual with the primary task in the absence of and in the presence of an interference, with the difficulty level of the primary task and/or the interference being adjusted prior to the individual's interaction with two or more of the multiple instances (including second instances, third instances, and more instances) of the primary task and/or the interference, and with the at least one

TABLE 1

| | cData | nData | | | | | | | | |
|---|---|---|---|---|---|---|---|---|---|---|
| Analysis | Cognitive Platform Data | Amyloid Status | Drug[†] Group | Age | Gender | Amyloid Level Data | APOE Expression | TOVA ® | RAVLT ™ | fMRI[‡] |
| Impl. 1 | X | X | | X | X | X | X | | | X |
| Impl. 2 | X | X | | X | X | X | X | | | X |
| Impl. 3 | X | X | | X | X | | X | X | X | X |
| Impl. 4 | X | X | | X | X | | X | | | X |
| Impl. 5 | X | | | X | X | X | | | | X |
| Impl. 6 | X | X | X | X | X | | X | | | X |

[†]Drug encompasses biologics and/or other pharmaceutical agents
[‡]measures such as cortical thickness, brain functional activity changes, or other measure In each example implementation (including Impl. 1 through 6), the cData is obtained based on interactions of each individual with any one or more of the example cognitive platforms and/or platform products described herein.

In a non-limiting example implementation, the cData used can be derived as described herein using an example cognitive platform or platform product that is configured to implement a sequence that could include at least one initial assessment session, a first challenge session, a first training session, a second training session, and a second challenge session. The cData is collected based on measurements of the responses of the individual with the example cognitive platform or platform product during one or more segments of the sequence. For example, the cData can include data collected by the cognitive platform or platform product to quantify the interaction of the individual with the first indicator being computed based on at least a portion of the data indicating the responses of the individual to the multiple instances of the primary task and/or the interference. Similarly to the first challenge session, the second challenge session can include two or more interactions of the individual with a primary task in the absence of and in the presence of an interference, with the difficulty level of the task and/or the interference being adjusted prior to the individual's interaction with the second or later instances of the primary task and/or the interference, and with the at least one indicator being computed based on the data indicating the response of the individual to the two or more instances of the primary task and/or the interference.

Non-limiting examples of the types of cData that can be derived from the interactions of an individual with the cognitive platform or platform product are as follows. The cData can be one or more scores generated by the cognitive platform or platform product based on the individual's response(s) in performance of a single-tasking task presented by the cognitive platform or platform product. The single-tasking task can be, but is not limited to, a targeting task, a navigation task, a facial expression recognition task, or an object recognition task. The cData can be one or more scores generated by the cognitive platform or platform product based on the individual's response(s) in performance of a multi-tasking task presented by the cognitive platform or platform product. The multi-tasking task can include a targeting task and/or a navigation task and/or a facial expression recognition task and/or an object recognition task, where one or more of the multi-tasking tasks can be presented as an interference or with one or more primary tasks. The cData collected can be a scoring representative of the individual's response(s) to each task of the multi-task task(s) presented, and/or combination scores representative of the individual's overall response(s) to the multi-task task(s). The combination score can be derived based on computation using any one or more of the scores collected from the individual's response(s) to each task of the multi-task task(s) presented. such as but not limited to a mean, mode, median, average, difference (or delta), standard deviation, or other type of combination. In a non-limiting example, the cData can include measures of the individual's reaction time to one or more of the tasks. The cData can be generated based on an analysis (and associated computation) performed using the other cData collected or derived using the cognitive platform or platform product. The analysis can include computation of an interference cost or other cost function. The cData can also include data indicative of an individual's compliance with a pre-specified set and type of interactions with the cognitive platform or platform product, such as but not limited to a percentage completion of the pre-specified set and type of interactions. The cData can also include data indicative of an individual's progression of performance using the cognitive platform or platform product, such as but not limited to a measure of the individual's score versus a pre-specified trend in progress.

In Impl. 1 and any other implementation, the interference cost may be computed, in a non-limiting example, as the percentage change based on the difference in the individual's response from a task performed without interference and the task performed with interference. In a non-limiting example, the interference cost can be computed such that greater magnitudes of values indicate increased amount of interference when the individual is interacting the task simultaneously with the interference.

In the non-limiting example implementations, the cData can be collected from a user interaction with the example cognitive platform or platform product at one or more specific timepoints: an initial timepoint (T1), and/or at a second timepoint (T2), and/or at a third timepoint (T3). As non-limiting examples, the measurement timepoints T2 and T1 can be separated by 5 minutes, about 7 minutes, about 15 minutes, about 1 hour, about 12 hours, about 1 day, about 5 days, about 10 days, about 15 days, about 20 days, about 28 days, about a month, or more. As non-limiting examples, the measurement timepoints T3 and T2 can be separated by 5 minutes, about 7 minutes, about 15 minutes, about 1 hour, about 12 hours, about 1 day, about 5 days, about 10 days, about 15 days, about 20 days, about 28 days, about a month, or more.

In the non-limiting example implementations, the example cognitive platform or platform product can be configured for interaction with the individual over multiple different sessions. In an example, the cData can be collected at timepoint T1 and/or timepoint T2 and/or timepoint T3 based on the interactions of the individual with the multiple different sessions during either (i) the time period between timepoint T1 and timepoint T2; or (ii) the time period between timepoint T2 and timepoint T3; or during both (i) and (ii). For one or more of these multiple different sessions, the example cognitive platform or platform product can be configured for screening, for monitoring, and/or for treatment, as described in the various examples herein.

In a non-limiting example implementation, the example analyses (and associated computations) can be implemented based at least in part on the cData and the nData indicated in columns labeled with a "X" in the row labeled Impl. 1. In this example, the nData measured for each individual includes data indicative of amyloid status, age, gender, amyloid level, APOE level, and fMRI measures (e.g., cortical thickness, or brain functional activity changes). As described in greater detail below, the nData can be collected during a particular time period relative to the time period in which the cData are collected, so that the nData can correlate to the cData. For example, the nData can be collected during one or more timepoints, or during one or more time periods. The cData can be collected during one or more timepoints, or during one or more time periods. The timepoints or time periods during which the nData are collected can be before, overlap, or be after the timepoints or time period during which the cData are collected. The results of these example analyses (and associated computations) can be used to provide data indicative of amyloid baseline effects in individuals of the population that are assigned to a given group (e.g., group classification based on amyloid status). These example analyses can be performed using measured cData from the individual's interaction with the cognitive platform or the platform product (such as but not limited to the challenge metrics (i.e., computed from the cData collected in a challenge session) and/or the training metrics (i.e., computed from the cData collected in a training session) (including training compliance and/or progress metrics)) at single time points. The results of these example analyses (and associated computations) can be used to provide data indicative of differences between the individuals of the group with an amyloid positive (A+) status and the individuals of the group with an amyloid negative (A−) status. An example system, method and apparatus configured to perform the analysis (and associated computation) can be configured to implement a predictive model (such as but not limited to a classifier model) to designate individuals of the population as having an amyloid positive (A+) status or an amyloid negative (A−) status.

In the non-limiting example of Impl. 1, the analysis (and associated computation) that can be performed using the cData and nData is described. Differing analysis models can be applied to data collected from user interactions with the cognitive platform or the platform product (cData) collected at initial timepoint (T1) and at second timepoint (T2). The analysis model can be based on an ANCOVA model and/or a linear mixed model regression model, applied to a restricted data set (based on age and gender nData) or a larger data set (based on age, gender, APOE expression group, fMRI, and other nData).

In the non-limiting example of Impl. 1, the analysis (and associated computation) can be performed based on cData collected from at least one of the first challenge segment, the first training session, the second training session, or the second challenge session, generated based on the individual's interactions with the cognitive platform or the platform product. The example cognitive platform or the platform product can be configured to implement tasks involving single-tasking tasks and/or multi-tasking tasks. The example analysis (and associated computation) also can be performed by comparing the effects of group classification (such as but not limited to grouping based on amyloid status) between individuals, where each variable is examined as a dependent variable with the group classification as a factor along with the covariate set (i.e., set of variables found to co-vary or otherwise correlates with the parameter of interest). The example analysis (and associated computation) also can be performed by comparing the effects of a group classification versus the individual's interactions with the tasks of the cognitive platform or the platform product, where the cData is data collected based on the tasks of the first challenge session and/or the second challenge session (from performance of single-tasking tasks and/or multi-tasking tasks). The example analysis (and associated computation) also can be performed by comparing effects of group classification (such as but not limited to grouping based on amyloid status) versus order Interactions, where the cData is collected from first challenge session and/or the second challenge session (from performance of single-tasking tasks and/or multi-tasking tasks), and the first training session and/or the second training session. The example analysis (and associated computation) also can be performed by comparing effects of group classification (such as but not limited to grouping based on amyloid status) versus order Interactions and the individual's interactions with the tasks of the cognitive platform or the platform product, where the cData is collected from first challenge session and/or the second challenge session (from performance of single-tasking tasks and/or multi-tasking tasks).

In the non-limiting example of Impl. 1, the analysis (and associated computation) can be performed to determine a measure of the sensitivity and specificity of the cognitive platform or the platform product to serve as a biomarker or other marker to identify and classify the individuals of the population that have an amyloid positive (A+) status, based on applying a logistic regression model to the data collected (including the cData and/or the nData).

In the non-limiting example of Impl. 1, the analysis (and associated computation) can be performed to determine a measure of the sensitivity and specificity of the cognitive platform or the platform product to serve as a biomarker or other marker to identify and classify the individuals of the population according to APOE expression group (or other expression group based on the expression level of other protein(s) that can be of clinical interest in a neurodegenerative condition), based on applying a logistic regression model to the data collected (including the cData and/or the nData), including the amyloid level data.

In this example implementation, certain cData collected from the individual's interaction with the tasks (and associated CSIs) presented by the cognitive platform or platform product, and/or metrics computed using the cData based on the analysis (and associated computations) described, can co-vary or otherwise correlate with the nData, such as but not limited to amyloid group and/or APOE expression group (or other expression group based on the expression level of other protein(s) that can be of clinical interest in a neurodegenerative condition). An example cognitive platform or platform product according to the principles herein can be configured to classify an individual as to amyloid group and/or APOE expression group (or other expression group based on the expression level of other protein(s) that can be of clinical interest in a neurodegenerative condition) based on the cData collected from the individual's interaction with the cognitive platform or platform product and/or metrics computed based on the analysis (and associated computations). The example cognitive platform or platform product can include, or communicate with, a machine learning tool or other computational platform that can be trained using the cData and metrics of Impl. 1 to perform the classification.

As a non-limiting example, a machine learning tool can train a predictive model using a set of training data (training dataset) that includes the cData and metrics of Impl. 1 (or any other implementation described herein) collected from a first population of one or more individual users (e.g., 10 users, 100 users, 1000 users, 10,000 users, or more users). The predictive model can then be applied to either cData collected from one of the first population of users, or cData collected from a user that is not included in the first population of users, in order to provide the scoring output for the individual.

In a non-limiting example implementation, the example analyses (and associated computations) can be implemented based at least in part on the cData and the nData indicated in columns labeled with a "X" in the row labeled Impl. 2. Similarly to Impl. 1, in the example of Impl. 2, the nData measured for each individual includes data indicative of amyloid status, age, gender, amyloid level, APOE expression group, and fMRI measures (e.g., cortical thickness, or brain functional activity changes). The results of these example analyses (and associated computations) can be used to provide data indicative of the effects over time of the presence of amyloid in the populations of individuals. These example analyses can be performed using measured cData from the individual's interaction with the cognitive platform or the platform product (such as but not limited to the challenge metrics (i.e., computed from the cData collected in a challenge session) and/or the training metrics (i.e., computed from the cData collected in a training session) (including training compliance and/or progress metrics)) over various periods of time. The results of these example analyses (and associated computations) can be used to provide data indicative of differences between the individuals of the population with an amyloid positive (A+) status and the individuals of the population with an amyloid negative (A−) status. An example system, method and apparatus configured to perform the analysis (and associated computation) can be configured to implement a predictive model to designate individuals of the population as having an amyloid positive (A+) status or an amyloid negative (A−) status.

In the non-limiting example of Impl. 2, the analysis (and associated computation) that can be performed using the cData and nData is described. Differing analysis models can be applied to data collected from user interactions with the cognitive platform or the platform product (cData) collected at an initial timepoint (T1), and/or at a second timepoint (T2), and/or at a third timepoint (T3). The analysis model can be based on an ANCOVA model and/or a linear mixed model regression model, applied to a restricted data set (based on age and gender nData) or a larger data set (based on age, gender, APOE expression group, fMRI, and other nData).

In the non-limiting example of Impl. 2, the analysis (and associated computation) can be performed based on cData collected from at least one of the first challenge segment or the second challenge session, generated based on cData measured before and/or after the individual performs multiple sessions (over a period of time) with the cognitive platform or the platform product. The period of time can be the time interval between T1 and T2 and/or the time interval between T2 and T3.

The example analysis (and associated computation) can be performed based on a comparison of the change (delta) in data collected at timepoint T1 versus timepoint T2 to the change (delta) in data collected at timepoint T3 versus timepoint T2. The example analysis (and associated computation) also can be performed based on data collected at timepoint T1 versus timepoint T3. The example analysis (and associated computation) also can be performed based on data collected at timepoint T2 versus timepoint T3. The example analysis (and associated computation) also can be performed based on data collected at timepoint T1 versus timepoint T2. The example analysis (and associated computation) also can be performed using data collected based on the tasks of the first challenge session and/or the second challenge session at specified achievement level.

The example analysis (and associated computation) can be performed by comparing effects of group classification (such as but not limited to grouping based on amyloid status) between individuals, by computing a score representative of the difference in performance of the individual between different timepoints (i.e., prior to and after training sessions) using the cognitive platform or platform product (including difference in cData), for each variable with the group classification as a factor along with the covariate set. The example analysis (and associated computation) also can be performed by comparing a score representative of the difference in performance of the individual between different timepoints (i.e., prior to and after training sessions) using the cognitive platform or platform product (including difference in cData) within specified groupings for each variable using any example model described herein (including covariate sets) for the nData corresponding to the individuals of the amyloid positive (A+) groups and the individuals of the amyloid negative (A−) groups separately. The example analysis (and associated computation) also can be performed by comparing the effect of the sessions (and associated tasks) presented to the individual for interaction using the cognitive platform or the platform product, where the cData (from performance of single-tasking tasks and/or multi-tasking tasks) are compared to determine the effect of the sessions on the individuals' performance. The example analysis (and associated computation) also can be performed by comparing the effect of the sessions (and associated tasks) presented to the individual for interaction using the cognitive platform or the platform product, where the cData (from performance of single-tasking tasks and/or multi-tasking tasks) are compared to determine the effect of the sessions versus type of task (e.g., singletasking versus multitasking) on the individuals' performance. In this example, the rate and/or type of change of the scores for an individual's performance prior to and after training sessions using the cognitive platform or platform product can be quantified and monitored. The example analysis (and associated computation) also can be performed by comparing effects of group classification (such as but not limited to grouping based on amyloid status) versus session interactions, where the cData (from performance of single-tasking tasks and/or multi-tasking tasks) are compared to determine the effect of the group classification versus sessions on the individuals' performance. In this example, the differences of the scores for the performance of individual in differing groups (e.g., as grouped according to amyloid status) using the cognitive platform or platform product can be quantified and monitored. The example analysis (and associated computation) also can be performed by comparing effects of group classification (such as but not limited to grouping based on amyloid status) versus sessions and type of task interactions, where the cData (from performance of single-tasking tasks and/or multi-tasking tasks) are compared to determine the effect of the group classification versus sessions and type of task on the individuals' performance. In this example, the rate and/or type of change of the scores for the individual's performance prior to and after training sessions using the cognitive platform or platform product can be quantified and monitored, based on the types of tasks the individual performs (e.g., singletasking versus multitasking).

In the non-limiting example of Impl. 2, the analysis (and associated computation) can be performed to determine a measure of the sensitivity and specificity of the cognitive platform or the platform product to serve as a biomarker or other marker to identify and classify the individuals of the population that have an amyloid positive (A+) status, based on applying a predictive model (such as but not limited to a logistic regression model) to the data collected (including the cData and/or the nData) from the individual's interaction with the cognitive platform or the platform product both prior to and after the individual performs one or more training sessions using the cognitive platform or the platform product.

In the non-limiting example of Impl. 2, the analysis (and associated computation) can be performed to determine a measure of the sensitivity and specificity of the cognitive platform or the platform product to serve as a biomarker or other marker to identify and classify the individuals of the population according to APOE expression group (or other expression group based on the expression level of other protein(s) that can be of clinical interest in a neurodegenerative condition) as a grouping variable, based on applying a logistic regression model to the data collected (including the cData and/or the nData), including the amyloid level data. In this example, the sensitivity and specificity of the cognitive platform or platform product to serve as a biomarker or other marker can be computed using an analytical tool, such as but not limited to a receiver operator characteristic (ROC) analysis.

In this example implementation, certain cData collected from the individual's interaction with the tasks (and associated CSIs) presented by the cognitive platform or platform product, and/or metrics computed using the cData based on the analysis (and associated computations) described, can co-vary or otherwise correlate with the nData, such as but not limited to amyloid group and/or APOE expression group (or other expression group based on the expression level of other protein(s) that can be of clinical interest in a neurodegenerative condition). An example cognitive platform or platform product according to the principles herein can be configured to classify an individual as to amyloid group and/or APOE expression group (or other expression group based on the expression level of other protein(s) that can be of clinical interest in a neurodegenerative condition) based on the cData collected from the individual's interaction with the cognitive platform or platform product and/or metrics computed based on the analysis (and associated computations). The example cognitive platform or platform product can include, or communicate with, a machine learning tool or other computational platform that can be trained using the cData and metrics of Impl. 2 to perform the classification.

In a non-limiting example implementation, the example analyses (and associated computations) can be implemented based at least in part on the cData and the nData indicated in columns labeled with a "X" in the row labeled Impl. 3. In the example of Impl. 3, the nData measured for each individual includes data indicative of amyloid status, age, gender, APOE expression group, and fMRI measures (e.g., cortical thickness, or brain functional activity changes). The results of these example analyses (and associated computations) can be used to provide data and metrics indicative of the effects of the training sessions on the individual's performance. These example analyses can be performed using measured cData from the individual's interaction with the cognitive platform or the platform product (such as but not limited to the challenge metrics (i.e., computed from the cData collected in a challenge session) and/or the training metrics (i.e., computed from the cData collected in a training session) (including training compliance and/or progress metrics)) and measured nData (such as but not limited to at least one score from the individual's performance of at least one TOVA® test and/or at least one RAVLT™ test). The example training metrics can be used as a continuous predictor (including using a trained predictive model to generate a continuous scoring output) of the desired score of performance, such as but not limited to a score on a TOVA® test and/or a RAVLT™ test. An example system, method and apparatus configured to perform the analysis (and associated computation) can be used to generate an indicator that can be used as a biomarker to provide a scoring of (including to classify) an individual of the population as to a given group (e.g., based on amyloid status), based on measured data over time representative of an individual's performance using the cognitive platform or platform product. The measured data can include data prior to and after one or more training sessions using the cognitive platform or platform product.

In the non-limiting example of Impl. 3, the analysis (and associated computation) that can be performed using the cData and nData is described. Differing analysis models can be applied to data collected from user interactions with the cognitive platform or the platform product (cData) collected at an initial timepoint (T1), and/or at a second timepoint (T2), and/or at a third timepoint (T3). The analysis model can be based on an ANCOVA model and/or a linear mixed model regression model, applied to a restricted data set (based on age and gender nData) or a larger data set (based on age, gender, APOE expression group, fMRI, and other nData).

In the non-limiting example of Impl. 3 (and any other example implementation herein), each timepoint is an instance of time. As a non-limiting example, timepoint T1 can be at time t=0, while timepoint T2 can be t=5 minutes, while timepoint T3 can be t=20 minutes. In another example, The analysis models can be applied to data collected from user interactions with the cognitive platform or the platform product (cData) over two or more time intervals between the initial timepoint (T1) and the second timepoint (T2), and/or over two or more time intervals between the second timepoint (T2) and the third timepoint (T3), and/or over two or more time intervals between the first timepoint (T1) and the third timepoint (T3).

In the non-limiting example of Impl. 3, the analysis (and associated computation) can be performed based on cData collected from at least one of the first challenge segment or the second challenge session, generated based on cData measured before and/or after the individual performs multiple different sessions (over a period of time) with the cognitive platform or the platform product. The interactions with the multiple different session can be performed during the time period between timepoints T2 and T3.

The example analysis (and associated computation) can be performed by comparing scores for the individual's performance prior to and after training sessions using the cognitive platform or platform product for each variable using any example model described herein for the nData corresponding to the individuals of the amyloid positive (A+) groups and the individuals of the amyloid negative (A−) groups separately. The example analysis (and associated computation) also can be performed by comparing the effect of the sessions (and associated tasks) presented to the individual for interaction using the cognitive platform or the platform product, where the cData (from performance of single-tasking tasks and/or multi-tasking tasks) are compared to determine the efficacy of the sessions on individuals in the population. The example analysis (and associated computation) also can be performed by comparing effects of group classification (such as but not limited to grouping based on amyloid status) versus session interactions, where the cData (from performance of single-tasking tasks and/or multi-tasking tasks) are compared to determine the efficacy of the group classification versus sessions on the individuals' performance. The example analysis (and associated computation) also can be performed by comparing effects of group classification (such as but not limited to grouping based on amyloid status) versus sessions and type of task interactions, where the cData (from performance of single-tasking tasks and/or multi-tasking tasks) are compared to determine the effect of the group classification versus sessions and type of task on the individuals' performance.

In this example implementation, certain cData collected from the individual's interaction with the tasks (and associated CSIs) presented by the cognitive platform or platform product, and/or metrics computed using the cData based on the analysis (and associated computations) described, can co-vary or otherwise correlate with the nData, such as but not limited to amyloid group and/or APOE expression group (or other expression group based on the expression level of other protein(s) that can be of clinical interest in a neurodegenerative condition) and/or expected score from the individual's performance of a TOVA® test and/or a RAVLT™ test. An example cognitive platform or platform product according to the principles herein can be configured to classify an individual as to amyloid group and/or APOE expression group (or other expression group based on the expression level of other protein(s) that can be of clinical interest in a neurodegenerative condition) and/or expected score from the individual's performance of a TOVA® test and/or a RAVLT™ test based on the cData collected from the individual's interaction with the cognitive platform or platform product and/or metrics computed based on the analysis (and associated computations). The example cognitive platform or platform product can include, or communicate with, a machine learning tool or other computational platform that can be trained using the cData and metrics of Impl. 3 to perform the classification.

In a non-limiting example implementation, the example analyses (and associated computations) can be implemented based at least in part on the cData and the nData indicated in columns labeled with a "X" in the row labeled Impl. 4. In the example of Impl. 4, the nData measured for each individual includes data indicative of amyloid status, age, gender, APOE expression group, and fMRI measures (e.g., cortical thickness, or brain functional activity changes). The results of these example analyses (and associated computations) can be used to provide data and metrics indicative of the effects over time of the training sessions as an indicator of the amyloid positive (A+) or the amyloid negative (A−) status of individuals of the population. These example analyses can be performed using measured cData from the individual's interaction with the cognitive platform or the platform product (such as but not limited to the challenge metrics (i.e., computed from the cData collected in a challenge session) and/or the training metrics (i.e., computed from the cData collected in a training session) (including training compliance and/or progress metrics)). The example training metrics can be used to compute compliance and/or progress metrics at regular time intervals, such as but not limited to at the end of each week that the individual interacts with the cognitive platform or the platform product. An example system, method and apparatus configured to perform the analysis (and associated computation) can be configured to implement a predictive model of individuals of the population as to differences in the training sessions over time.

In the non-limiting example of Impl. 4, the analysis (and associated computation) that can be performed using the cData and nData is described. Differing analysis models can be applied to data collected from user interactions with the cognitive platform or the platform product (cData) collected at an initial timepoint (T1), and/or at a second timepoint (T2), and/or at a third timepoint (T3). The analysis model can be based on an ANCOVA model and/or a linear mixed model regression model, applied to a restricted data set (based on age and gender nData) or a larger data set (based on age, gender, APOE expression group, fMRI, and other nData).

In the non-limiting example of Impl. 4, the analysis (and associated computation) can be performed based on cData collected from at least one of the first challenge segment or the second challenge session, generated based on cData measured before and/or after the individual performs multiple different sessions (over a period of time) with the cognitive platform or the platform product. The interactions with the multiple different session can be performed during the time period between timepoints T2 and T3.

The example analysis (and associated computation) can be performed by comparing scores for the individual's performance prior to and after training sessions using the cognitive platform or platform product for each variable using any example model described herein for the nData corresponding to the individuals of the amyloid positive (A+) groups and the individuals of the amyloid negative (A−) groups separately. The example analysis (and associated computation) also can be performed to determine mean differences between scores from different groups, e.g., where the cData are compared to determine differences between amyloid positive (A+) and amyloid negative (A−) individuals of the population (as an indicator of amyloid group). The example analysis (and associated computation) also can be performed by comparing trends in a linear regression models of the effect of the sessions (and associated tasks) presented to the individual for interaction using the cognitive platform or the platform product, where the cData are compared to determine differences between amyloid positive (A+) and amyloid negative (A−) individuals of the population (as an indicator of amyloid group). The example analysis (and associated computation) also can be performed by comparing effects of group classification (such as but not limited to grouping based on amyloid status) versus session interactions, where the cData are compared to determine differences between amyloid positive (A+) and amyloid negative (A−) individuals of the population (as an indicator of amyloid group).

In this example implementation, certain cData collected from the individual's interaction with the tasks (and associated CSIs) presented by the cognitive platform or platform product, and/or metrics computed using the cData based on the analysis (and associated computations) described, can co-vary or otherwise correlate with the nData, such as but not limited to amyloid group and/or APOE expression group (or other expression group based on the expression level of other protein(s) that can be of clinical interest in a neurodegenerative condition). An example cognitive platform or platform product according to the principles herein can be configured to classify an individual as to amyloid group and/or APOE expression group (or other expression group based on the expression level of other protein(s) that can be of clinical interest in a neurodegenerative condition) based on the cData collected from the individual's interaction with the cognitive platform or platform product and/or metrics computed based on the analysis (and associated computations). The example cognitive platform or platform product can include, or communicate with, a machine learning tool or other computational platform that can be trained using the cData and metrics of Impl. 4 to perform the classification.

In a non-limiting example implementation, the example analyses (and associated computations) can be implemented based at least in part on the cData and the nData indicated in columns labeled with a "X" in the row labeled Impl. 5. In the example of Impl. 5, the nData measured for each individual includes data indicative of amyloid levels, age, gender, and fMRI measures (e.g., cortical thickness, or brain functional activity changes). The results of these example analyses (and associated computations) can be used to provide data and metrics indicative of the effects of the sessions with the cognitive platform or platform product as an indicator of the amyloid levels and fMRI cortical thickness (or other fMRI measures) of individuals of the population. These example analyses can be performed using measured cData from the individual's interaction with the cognitive platform or the platform product (such as but not limited to the challenge metrics (i.e., computed from the cData collected in a challenge session) and/or the training metrics (i.e., computed from the cData collected in a training session) (including training compliance and/or progress metrics)). An example system, method and apparatus configured to perform the analysis (and associated computation) can be configured to implement a predictive model of individuals of the population as to differences in amyloid levels and/or cortical thickness (or other property measurable using fMRI).

In the non-limiting example of Impl. 5, the analysis (and associated computation) that can be performed using the cData and nData is described. Differing analysis models can be applied to data collected from user interactions with the cognitive platform or the platform product (cData) collected at an initial timepoint (T1), and/or at a second timepoint (T2), and/or at a third timepoint (T3). The analysis model can be based on an ANCOVA model and/or a linear mixed model regression model, applied to a restricted data set (based on age and gender nData) or a larger data set (based on age, gender, APOE expression group, fMRI, and other nData).

In the non-limiting example of Impl. 5, the analysis (and associated computation) can be performed based on cData collected from at least one of the first challenge segment or the second challenge session, generated based on cData measured before and/or after the individual performs multiple different sessions (over a period of time) with the cognitive platform or the platform product. The interactions with the multiple different session can be performed during the time period between timepoints T2 and T3.

The example analysis (and associated computation) can be performed by comparing individual's performance on the cognitive platform or platform product as an indicator of the individual's amyloid levels and/or cortical thickness (or other property measurable using fMRI).

In this example implementation, certain cData collected from the individual's interaction with the tasks (and associated CSIs) presented by the cognitive platform or platform product, and/or metrics computed using the cData based on the analysis (and associated computations) described, can co-vary or otherwise correlate with the nData, such as but not limited to amyloid level. An example cognitive platform or platform product according to the principles herein can be configured to classify an individual as to amyloid level based on the cData collected from the individual's interaction with the cognitive platform or platform product and/or metrics computed based on the analysis (and associated computations). The example cognitive platform or platform product can include, or communicate with, a machine learning tool or other computational platform that can be trained using the cData and metrics of Impl. 5 to perform the classification.

In a non-limiting example implementation, the example analyses (and associated computations) can be implemented based at least in part on the cData and the nData indicated in columns labeled with a "X" in the row labeled Impl. 6. In the example of Impl. 6, the nData measured for each individual includes data indicative of amyloid status, drug group, age, gender, APOE expression group, and fMRI measures (e.g., cortical thickness, or brain functional activity changes). In any example herein, the "drug group" is specified based on the amount, concentration, or dose titration of the drug being or to be administered to an individual. The results of these example analyses (and associated computations) can be used to provide data and metrics indicative of the effects of the active drug used in a given drug group on the individual's performance using the cognitive platform or platform product. These example analyses can be performed using measured cData from the individual's interaction with the cognitive platform or the platform product (such as but not limited to the challenge metrics (i.e., computed from the cData collected in a challenge session) and/or the training metrics (i.e., computed from the cData collected in a training session) (including training compliance and/or progress metrics)) and measured nData (such as but not limited to amyloid status, drug group, age, gender, APOE expression group, and fMRI measures (e.g., cortical thickness, or brain functional activity changes)). An example system, method and apparatus configured to perform the analysis (and associated computation) described herein can be used as a biomarker for monitoring and/or screening. As a non-limiting example, the example system, method and apparatus configured to provide a quantitative measure of the degree of efficacy of a cognitive treatment (including the degree of efficacy in conjunction with use of a biologic, a drug or other pharmaceutical agent) for a given individual or certain individuals of the population (e.g., individual(s) classified to a given group based on amyloid status).

In the non-limiting example of Impl. 6, the analysis (and associated computation) that can be performed using the cData and nData is described. Differing analysis models can be applied to data collected from user interactions with the cognitive platform or the platform product (cData) collected at an initial timepoint (T1), and/or at a second timepoint (T2), and/or at a third timepoint (T3). The analysis model can be based on an ANCOVA model and/or a linear mixed model regression model, applied to a restricted data set (based on age and gender nData) or a larger data set (based on age, gender, APOE expression group, fMRI, and other nData).

In the non-limiting example of Impl. 6, the analysis (and associated computation) can be performed based on cData collected from at least one of the first challenge session or the second challenge session and/or at least one of the first training session or the second challenge session, generated based on cData measured before and/or after the individual performs multiple different sessions (over a period of time) with the cognitive platform or the platform product. The cData can be collected based on the sessions performed by the individual before administration of the drug is administered and/or after administration of the drug. The interactions with the multiple different session can be performed during the time period between timepoints T2 and T3.

The example analysis (and associated computation) can be performed by comparing each variable using any example model described herein for the nData corresponding to the drug group along with a covariate set. The example analysis (and associated computation) also can be performed by comparing effects of group classification (such as but not limited to grouping based on amyloid status) versus drug interactions, where the cData (from performance of single-tasking tasks and/or multi-tasking tasks) are compared to determine the efficacy of the drug on the individual's performance in interacting with the cognitive platform. The example analysis (and associated computation) also can be performed by comparing effects of group classification (such as but not limited to grouping based on amyloid status) versus drug interactions for sessions of user interaction with the cognitive platform or platform product, where the cData (from performance of single-tasking tasks and/or multi-tasking tasks) are compared to determine the efficacy of the drug on the individual's performance in interacting with the cognitive platform. The example analysis (and associated computation) also can be performed by comparing effects of group classification (such as but not limited to grouping based on amyloid status) versus drug interactions for sessions (and types of tasks) of user interaction with the cognitive platform or platform product, where the cData (from performance of single-tasking tasks and/or multi-tasking tasks) are compared to determine the efficacy of the drug on the individual's performance in interacting with the cognitive platform.

In this example implementation, certain cData collected from the individual's interaction with the tasks (and associated CSIs) presented by the cognitive platform or platform product, and/or metrics computed using the cData based on the analysis (and associated computations) described, can co-vary or otherwise correlate with the nData, such as but not limited to amyloid group and/or APOE expression group (or other expression group based on the expression level of other protein(s) that can be of clinical interest in a neurodegenerative condition) and/or potential efficacy of use of the cognitive platform or platform product when the individual is administered a drug, biologic or other pharmaceutical agent. An example cognitive platform or platform product according to the principles herein can be configured to classify an individual as to amyloid group and/or APOE expression group (or other expression group based on the expression level of other protein(s) that can be of clinical interest in a neurodegenerative condition) and/or potential efficacy of use of the cognitive platform or platform product when the individual is administered a drug, biologic or other pharmaceutical agent based on the cData collected from the individual's interaction with the cognitive platform or platform product and/or metrics computed based on the analysis (and associated computations). The example cognitive platform or platform product can include, or communicate with, a machine learning tool or other computational platform that can be trained using the cData and metrics of Impl. 6 to perform the classification.

As described hereinabove, the example systems, methods, and apparatus according to the principles herein can be implemented, using at least one processing unit of a programmed computing device, to provide the cognitive platform of a platform product. FIG. 1 shows an example apparatus 100 according to the principles herein that can be used to implement the cognitive platform described hereinabove herein. The example apparatus 100 includes at least one memory 102 and at least one processing unit 104. The at least one processing unit 104 is communicatively coupled to the at least one memory 102.

Example memory 102 can include, but is not limited to, hardware memory, non-transitory tangible media, magnetic storage disks, optical disks, flash drives, computational device memory, random access memory, such as but not limited to DRAM, SRAM, EDO RAM, any other type of memory, or combinations thereof.

Example processing unit 104 can include, but is not limited to, a microchip, a processor, a microprocessor, a special purpose processor, an application specific integrated circuit, a microcontroller, a field programmable gate array, a general-purpose graphics processing unit, a neural network chip, any other suitable processor, or combinations thereof.

The at least one memory 102 is configured to store processor-executable instructions 106 and a computing component 108. The computing component 108 can include a set of executable instructions that causes the processing unit 104 to analyze the cData and nData. In a non-limiting example, the computing component 108 can be used to analyze the cData and/or nData received from the cognitive platform coupled with the one or more physiological or monitoring components and/or cognitive testing components coupled to the cognitive platform. As shown in FIG. 1, the memory 102 also can be used to store data 110, such as but not limited to the nData 112 (including measurement data from measurement(s) using one or more physiological or monitoring components and/or cognitive testing components) and/or data indicative of the response of an individual to the one or more tasks (cData), including responses to tasks rendered at a user interface of the apparatus 100 and/or tasks generated using an auditory, tactile, or vibrational signal from an actuating component coupled to or integral with the apparatus 100. The data 110 can be received from one or more physiological or monitoring components and/or cognitive testing components that are coupled to or integral with the apparatus 100.

In any example herein, the computing device can include the computing component 108.

In any example herein, the user interface can be a graphical user interface.

In a non-limiting example, the at least one processing unit 104 executes the processor-executable instructions 106 stored in the memory 102 at least to analyze the cData and/or nData received from the cognitive platform coupled with the one or more physiological or monitoring components and/or cognitive testing components coupled to the cognitive platform, using the computing component 108. The at least one processing unit 104 also executes processor-executable instructions 106 to control a transmission unit to transmit values indicative of the analysis of the cData and/or nData received from the one or more physiological or monitoring components coupled with the cognitive platform and/or cognitive testing components as described herein, and/or controls the memory 102 to store values indicative of the analysis of the cData and/or nData.

In another non-limiting example, the measurement data (nData 112) can be collected from measurements using one or more physiological or monitoring components and/or cognitive testing components. In any example herein, the one or more physiological components are configured for performing physiological measurements. The physiological measurements provide quantitative measurement data of physiological parameters and/or data that can be used for visualization of physiological structure and/or functions.

In any example herein, the cData can include reaction time, response variance, correct hits, omission errors, number of false alarms (such as but not limited to a response to a non-target), learning rate, spatial deviance, subjective ratings, and/or performance threshold, or data from an analysis, including percent accuracy, hits, and/or misses in the latest completed trial or session. Measures of the reaction time indicate the time the individual takes to initiate a response to an interference (such as but not limited to a target or non-target) from the moment the interference is launched. The performance threshold can be set by the example system or apparatus based on previous measurement cData indicating the individual's performance of the tasks and/or interference. Other non-limiting examples of cData include response time (total of reaction time and the time it takes the individual to complete the response to the interference), task completion time, number of tasks completed in a set amount of time, preparation time for task, accuracy of responses, accuracy of responses under set conditions (e.g., stimulus difficulty or magnitude level and association of multiple stimuli), number of responses a participant can register in a set time limit number of responses a participant can make with no time limit, number of attempts at a task needed to complete a task, movement stability, accelerometer and gyroscope data, and self-rating.

In any example herein, the one or more physiological components can include any means of measuring physical characteristics of the body and nervous system, including electrical activity, heart rate, blood flow, and oxygenation levels, to provide the measurement data (nData 112). This can include camera-based heart rate detection, measurement of galvanic skin response, blood pressure measurement, electroencephalogram, electrocardiogram, magnetic resonance imaging, near-infrared spectroscopy, and/or pupil dilation measures, to provide the measurement data (nData 112). The one or more physiological components can include one or more sensors for measuring parameter values of the physical characteristics of the body and nervous system, and one or more signal processors for processing signals detected by the one or more sensors.

Other examples of physiological measurements to provide measurement data (nData 112) include, but are not limited to, the measurement of body temperature, heart or other cardiac-related functioning using an electrocardiograph (ECG), electrical activity using an electroencephalogram (EEG), event-related potentials (ERPs), functional magnetic resonance imaging (fMRI), blood pressure, electrical potential at a portion of the skin, and/or galvanic skin response (GSR). The physiological measurements can be made using, e.g., functional magnetic resonance imaging (fMRI), magneto-encephalogram (MEG), and/or functional near-infrared spectroscopy (fNIRS). The devices for making physiological measurements can include, e.g., an eye-tracking device or other optical detection device including processing units programmed to determine degree of pupillary dilation, functional near-infrared spectroscopy (fNIRS), and/or a positron emission tomography (PET) scanner. An EEG-fMRI or MEG-fMRI measurement allows for simultaneous acquisition of electrophysiology (EEG/MEG) data and hemodynamic (fMRI) data.

The example apparatus 100 of FIG. 1 can be configured as a computing device for performing any of the example methods described herein. The computing device can include an App program for performing some of the functionality of the example methods described herein.

In any example herein, the example apparatus 100 can be configured to communicate with one or more of a monitoring component, a disease monitoring component, and a physiological measurement component, to provide for biofeedback and/or neurofeedback of data to the computing device, for adjusting a type or a difficulty level of one or more of the task, and the interference, to achieve the desired performance level of the individual. Uses of the biofeedback and neurofeedback are described below. Examples of the monitoring component include a device for performing a TOVA® test. Examples of the disease monitoring component include any type of device that can be used for monitoring symptoms of a disease. As a non-limiting example, the biofeedback can be based on physiological measurements of the individual as the individual interacts with the apparatus 100, in which the biofeedback can be used by the computing component 108 to modify the type or a difficulty level of one or more of the task, and the interference. As a non-limiting example, the neurofeedback can be based on measurement and monitoring of the individual using a cognitive and/or a disease monitoring component as the individual interacts with the apparatus 100, in which the neurofeedback can be used by the computing component 108 to modify the type or a difficulty level of one or more of the task, and the interference, based on the measurement data indicating, e.g., the individual's cognitive state, to facilitate generating a scoring output (such as but not limited to a classification output) indicative of a likelihood of onset of a neurodegenerative condition of the individual and/or a stage of progression of the neurodegenerative condition.

In a non-limiting example, the at least one processing unit 104 executes the processor-executable instructions 106 stored in the memory 102 at least to: render a first instance of a primary task at the user interface, requiring a first primary response from the individual to the first instance of the primary task; render a first instance of a secondary task at the user interface, requiring a first secondary response from the individual to the first instance of the secondary task; and render at the user interface a second instance of the primary task with an interference (configured as a second instance of a secondary task), requiring a second primary response from the individual to the second instance of the primary task in the presence of the interference. The at least one processing unit 104 is configured to render the interference such that it diverts the individual's attention from the second instance of the primary task and is configured as an interruptor or a distraction. The at least one processing unit 104 is configured to use the user interface to instruct the individual not to respond to the interference that is configured as a distraction and to respond to the interference that is configured as an interruptor. The at least one processing unit 104 is further configured to receive data indicative of the first primary response, the first secondary response, the second primary response, and the response to the interference, and to analyze the differences in the individual's performance from performing the primary task without interference and with interference at least in part by determining differences between the data indicative of the first primary response and the second primary response, and analyzing one or both of the first secondary response or the response to the interference, to determine at least one indicator of the cognitive ability of the individual. The at least one processing unit 104 is further configured to execute a first predictive model based at least in part on the at least one indicator to generate a scoring output (such as but not limited to a classification output) indicative of a likelihood of onset of a neurodegenerative condition of the individual and/or a stage of progression of the neurodegenerative condition.

In a non-limiting example, the computing component 108 can be used to receive (including to measure) substantially simultaneously two or more of: (i) the response from the individual to a primary task (providing at least a portion of cData), (ii) a secondary response of the individual to an interference as an instance of a secondary task (providing at least a portion of cData), and (iii) at least one physiological measure using of the individual (using a measurement of at least one physiological component to provide at least a portion of nData). In a non-limiting example, the computing component 108 can be used to analyze the cData and/or nData received from the cognitive platform coupled with one or more physiological components as described herein to compute at least one indicator of cognitive abilities. In another non-limiting example, the computing component 108 can be used to compute the at least one indicator and/or apply the predictive model to generate the scoring output. As shown in FIG. 1, the memory 102 also can be used to store data 110, such as but not limited to the physiological measurement data (nData 112) received from a physiological component coupled to or integral with the apparatus 100 and/or data indicative of the response of an individual to the one or more tasks, including responses to tasks rendered at a user interface of the apparatus 100 and/or tasks generated using an auditory, tactile, and/or vibrational signal from an actuating component coupled to or integral with the apparatus 100, and/or data indicative of one or more of an amount, concentration, or dose titration, or other treatment regimen of a drug, pharmaceutical agent, biologic, or other medication being or to be administered to an individual.

In a non-limiting example, the at least one processing unit 104 executes the processor-executable instructions 106 stored in the memory 102 at least to measure substantially simultaneously two or more of: (i) the response from the individual to a task (providing at least a portion of cData), (ii) a secondary response of the individual to an interference as an instance of a secondary task (providing at least a portion of cData), and (iii) at least one physiological measure using of the individual (using a measurement of at least one physiological component to provide at least a portion of nData). The at least one processing unit 104 also executes the processor-executable instructions 106 stored in the memory 102 at least to analyze the cData and/or nData received from the one or more physiological components coupled with the cognitive platform, to compute at least one indicator of cognitive abilities, using the computing component 108. The at least one processing unit 104 also executes processor-executable instructions 106 to control a transmission unit to transmit values indicative of the analysis of the cData and/or nData received from the one or more physiological components coupled with the cognitive platform, and/or controls the memory 102 to store values indicative of the analysis of the cData and/or nData (including the at least one performance metric). The at least one processing unit 104 also may be programmed to execute processor-executable instructions 106 to control a transmission unit to transmit values indicative of the computed performance metrics and/or controls the memory 102 to store values indicative of the performance metrics.

In a non-limiting example, the at least one processing unit 104 executes the processor-executable instructions 106 stored in the memory 102 at a first timepoint T1 at least to: render a first instance of a primary task at the user interface, requiring a first primary response from the individual to the first instance of the primary task; and render a second instance of the primary task with an interference, requiring a second primary response from the individual to the second instance of the primary task in the presence of the interference. The at least one processing unit 104 is configured to use the user interface to instruct the individual not to respond to the interference that is configured as a distraction and to respond to the interference that is configured as an interruptor. The at least one processing unit 104 is configured to render the interference such that it diverts the individual's attention from the second instance of the primary task and is configured as an interruptor or a distraction. The at least one processing unit 104 executes the processor-executable instructions 106 stored in the memory 102 at a second timepoint T2 (subsequent to first timepoint T1) at least to: render a third instance of a primary task at the user interface, requiring a third primary response from the individual to the third instance of the primary task; and render a fourth instance of the primary task with an interference, requiring a fourth primary response from the individual to the fourth instance of the primary task in the presence of the interference. The at least one processing unit 104 is further configured to receive data indicative of the first primary response, the second primary response, the third primary response, and the fourth primary response, and to analyze the differences in the individual's performance from performing the primary task without interference and with interference at least in part by determining differences between the data indicative of two or more of: the first primary response, the second primary response, the third primary response, or the fourth primary response, to determine at least a first indicator of the cognitive ability of the individual. The at least one processing unit 104 is further configured to apply a predictive model based at least in part on the at least one indicator to generate a scoring output (such as but not limited to a classification output) indicative of a likelihood of onset of a neurodegenerative condition of the individual and/or a stage of progression of the neurodegenerative condition.

In a non-limiting example, the at least one processing unit 104 may be further configured to execute the processor-executable instructions 106 stored in the memory 102 at least to: adjust a difficulty of one or both of the primary task or the interference such that the apparatus renders at least one subsequent instance (i.e., at a later timepoint) of the primary task and/or the interference at a second difficulty level. For example, one or both the of third or fourth instance of the primary task can be rendered at a same difficulty level, or at a second (different) difficulty level than one or both of the first or second instance of the primary task. Independently, the interference rendered at timepoint T2 may be the same or different than the interference rendered at timepoint T1.

In a non-limiting example, the at least one processing unit 104 may be further configured to execute the processor-executable instructions 106 stored in the memory 102 at a third timepoint T3 (subsequent to second timepoint T2) at least to: render a fifth instance of a primary task at the user interface, requiring a fifth primary response from the individual to the fifth instance of the primary task; and render a sixth instance of the primary task with an interference, requiring a sixth primary response from the individual to the sixth instance of the primary task in the presence of the interference. The at least one processing unit 104 is further configured to receive data indicative of the first primary response, the second primary response, the third primary response, the fourth primary response, the fifth primary response and the sixth primary response, and to analyze the differences in the individual's performance from performing the primary task without interference and with interference at least in part by determining differences between the data indicative of three or more of: the first primary response, the second primary response, the third primary response, the fourth primary response, the fifth primary response or the sixth primary response, to determine at least a first indicator of the cognitive ability of the individual. The at least one processing unit 104 is further configured to apply a predictive model based at least in part on the at least one indicator to generate a scoring output (such as but not limited to a classification output) indicative of a likelihood of onset of a neurodegenerative condition of the individual and/or a stage of progression of the neurodegenerative condition.

In some examples, one or both the of fifth or sixth instance of the primary task can be rendered at a same difficulty level, or at a second (different) difficulty level than one or both of the third or fourth instance of the primary task. Independently, the interference rendered at timepoint T3 may be the same or different than the interference rendered at timepoint T2.

In a non-limiting example, the at least one processing unit 104 further executes the processor-executable instructions 106 stored in the memory 102 to apply a predictive model based at least in part on the at least one indicator determined using any of the examples herein to generate a scoring output (such as but not limited to a classification output) indicative of a likelihood of onset of a neurodegenerative condition of the individual and/or a stage of progression of the neurodegenerative condition. The predictive model can be trained using a plurality of training datasets, each training dataset corresponding to a previously classified individual of a plurality of individuals, and each training dataset including data representing the at least the first indicator of the cognitive ability of the classified individual and nData indicative of a diagnosis of a status or progression of the neurodegenerative condition in the classified individual. The trained predictive model can be applied to the at least one indicator of the cognitive ability of the individual (derived from the data indicative of the individual's interactions with the tasks and/or interference executed by the cognitive platform), to generate a scoring output. The scoring output can be used to provide an indication of a likelihood of onset of a neurodegenerative condition and/or a stage of progression of the neurodegenerative condition of an individual.

Using any example system, method or apparatus according to the principles herein, the scoring output (such as but not limited to a classification output) for an individual as to a likelihood of onset and/or stage of progression of a neurodegenerative condition can be transmitted as a signal to one or more of a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in dosage of a drug, biologic or other pharmaceutical agent to the individual or to determine an optimal type or combination of drug, biologic or other pharmaceutical agent to the individual.

In some examples, the results of the analysis may be used to modify the difficulty level or other property of the computerized stimuli or interaction (CSI) or other interactive elements.

Figure 2:
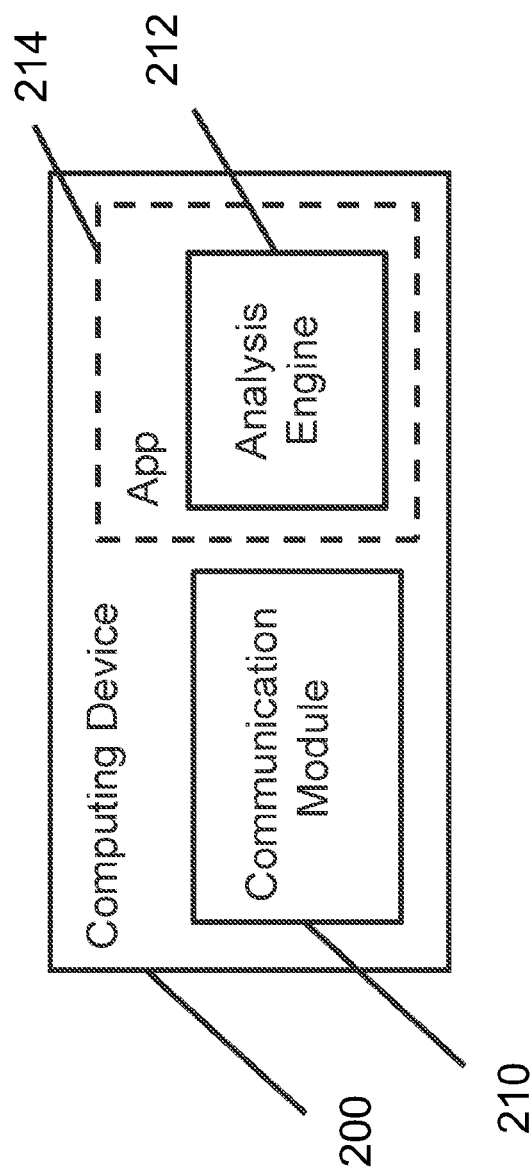
FIG. 2 shows a block diagram of an example computing device, according to the principles herein.

FIG. 2 shows another example apparatus according to the principles herein, configured as a computing device 200 that can be used to implement the cognitive platform according to the principles herein. The example computing device 200 can include a communication module 210 and an analysis engine 212. The communication module 210 can be implemented to receive data indicative of at least one response of an individual to the primary task in the absence of an interference, and/or at least one response of an individual to the primary task that is being rendered in the presence of the interference. In an example, the communication module 210 can be implemented to receive substantially simultaneously two or more of: (i) the response from the individual to a primary task, and (ii) a secondary response of the individual to an interference. The analysis engine 212 can be implemented to analyze the data from the at least one sensor component as described herein and/or to analyze the data indicative of the responses to compute at least one indicator of cognitive abilities. In another example, the analysis engine 212 can be implemented to apply a predictive model based at least in part on the at least one indicator to generate a scoring output (such as but not limited to a classification output) indicative of a likelihood of onset of a neurodegenerative condition of the individual and/or a stage of progression of the neurodegenerative condition. The predictive model can be trained using a plurality of training datasets, each training dataset corresponding to a previously classified individual of a plurality of individuals, and each training dataset including data representing the at least the first indicator of the cognitive ability of the classified individual and nData indicative of a diagnosis of a status or progression of the neurodegenerative condition in the classified individual. As shown in the example of FIG. 2, the computing device 200 can include processor-executable instructions such that a processor unit can execute an application program (App 214) that a user can implement to initiate the analysis engine 212. In an example, the processor-executable instructions can include software, firmware, or other instructions. The analysis engine 212 can be configured to apply the trained predictive model to the at least one indicator of the cognitive ability of the individual (derived from the data indicative of the individual's interactions with the tasks and/or interference executed by the cognitive platform), to generate a scoring output. The scoring output can be used to provide an indication of a likelihood of onset of a neurodegenerative condition and/or a stage of progression of the neurodegenerative condition of an individual.

The example communication module 210 can be configured to implement any wired and/or wireless communication interface by which information may be exchanged between the computing device 200 and another computing device or computing system. Non-limiting examples of wired communication interfaces include, but are not limited to, USB ports, RS232 connectors, RJ45 connectors, Thunderbolt™ connectors, and Ethernet connectors, and any appropriate circuitry associated therewith. Non-limiting examples of wireless communication interfaces may include, but are not limited to, interfaces implementing Bluetooth® technology, Wi-Fi, Wi-Max, IEEE 802.11 technology, radio frequency (RF) communications, Infrared Data Association (IrDA) compatible protocols, Local Area Networks (LAN), Wide Area Networks (WAN), and Shared Wireless Access Protocol (SWAP).

In an example implementation, the example computing device 200 includes at least one other component that is configured to transmit a signal from the apparatus to a second computing device. For example, the at least one component can include a transmitter or a transceiver configured to transmit a signal including data indicative of a measurement by at least one sensor component to the second computing device.

In any example herein, the App 214 on the computing device 200 can include processor-executable instructions such that a processor unit of the computing device implements an analysis engine to analyze data indicative of the individual's response to the rendered tasks and/or interference (either or both with computer-implemented time-varying element) and the response of the individual to the at least one computer-implemented time-varying element to compute at least one indicator of cognitive abilities. In another example, the App 214 on the computing device 200 can include processor-executable instructions such that a processor unit of the computing device implements an analysis engine to analyze the data indicative of the individual's response to the rendered tasks and/or interference (either or both with computer-implemented time-varying element) and the response of the individual to the at least one computer-implemented time-varying element to provide a predictive model based on the computed values of the performance metric, to generate a predictive model output indicative of a measure of cognition, a mood, a level of cognitive bias, or an affective bias of the individual. In some examples, the App 214 can include processor-executable instructions such that the processing unit of the computing device implements the analysis engine to apply a predictive model trained to provide a scoring output as to a likelihood of onset of a neurodegenerative condition of the individual and/or a stage of progression of the neurodegenerative condition based at least in part on applying the first predictive model to the at least one indicator, and other metrics and analyses described herein.

In some example, the App 214 can include processor-executable instructions to provide one or more of: (i) a predictive model output indicative of the cognitive capabilities of the individual, (ii) a likelihood of the individual experiencing an adverse event in response to administration of the pharmaceutical agent, drug, or biologic, (iii) a likelihood of the individual experiencing an adverse event in response to a change in one or more of the amount, concentration, or dose titration of the pharmaceutical agent, drug, or biologic, (iv) a change in the individual's cognitive capabilities, (v), a recommended treatment regimen, (vi) a recommendation of at least one of a behavioral therapy, counseling, or physical exercise, or (vii) a determination of a degree of effectiveness of at least one of a behavioral therapy, counseling, or physical exercise.

In an example, the App 214 can include processor-executable instructions such that the processing unit of the computing device implements the analysis engine to apply a second predictive model (including a second classifier) that is trained to provide a second scoring that is indicative of one or more of: (i) a likelihood of the individual experiencing an adverse event in response to administration of the pharmaceutical agent, drug, or biologic, (ii) a likelihood of the individual experiencing an adverse event in response to a change in one or more of the amount, concentration, or dose titration of the pharmaceutical agent, drug, or biologic, (iii) a change in the individual's cognitive capabilities, (iv), a recommended treatment regimen, (v) a recommendation of at least one of a behavioral therapy, counseling, or physical exercise, (vi) a determination of a degree of effectiveness of at least one of a behavioral therapy, counseling, or physical exercise. The second predictive model can be trained using a plurality of training datasets, where each training dataset is associated with a previously classified individual from a group of individuals. Each training dataset includes data representing the scoring output derived as described herein from the application of a first predictive model to the at least one indicator of the cognitive ability of the classified individual. Each training dataset also includes data indicative of one or more of (i) an indication (including a description) of the adverse event the individual experienced in response to administration of the pharmaceutical agent, drug, or biologic, or in response to a change in one or more of the amount, concentration, or dose titration of that pharmaceutical agent, drug, or biologic, (ii) the treatment regimen of the individual and a rating as to a degree of effectiveness (i.e., a rating of a success or failure) of the regimen in connection with the treatment or management of symptoms of the neurodegenerative condition, (iii) a type and a rating as to a degree of effectiveness (i.e., a rating of a success or failure) of any behavioral therapy, counseling, or physical exercise the individual is undergoing in connection with the treatment or management of symptoms of the neurodegenerative condition. The trained second predictive model can be applied to the scoring output (including a classification output) of the individual (derived from the data indicative of the individual's interactions with the tasks and/or interference executed by the cognitive platform), to generate the second scoring as an output.

In any example herein, the App 214 can be configured to receive measurement data including physiological measurement nData of an individual received from a physiological component, and/or cData indicative of the response of an individual to a task and/or an interference rendered at a user interface of the apparatus 100 (as described in greater detail below), and/or data indicative of one or more of an amount, concentration, or dose titration, or other treatment regimen of a drug, pharmaceutical agent, biologic, or other medication being or to be administered to an individual.

FIG. 3A shows a non-limiting example system, method, and apparatus according to the principles herein, where the platform product (which may include an APP) is configured as a cognitive platform 302 that is separate from, but configured for coupling with, one or more of the physiological components 304.

FIG. 3B shows another non-limiting example system, method, and apparatus according to the principles herein, where the platform product (which may include an APP) is configured as an integrated device 310, where the cognitive platform 312 that is integrated with one or more of the physiological components 314.

Figure 4:
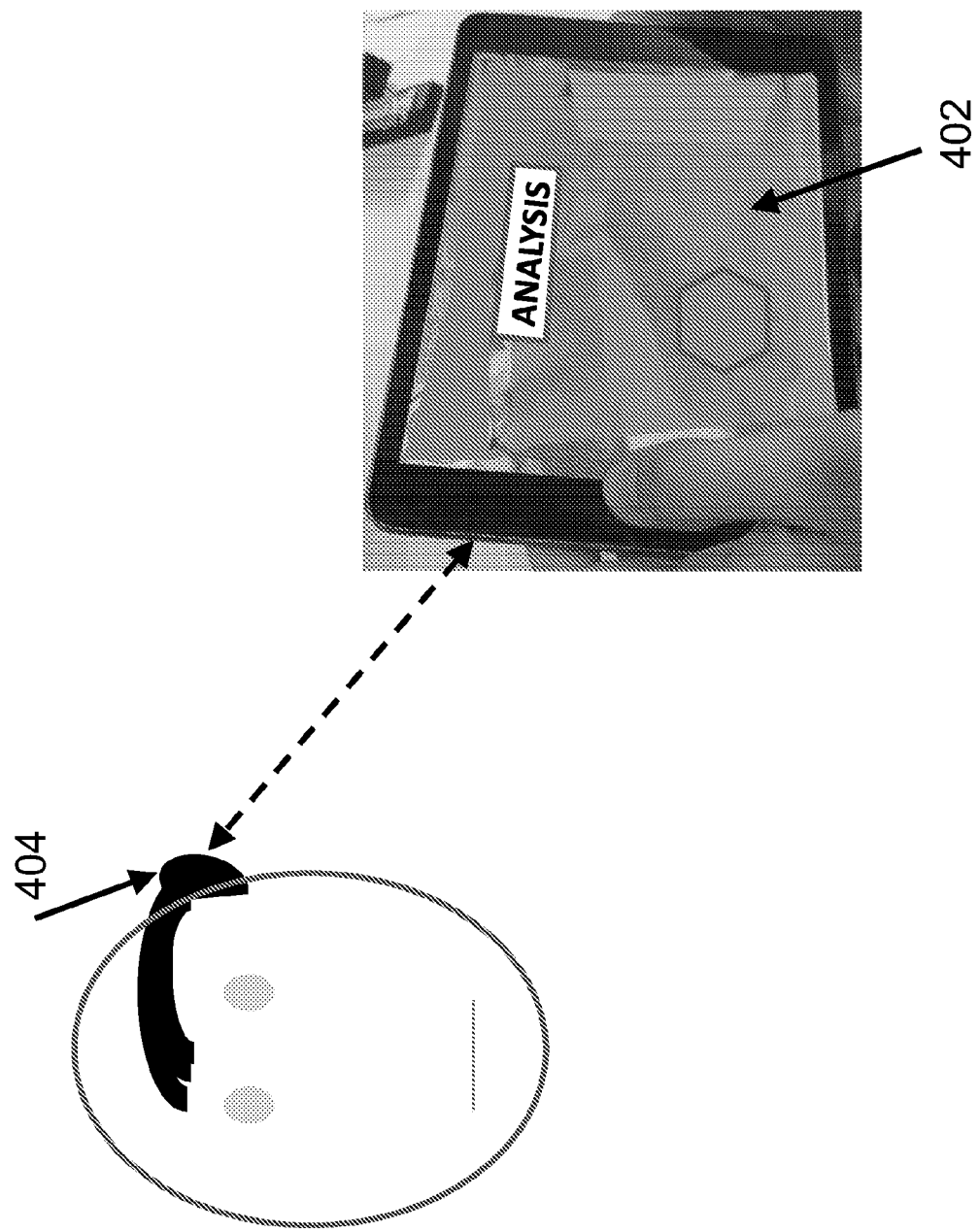
FIG. 4 shows another example system, according to the principles herein.

FIG. 4 shows a non-limiting example implementation where the platform product (which may include an APP) is configured as a cognitive platform 402 that is configured for coupling with a physiological component 404. In this example, the cognitive platform 402 is configured as a tablet including at least one processor programmed to implement the processor-executable instructions associated with the tasks and CSIs described hereinabove, to receive cData associated with user responses from the user interaction with the cognitive platform 402, to receive the nData from the physiological component 404, to analyze the cData and/or nData as described hereinabove, and to analyze the cData and/or nData to provide a measure of the individual's physiological condition and/or cognitive condition. The cognitive platform can be configured to analyze the differences in the individual's performance based on determining the differences between sets of data, each set of data including data indicative of the user's responses to the tasks in the presence and in the absence of interference and the nData, and/or adjust the difficulty level of the computerized stimuli or interaction (CSI) or other interactive elements based on the individual's performance determined in the analysis and based on the analysis of the cData and/or nData. The cognitive platform can be configured to provide an output or other feedback from the platform product indicative of at least one of: (i) the individual's performance, (ii) cognitive assessment, (iii) response to cognitive treatment, or (iv) assessed measures of cognition. In this example, the physiological component 404 is configured as an EEG device mounted to a user's head, to perform the measurements before, during and/or after user interaction with the cognitive platform 402, to provide the nData.

In a non-limiting example implementation, the EEG device can be a low-cost EEG device for medical treatment validation and personalized medicine. The low-cost EEG device can be easier to use and has the potential to vastly improve the accuracy and the validity of medical applications. In this example, the platform product may be configured as an integrated device including the EEG component coupled with the cognitive platform, or as a cognitive platform that is separate from, but configured for coupling with the EEG component.

In a non-limiting example use for treatment validation, the user interacts with a cognitive platform, and the EEG device is used to perform physiological measurements of the user. Changes, if any, in EEG measurements data (such as brainwaves) are monitored based on the actions of the user in interacting with the cognitive platform. The nData (e.g., brainwave measurements) using the EEG device can be collected and analyzed to detect changes in the EEG measurements. This analysis can be used to determine the types of response from the user, such as whether the user is performing according to an optimal or desired profile.

In a non-limiting example use for personalized medicine, the nData from the EEG to measurements can be used to identify changes in user performance/condition that indicate that the cognitive platform treatment is having the desired effect. The nData from the EEG measurements can also be used to determine the type of tasks and/or CSIs that works for a given user). The analysis can be used to determine whether the cognitive platform should be caused to provide tasks and/or CSIs to enforce or diminish these user results detected by the EEG device by adjusting the user's experience when interacting with the cognitive platforms.

In a non-limiting example implementation, measurements are made using a cognitive platform that is configured for coupling with a fMRI, for use for medical application validation and personalized medicine. Consumer-level fMRI devices may be used to improve the accuracy and the validity of medical applications by tracking and detecting changes in brain part stimulation.

In a non-limiting example, fMRI measurements can be used to provide measurement data of the cortical thickness and other similar measurement data.

In a non-limiting example use for treatment validation, the user interacts with a cognitive platform, and the fMRI is used to measure physiological data. The user is expected to have stimulation of a particular brain part or combination of brain parts (such as but not limited to the prefrontal cortex, the visual cortex, or the hippocampus) based on the actions of the user while interacting with the cognitive platform. In this example, the platform product may be configured as an integrated device including the fMRI component coupled with the cognitive platform, or as a cognitive platform that is separate from, but configured for coupling with the fMRI component. Using the cognitive platform with the fMRI, measurement can be made of the stimulation of portions of the user brain, and analysis can be performed to detect changes in the measurements to determine whether the user exhibits the desired responses.

In a non-limiting example use for personalized medicine, the fMRI can be used to collect measurement data to be used to identify the progress of the user in interacting with the cognitive platform. The analysis can be used to determine whether the cognitive platform should be caused to provide tasks and/or CSIs to enforce or diminish these user results detected by the fMRI, by adjusting the user's experience in interacting with the cognitive platform.

In any example herein, the system, methods or apparatus can be configured to make adjustments in real-time to one or both of the difficulty levels or the type of the tasks and/or interference (including CSIs).

An example system, method, and apparatus according to the principles herein can be configured to train a predictive model of a measure of the cognitive capabilities of individuals based on feedback data from the output for individuals that are previously classified as to the measure of cognitive abilities of interest. For example, a predictive model (including a condition classifier) can be trained using a plurality of training datasets, in which each training dataset is associated with a previously classified individual from a group of individuals. Each training dataset includes data representing the at least one indicator of the cognitive ability of the classified individual and nData indicative of a diagnosis of a status or progression of the neurodegenerative condition in the classified individual, based on the classified individual's interaction with an example apparatus, system, or computing device described herein. The example classifier also can take as input at least one of: (i) data indicative of the performance of the classified individual at a cognitive test, (ii) data indicative of the behavioral test, and/or data indicative of a diagnosis of a status, or (iii) data indicative of the progression of the neurodegenerative condition. The trained classifier can be applied to the at least one indicator of the cognitive ability of the individual (derived from the data indicative of the individual's interactions with the tasks and/or interference executed by the cognitive platform), to generate a scoring output (such as but not limited to a classification output). The scoring output (including a classification output) can be used to provide an indication of a likelihood of onset of a neurodegenerative condition and/or a stage of progression of the neurodegenerative condition of an individual.

In any example herein, the at least one processing unit can be programmed to cause an actuating component of a system (including the cognitive platform) to effect auditory, tactile, and/or vibrational computerized elements to effect the stimulus or other interaction with the individual. In a non-limiting example, the at least one processing unit can be programmed to cause a component of the cognitive platform to receive data indicative of at least one response from the individual based on the user interaction with the task and/or interference, including responses received at an input device. In an example where at least one graphical user interface is rendered to present the computerized stimulus to the individual, the at least one processing unit can be programmed to cause the graphical user interface to receive the data indicative of at least one response from the individual.

In any example herein, the data indicative of the response of the individual to a task and/or an interference can be measured using at least one sensor device contained in and/or coupled to an example system or apparatus herein, such as but not limited to a gyroscope, an accelerometer, a motion sensor, a position sensor, a pressure sensor, an optical sensor, an auditory sensor, a vibrational sensor, a video camera, a pressure-sensitive surface, a touch-sensitive surface, or other type of sensor. In other examples, the data indicative of the response of the individual to the task and/or an interference can be measured using other types of sensor devices, including a video camera, a microphone, a joystick, a keyboard, a mouse, a treadmill, an elliptical, a bicycle, steppers, or a gaming system (including a Wii®, a Playstation®, or an Xbox® or another gaming system). The data can be generated based on physical actions of the individual that are detected and/or measured using the at least one sensor device when the individual executes a response to the stimuli presented with the task and/or interference.

The user may respond to tasks by interacting with the computer device. In an example, the user may execute a response using a keyboard for alpha-numeric or directional inputs; a mouse for GO/NO-GO clicking, screen location inputs, and movement inputs; a joystick for movement inputs, screen location inputs, and clicking inputs; a microphone for audio inputs; a camera for still or motion optical inputs; sensors such as accelerometer and gyroscopes for device movement inputs; among others. Non-limiting example inputs for a game system include but are not limited to a game controller for navigation and clicking inputs, a game controller with accelerometer and gyroscope inputs, and a camera for motion optical inputs. Example inputs for a mobile device or tablet include a touch screen for screen location information inputs, virtual keyboard alpha-numeric inputs, GO/NO-GO tapping inputs, and touch screen movement inputs; accelerometer and gyroscope motion inputs; a microphone for audio inputs; and a camera for still or motion optical inputs, among others. In other examples, data indicative of the individual's response can include physiological sensors/measures to incorporate inputs from the user's physical state, such as but not limited to electroencephalogram (EEG), magnetoencephalography (MEG), heart rate, heart rate variability, blood pressure, weight, eye movements, pupil dilation, electrodermal responses such as the galvanic skin response, blood glucose level, respiratory rate, and blood oxygenation.

In any example herein, the individual may be instructed to provide a response via a physical action of clicking a button and/or moving a cursor to a correct location on a screen, head movement, finger or hand movement, vocal response, eye movement, or other action of the individual.

As a non-limiting example, an individual's response to a task or interference rendered at the user interface that requires a user to navigate a course or environment or perform other visuo-motor activity may require the individual to make movements (such as but not limited to steering) that are detected and/or measured using at least one type of the sensor device. The data from the detection or measurement provides the data indicative of the response.

As a non-limiting example, an individual's response to a task or interference rendered at the user interface that requires a user to discriminate between a target and a non-target may require the individual to make movements (such as but not limited to tapping or other spatially or temporally discriminating indication) that are detected and/or measured using at least one type of the sensor device. The data that is collected by a component of the system or apparatus based on the detection or other measurement of the individual's movements (such as but not limited to at least one sensor or other device or component described herein) provides the data indicative of the individual's responses.

The example system, method, and apparatus can be configured to apply the predictive model, using computational techniques and machine learning tools, such as but not limited to linear/logistic regression, principal component analysis, generalized linear mixed models, random decision forests, support vector machines, or artificial neural networks, to the data indicative of the individual's response to the tasks and/or interference, and/or data from one or more physiological measures, to create composite variables or profiles that are more sensitive than each measurement alone for generating a predictive model output indicative of the cognitive response capabilities of the individual. In an example, the predictive model output can be configured for other indications such as but not limited to detecting an indication of a disease, disorder or cognitive condition, or assessing cognitive health.

The example predictive models herein can be trained to be applied to data collected from interaction sessions of individuals with the cognitive platform to provide the output. In a non-limiting example, the predictive model can be used to generate a standards table, which can be applied to the data collected from the individual's response to task and/or interference to classify the individual's cognitive response capabilities.

Non-limiting examples of assessment of cognitive abilities include assessment scales or surveys such as the Mini Mental State Exam, CANTAB cognitive battery, Test of Variables of Attention (TOVA), Repeatable Battery for the Assessment of Neuropsychological Status, Clinical Global Impression scales relevant to specific conditions, Clinician's Interview-Based Impression of Change, Severe Impairment Battery, Alzheimer's Disease Assessment Scale, Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale, Aberrant Behavior Checklist, Activities for Daily Living scales, ADHD self-report scale, Positive and Negative Affect Schedule, Depression Anxiety Stress Scales, Quick Inventory of Depressive Symptomatology, and PTSD Checklist.

In other examples, the assessment may test specific functions of a range of cognitions in cognitive or behavioral studies, including tests for perceptive abilities, reaction and other motor functions, visual acuity, long-term memory, working memory, short-term memory, logic, and decision-making, and other specific example measurements, including but are not limited to TOVA, MOT (motion-object tracking), SART (Sustained Attention to Response Task), CDT (Change detection task), UFOV (useful Field of view), Filter task, WAIS (Wechsler Adult Intelligence Scale) digit symbol, Troop, Simon task, Attentional Blink, N-back task, PRP (Psychological Refractory Period) task, task-switching test, and Flanker task.

In non-limiting examples, the example systems, methods, and apparatus according to the principles described herein can be applicable to many different types of neuropsychological conditions, such as but not limited to dementia, Parkinson's disease, cerebral amyloid angiopathy, familial amyloid neuropathy, Huntington's disease, or other neurodegenerative condition.

The instant disclosure is directed to computer-implemented devices formed as example cognitive platforms configured to implement software and/or other processor-executable instructions for the purpose of measuring data indicative of a user's performance at one or more tasks, to provide a user performance metric. The example performance metric can be used to derive an assessment of a user's cognitive abilities and/or to measure a user's response to a cognitive treatment, and/or to provide data or other quantitative indicia of a user's condition (including physiological condition and/or cognitive condition). Non-limiting example cognitive platforms according to the principles herein can be configured to classify an individual as to a likelihood of onset of a neurodegenerative condition of the individual and/or a stage of progression of the neurodegenerative condition, and/or potential efficacy of use of the cognitive platform when the individual is being administered (or about to be administered) a drug, biologic or other pharmaceutical agent, based on the data collected from the individual's interaction with the cognitive platform and/or metrics computed based on the analysis (and associated computations) of that data. The neurodegenerative condition can be, but is not limited to, Alzheimer's disease, dementia, Parkinson's disease, cerebral amyloid angiopathy, familial amyloid neuropathy, or Huntington's disease.

Any classification of an individual as to likelihood of onset and/or stage of progression of a neurodegenerative condition according to the principles herein can be transmitted as a signal to a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in dosage of a drug, biologic or other pharmaceutical agent to the individual or to determine an optimal type or combination of drug, biologic or other pharmaceutical agent to the individual.

In any example herein, the cognitive platform can be configured as any combination of a medical device platform, a monitoring device platform, a screening device platform, or other device platform.

The instant disclosure is also directed to example systems that include cognitive platforms that are configured for coupling with one or more physiological or monitoring component and/or cognitive testing component. In some examples, the systems include cognitive platforms that are integrated with the one or more other physiological or monitoring component and/or cognitive testing component. In other examples, the systems include cognitive platforms that are separately housed from and configured for communicating with the one or more physiological or monitoring component and/or cognitive testing component, to receive data indicative of measurements made using such one or more components.

In an example system, method, and apparatus herein, the processing unit can be programmed to control the user interface to modify a temporal length of the response window associated with a response-deadline procedure.

In an example system, method, and apparatus herein, the processing unit can be further programmed to control the user interface to render the task as a continuous visuo-motor tracking task.

In an example system, method, and apparatus herein, the processing unit controls the user interface to render the interference as a target discrimination task.

As used herein, a target discrimination task may also be referred to as a perceptual reaction task, in which the individual is instructed to perform a two-feature reaction task including target stimuli and non-target stimuli through a specified form of response. As a non-limiting example, that specified type of response can be for the individual to make a specified physical action in response to a target stimulus (e.g., move or change the orientation of a device, tap on a sensor-coupled surface such as a screen, move relative to an optical sensor, make a sound, or other physical action that activates a sensor device) and refrain from making such specified physical action in response to a non-target stimulus.

In a non-limiting example, the individual is required to perform a visuomotor task (as a primary task) with a target discrimination task as an interference (an instance of a secondary task) (either or both including a computer-implemented time-varying element). To effect the visuomotor task, a programmed processing unit renders visual stimuli that require fine motor movement as reaction of the individual to the stimuli. In some examples, the visuomotor task is a continuous visuomotor task. The processing unit is programmed to alter the visual stimuli and record data indicative of the motor movements of the individual over time (e.g., at regular intervals including 1, 5, 10, or 30 times per second). Example stimuli rendered using the programmed processing unit for a visuomotor task requiring fine motor movement may be a visual presentation of a path that an avatar is required to remain within. The programmed processing unit may render the path with certain types of obstacles that the individual is either required to avoid or to navigate towards. In an example, the fine motor movements effect by the individual, such as but not limited to tilting or rotating a device, are measured using an accelerometer and/or a gyroscope (e.g., to steer or otherwise guide the avatar on the path while avoiding or crossing the obstacles as specified). The target discrimination task (serving as the interference), can be based on targets and non-targets that differ in shape and/or color.

In any example, the apparatus may be configured to instruct the individual to provide the response to the computer-implemented time-varying element as an action that is read by one or more sensors, such as a movement that is sensed using a gyroscope or accelerometer or a motion or position sensor, or a touch that is sensed using a touch-sensitive, pressure sensitive or capacitance-sensitive sensor.

In some examples, the task and/or interference can be a visuomotor task, a target discrimination task, and/or a memory task.

Within the context of a computer-implemented adaptive response-deadline procedure, the response-deadline can be adjusted between trials or blocks of trials to manipulate the individual's performance characteristics towards certain goals. A common goal is driving the individual's average response accuracy towards a certain value by controlling the response deadline.

In a non-limiting example, the hit rate may be defined as the number of correct responses to a target stimuli divided by the total number of target stimuli presented. The false alarm rate can be calculated as the number of responses to a distractor stimuli divided by the number of distractor stimuli presented). The miss rate can be calculated as the number of nonresponses to a target stimuli divided by the number of incorrect responses, including the nonresponses to a target stimuli added to the number of responses to a distractor stimuli. The correct response rate can be calculated as the proportion of correct responses not containing signal (e.g., where the individual correctly responds to the distractor by refraining from effecting an action, such as a tap or other action, if the distractor is rendered). In an example, the correct response rate may be calculated as the number of non-responses to the distractor stimuli divided by the number of non-responses to the distractor stimuli plus the number of responses to the target stimuli.

In some examples, the tasks and/or interference are presented to the individual in two or more trials and/or sessions, with an interspersed interval between each trial and/or session. In some examples, the computing system is configured to implement the tasks and/or interference in the subsequent trial(s) and/or session(s) at a difficulty level that is changed or maintained the same from one trial to another and/or from one session to another. For example, the difficulty level in each subsequent trial and/or each subsequent session can be dependent on the performance of the individual in the previous trial and/or previous session. Based on an analysis by the computing system indicating that the number of correct inputs in the responses made by the individual in a previous trial and/or session increases or reaches a specific threshold (e.g. a pre-determined percentage of correct responses), the computing system is configured to implement the tasks and/or interference in the subsequent trial and/or session at a higher difficulty level than the previous trial and/or session. Based on an analysis by the computing system indicating that the number of correct inputs in the responses made by the individual is decreased, is at or below a specified threshold, achieves a specified level of failure, or fails to achieve a level of success, in the previous trial and/or session, the computing system is configured to implement the tasks and/or interference in the subsequent trial and/or session at a lower difficulty level than the previous trial and/or session. In some examples, the computing system is configured to implement the tasks and/or interference in the subsequent trial(s) and/or session(s) at a difficulty level in a step-wise and/or in a peaks and valley fashion.

To modulate the difficulty level of a trial and/or a session, the computing system can be configured to modify the difficulty level of the primary task, or of the interference, or of some combination of the primary task and the interference. The modulation of the difficulty level may be based on either the data indicative of the actual performance of the individual in performing the task or interference (as determined by measurement as the input to a task or interference) or a more indirect parameter governed by the analysis, e.g., a performance metric such as but not limited to the interference cost. In some examples, the level of difficulty of the task and/or the interference can be adjusted based on an adaptive staircase algorithm at an accuracy of about 50%, about 55%, about 60%, about 65%, about 70%, about 75%, about 80%, about 85%, or about 90% or more.

In another example, the computing system can be configured to modify the difficulty level such that the platform is specifically tailored to an individual, e.g., by maintaining the difficulty level at or around a threshold success rate for the individual. For example, the computing system can be configured to target the difficulty level to maintain a substantially constant error rate from an individual (e.g., to maintain substantially approximately 80% response accuracy). In other examples, the computing system can be configured to target the difficulty level to maintain an accuracy of performance from the individual of about 50%, about 55%, about 60%, about 65%, about 70%, about 75%, about 80%, about 85%, or about 90% or more. The difficulty level of a task for a given individual may be determined by implementing the task without interference (e.g., single-tasking) initially at a default difficulty level for a category of individuals (e.g. average for an age range), a lowest level of difficulty, or a level comparable based on the individual's prior assessment. In subsequent trials and/or sessions, the difficulty level can be change until analysis of the measured data indicates that the individual is performing at a specific threshold level (e.g., percent accuracy).

In an example, the difficulty of the task (potentially including a computer-implemented time-varying element) adapts with every stimuli that is presented, which could occur more often than once at regular time intervals (e.g., every 5 seconds, every 10 seconds, every 20 seconds or other regular schedule).

In another example, the difficulty of a continuous task (potentially including a computer-implemented time-varying element) can be adapted on a set schedule, such as but not limited to every 30 seconds, 10 seconds, 1 second, 2 times per second, or 30 times per second.

In an example, the length of time of a trial depends on the number of iterations of rendering (of the tasks/interference) and receiving (of the individual's responses) and can vary in time. In an example, a trial can be on the order of about 500 milliseconds, about 1 second (s), about 10 s, about 20 s, about 25 s, about 30 s, about 45 s, about 60 s, about 2 minutes, about 3 minutes, about 4 minutes, about 5 minutes, or greater. Each trial may have a pre-set length or may be dynamically set by the processing unit (e.g., dependent on an individual's performance level or a requirement of the adapting from one level to another).

In an example, the task and/or interference (either or both including a computer-implemented time-varying element) can be modified based on targeting changes in one or more specific metrics by selecting features, trajectory, and response window of the targeting task, and level/type of parallel task interference to progressively require improvements in those metrics in order for the apparatus to indicate to an individual that they have successfully performed the task. This could include specific reinforcement, including explicit messaging, to guide the individual to modify performance according to the desired goals.

In an example, the indication of the modification of the cognitive abilities can include a change in a measure of one or more of affective bias, mood, level of cognitive bias, sustained attention, selective attention, attention deficit, impulsivity, inhibition, perceptive abilities, reaction and other motor functions, visual acuity, long-term memory, working memory, short-term memory, logic, and decision-making.

Example systems, methods and apparatus according to the principles herein can be implemented using a programmed computing device including at least one processing unit, to determine a potential biomarker for clinical populations.

An example system, method, and apparatus according to the principles herein can be configured to enhance the cognitive skills in an individual. In an example implementation, a programmed processing unit is configured to execute processor-executable instructions at least to: render a first instance of a primary task at the user interface, requiring a first primary response from the individual to the first instance of the primary task; and render a first instance of a secondary task at the user interface, requiring a first secondary response from the individual to the first instance of the secondary task. The programmed processing unit is configured to use the user interface to instruct the individual not to respond to an interference with the primary task that is configured as a distraction and to respond to an interference with the primary task that is configured as an interruptor. The programmed processing unit is configured to render at the user interface a second instance of the primary task with a first interference, requiring a second primary response from the individual to the second instance of the primary task in the presence of the first interference. The first interference is configured to divert the individual's attention from the second instance of the primary task and is configured as an instance of the secondary task that is rendered as an interruptor or a distraction. The programmed processing unit is also configured to receive data indicative of the first primary response, the first secondary response, the second primary response, and the response to the interference; and to adjust a difficulty of one or both of the primary task or the interference such that the apparatus renders one or both of a third instance of the primary task or the interference at a second difficulty level. The programmed processing unit is further configured to render at the user interface a third instance of the primary task with a second interference, requiring a third primary response from the individual to the third instance of the primary task in the presence of the second interference; receive data indicative of the third primary response and the response to the second interference; and analyze the differences in the individual's performance from performing the primary task without interference and with interference at least in part by determining differences between the data indicative of two or more of the first primary response, the second primary response, and the third primary response, and also analyzing at least one of the first secondary response, to determine at least one indicator of the cognitive ability of the individual. The programmed processing unit is further configured to execute a first predictive model based at least in part on the at least one indicator to generate a scoring output (such as but not limited to a classification output) indicative of a likelihood of onset of a neurodegenerative condition of the individual and/or a stage of progression of the neurodegenerative condition. As described herein, the first predictive model is trained using a plurality of training datasets, each training dataset corresponding to a previously classified individual of a plurality of individuals, and each training dataset including data representing the at least one indicator of the cognitive ability of the classified individual and data indicative of a diagnosis of a status or progression of the neurodegenerative condition in the classified individual. The trained predictive model can be applied to the at least one indicator of the cognitive ability of the individual (derived from the data indicative of the individual's interactions with the tasks and/or interference executed by the cognitive platform), to generate a scoring output. The scoring output can be used to provide an indication of a likelihood of onset of a neurodegenerative condition and/or a stage of progression of the neurodegenerative condition of an individual.

The example processing unit is also configured, based at least in part on the scoring output (such as but not limited to a classification output), to generate an output to the user interface indicative of one or more of: (i) a likelihood of the individual experiencing an adverse event in response to a change in one or more of a recommended amount, concentration, or dose titration of the pharmaceutical agent, drug, or biologic, (ii) a likelihood of the individual experiencing an adverse event in response to administration of the pharmaceutical agent, drug, or biologic, (iii) a change in the individual's cognitive capabilities, (iv) a recommended a treatment regimen, (v) a recommendation of at least one of a behavioral therapy, counseling, or physical exercise, or (vi) a determination of a degree of effectiveness of at least one of a behavioral therapy, counseling, or physical exercise.

In an example, the processing unit also can be configured to apply a second predictive model (including a second classifier) that is trained to provide a second scoring that is indicative of one or more of: (i) a likelihood of the individual experiencing an adverse event in response to administration of the pharmaceutical agent, drug, or biologic, (ii) a likelihood of the individual experiencing an adverse event in response to a change in one or more of the amount, concentration, or dose titration of the pharmaceutical agent, drug, or biologic, (iii) a change in the individual's cognitive capabilities, (iv), a recommended treatment regimen, (v) a recommendation of at least one of a behavioral therapy, counseling, or physical exercise, (vi) a determination of a degree of effectiveness of at least one of a behavioral therapy, counseling, or physical exercise. The second predictive model can be trained using a plurality of training datasets, where each training dataset is associated with a previously classified individual from a group of individuals. Each training dataset includes data representing the scoring output derived as described herein from the application of a first predictive model to the at least one indicator of the cognitive ability of the classified individual. Each training dataset also includes data indicative of one or more of (i) an indication (including a description) of the adverse event the individual experienced in response to administration of the pharmaceutical agent, drug, or biologic, or in response to a change in one or more of the amount, concentration, or dose titration of that pharmaceutical agent, drug, or biologic, (ii) the treatment regimen of the individual and a rating as to a degree of effectiveness (i.e., a rating of a success or failure) of the regimen in connection with the treatment or management of symptoms of the neurodegenerative condition, (iii) a type and a rating as to a degree of effectiveness (i.e., a rating of a success or failure) of any behavioral therapy, counseling, or physical exercise the individual is undergoing in connection with the treatment or management of symptoms of the neurodegenerative condition. The trained second predictive model can be applied to the scoring output (including a classification output) of the individual (derived from the data indicative of the individual's interactions with the tasks and/or interference executed by the cognitive platform), to generate the second scoring as an output.

In a non-limiting example, the processing unit can be further configured to render a second instance of the task at the user interface, requiring a second response from the individual to the second instance of the task, and analyze a difference between the data indicative of the first response and the second response to compute an interference cost as a measure of at least one additional indication of cognitive abilities of the individual.

In a non-limiting example, based on the results of the analysis of the performance metrics, a medical, healthcare, or other professional (with consent of the individual) can gain a better understanding of potential adverse events which may occur (or potentially are occurring) if the individual is administered a particular type of, amount, concentration, or dose titration of a pharmaceutical agent, drug, biologic, or other medication, including potentially affecting cognition.

In a non-limiting example, a searchable database is provided herein that includes data indicative of the results of the analysis of the performance metrics (including a condition indicator) for particular individuals, along with known levels of efficacy of at least one types of pharmaceutical agent, drug, biologic, or other medication experienced by the individuals in interacting with the cognitive platform, and/or quantifiable information on one or more adverse events experienced by the individual with administration of the at least one types of pharmaceutical agent, drug, biologic, or other medication. The searchable database can be configured to provide metrics for use to determine whether a given individual is a candidate for benefiting from a particular type of pharmaceutical agent, drug, biologic, or other obtained for the individual in interacting with the task and/or interference rendered at the computing device, and/or the scoring output (such as but not limited to a classification output) generated using the predictive model, and/or a level of expression of one or more of an amyloid, an cystatin, an alpha-synuclein, a huntingtin protein, a tau protein, or an apolipoprotein, and/or an indicator of efficacy of an administered drug, biologic or other pharmaceutical agent (such as but not limited to one or more of methylphenidate (MPH), scopolamine, donepezil hydrochloride, rivastigmine tartrate, memantine HCl, solanezumab, aducanumab, or crenezumab) in the individual's interaction(s) with the cognitive platform.

As a non-limiting example, performance metrics can assist with identifying whether the individual is a candidate for a particular type of drug (such as but not limited to a stimulant, e.g., methylphenidate or amphetamine) or whether it might be beneficial for the individual to have the drug administered in conjunction with a regiment of specified repeated interactions with the tasks and/or interference rendered to the computing device. Other non-limiting examples of a biologic, drug or other pharmaceutical agent applicable to any example described herein include methylphenidate (MPH), scopolamine, donepezil hydrochloride, rivastigmine tartrate, memantine HCl, solanezumab, aducanumab, and crenezumab.

In a non-limiting example, based on the results of the analysis of the performance metric (including a condition indicator), a medical, healthcare, or other professional (with consent of the individual) can gain a better understanding of potential adverse events which may occur (or potentially are occurring) if the individual is administered a different amount, concentration, or dose titration of a pharmaceutical agent, drug, biologic, or other medication, including potentially affecting cognition.

In any example implementation, data and other information from an individual is collected, transmitted, and analyzed with their consent.

As a non-limiting example, the cognitive platform described in connection with any example system, method and apparatus herein, including a cognitive platform based on interference processing, can be based on or include the Project: EVO™ platform by Akili Interactive Labs, Inc., Boston, Mass.

Non-Limiting Example Tasks and Interference

Following is a summary of reported results showing the extensive physiological, behavioral, and cognitive measurements data and analysis of the regions of the brain, neural activity, and/or neural pathways mechanisms involved (e.g., activated or suppressed) as an individual interact with stimuli under differing cognitive or emotional load. The articles also described the differences that can be sensed and quantifiably measured based on the individual's performance at cognitive tasks versus stimuli with computer-implemented time-varying elements.

Based on physiological and other measurements, regions of the brain implicated in emotional processing, cognitive tasks, and tasks, are reported. For example, in the review article by Pourtois et al., 2013, "Brain mechanisms for emotional influences on perception and attention: What is magic and what is not," Biological Psychology, 92, 492-512, it is reported that the amygdala monitors the emotional value of stimuli, projects to several other areas of the brain, and sends feedback to sensory pathways (including striate and extrastriate visual cortex). It is also reported that, due to an individual's limited processing capacity, the individual cannot fully analyze simultaneous stimuli in parallel, and these stimuli compete for processing resources in order to gain access to higher cognitive stages and awareness of the individual. With an individual having to direct attention to the location or features of a given stimulus, neural activity in brain regions representing this stimulus increases, at the expense of other concurrent stimuli. Pourtois et al. indicates that this phenomenon has been extensively demonstrated by neuronal recordings as well as imaging methods (EEG, PET, fMRI), and attributed to a gain control. Pourtois et al. concludes that emotion signals may enhance processing efficiency and competitive strength of emotionally significant events through gain control mechanisms similar to those of other attentional systems, but mediated by distinct neural mechanisms in the amygdala and interconnected prefrontal areas, and indicate that alterations in these brain mechanisms might be associated with psychopathological conditions, such as anxiety or phobia. It is also reported that anxious or depressed patients can show maladaptive attentional biases towards negative information. Pourtois et al. also reports that imaging results from EEG and fMRI support a conclusion that the processing of emotional (such as fearful or threat-related) stimuli yields a gain control effect in the visual cortex and the emotional gain control effect can account for the more efficient processing of threat-related stimuli, in addition to or in parallel with any concurrent modulation by other task-dependent or exogenous stimulus-driven mechanisms of attention (see also Brosch et al., 2011, "Additive effects of emotional, endogenous, and exogenous attention: behavioral and electrophysiological evidence," *Neuropsychologia* 49, 1779-1787).

During selective visual attention tests, EEG measurements can provide useful results in the modulation of the gamma band. (See, e.g., Müller et al., (2000). "Modulation of induced gamma band activity in the human EEG by attention and visual information processing." International Journal of Psychophysiology 38.3: 283-299).

There are also studies showing modification in the EEG alpha band signal during attentional shifts. (See, e.g., Sauseng et al. (2005) "A shift of visual spatial attention is selectively associated with human EEG alpha activity." European Journal of Neuroscience 22.11: 2917-2926.) The P300 event-related potential (ERP) also provides data cues about attention. For example, Naatanen et al., (1978) "Early selective-attention effect on evoked potential reinterpreted", Acta Psychologica, 42, 313-329, discloses studies of the auditory attention, which show that the evoked potential has an improved negative response when a subject is presented with infrequent stimuli as compared to frequent stimuli. Naatanen et al discloses that this negative component, called the mismatch negativity, occurs 100 to 200 ms after the stimuli, a time which is perfectly in the range of the pre-attentive attention phase.

As described hereinabove, emotional processing and cognitive processing each require interactions within and among specific brain networks. The degree to which a cognitive assessment, monitor, or treatment is successful can depend on the degree of user engagement, attention, and focus. Major depressive disorder and other similar or related disorders can be associated with changes to cognitive capabilities in multiple cognitive domains including attention (concentration), memory (learning), decision making (judgment), comprehension, judgment, reasoning, understanding, learning, and remembering. The cognitive changes associated with depression can contribute to some of the disabilities experienced by individuals with this disorder.

As described hereinabove, the individual's response to a stimulus can vary depending on the state of the individual, including based on the individual's cognitive condition, disease, or executive function disorder. Measurements of the individual's performance can provide insight into the individual's status relative to a cognitive condition, disease, or executive function disorder, including the likelihood of onset and/or stage of progression of the cognitive condition, disease, or executive function disorder.

The foregoing non-limiting examples of physiological measurement data, behavioral data, and other cognitive data, show that the responses of an individual to tasks can differ based on the type of stimuli. Furthermore, the foregoing examples indicate that the degree to which an individual is affected by a computer-implemented time-varying element, and the degree to which the performance of the individual at a task is affected in the presence of the computer-implemented time-varying element, is dependent on the degree to which the individual exhibits a form of emotional or affective bias. As described herein, the differences in the individual's performance may be quantifiably sensed and measured based on the performance of the individual at cognitive tasks versus stimuli with computer-implemented time-varying elements (e.g., emotional or affective elements). The reported physiological measurement data, behavioral data, and other cognitive data, also show that the cognitive or emotional load evoked by a stimulus can vary depending on the state of an individual, including based on the individual's cognitive condition, disease state, or presence or absence of executive function disorder. As described herein, measurements of the differences in the individual's performance at cognitive tasks versus stimuli with computer-implemented time-varying elements can provide quantifiable insight into the likelihood of onset and/or stage of progression of a cognitive condition, disease, and/or executive function disorder, in the individual, such as but not limited to, social anxiety, depression, bipolar disorder, major depressive disorder, post-traumatic stress disorder, schizophrenia, autism spectrum disorder, attention deficit hyperactivity disorder, dementia, Parkinson's disease, Huntington's disease, or other neurodegenerative condition, Alzheimer's disease, or multiple-sclerosis.

The effects of interference processing on the cognitive control abilities of individuals has been reported. See, e.g., A. Anguera, Nature 501, p. 97 (Sep. 5, 2013) (the "Nature article"). See, also, U.S. Publication No. 20140370479A1 (U.S. application Ser. No. 13/879,589), filed on Nov. 10, 2011, which is incorporated herein by reference. Some of those cognitive abilities include cognitive control abilities in the areas of attention (selectivity, sustainability, etc.), working memory (capacity and the quality of information maintenance in working memory) and goal management (ability to effectively parallel process two attention-demanding tasks or to switch tasks). As an example, children diagnosed with ADHD (attention deficit hyperactivity disorder) exhibit difficulties in sustaining attention. Attention selectivity was found to depend on neural processes involved in ignoring goal-irrelevant information and on processes that facilitate the focus on goal-relevant information. The publications report neural data showing that when two objects are simultaneously placed in view, focusing attention on one can pull visual processing resources away from the other. Studies were also reported showing that memory depended more on effectively ignoring distractions, and the ability to maintain information in mind is vulnerable to interference by both distraction and interruption. Interference by distraction can be, e.g., an interference that is a non-target, that distracts the individual's attention from the primary task, but that the instructions indicate the individual is not to respond to. Interference by interruption/interruptor can be, e.g., an interference that is a target or two or more targets, that also distracts the individual's attention from the primary task, but that the instructions indicate the individual is to respond to (e.g., for a single target) or choose between/among (e.g., a forced-choose situation where the individual decides between differing degrees of a feature).

There were also fMRI results reported showing that diminished memory recall in the presence of a distraction can be associated with a disruption of a neural network involving the prefrontal cortex, the visual cortex, and the hippocampus (involved in memory consolidation). Prefrontal cortex networks (which play a role in selective attention) can be vulnerable to disruption by distraction. The publications also report that goal management, which requires cognitive control in the areas of working memory or selective attention, can be impacted by a secondary goal that also demands cognitive control. The publications also reported data indicating beneficial effects of interference processing as an intervention with effects on an individual's cognitive abilities, including to diminish the detrimental effects of distractions and interruptions. The publications described cost measures that can be computed (including an interference cost) to quantify the individual's performance, including to assess single-tasking or multitasking performance.

An example cost measure disclosed in the publications is the percentage change in an individual's performance at a single-tasking task as compared to a multi-tasking task, such that greater cost (that is, a more negative percentage cost) indicates increased interference when an individual is engaged in single-tasking vs multi-tasking. The publications describe an interference cost determined as the difference between an individual's performance on a primary task in isolation versus a primary task with one or more interference applied, where the interference cost provide an assessment of the individual's susceptibility to interference.

The tangible benefits of computer-implemented interference processing are also reported. For example, the Nature paper states that multi-tasking performance assessed using computer-implemented interference processing was able to quantify a linear age-related decline in performance in adults from 20 to 79 years of age. The Nature paper also reports that older adults (60 to 85 years old) who interacted with an adaptive form of the computer-implemented interference processing exhibited reduced multitasking costs, with the gains persisting for six (6) months. The Nature paper also reported that age-related deficits in neural signatures of cognitive control, as measured with electroencephalography, were remediated by the multitasking training (using the computer-implemented interference processing), with enhanced midline frontal theta power and frontal-posterior theta coherence. Interacting with the computer-implemented interference processing resulted in performance benefits that extended to untrained cognitive control abilities (enhanced sustained attention and working memory), with an increase in midline frontal theta power predicting a boost in sustained attention and preservation of multitasking improvement six (6) months later.

The example systems, methods, and apparatus according to the principles herein are configured to classify an individual as to cognitive abilities and/or to enhance those cognitive abilities based on implementation of interference processing using a computerized cognitive platform. The example systems, methods, and apparatus are configured to implement a form of multi-tasking using the capabilities of a programmed computing device, where an individual is required to perform a primary task and an interference substantially simultaneously, where the task and/or the interference includes a computer-implemented time-varying element, and the individual is required to respond to the computer-implemented time-varying element. The sensing and measurement capabilities of the computing device are configured to collect data indicative of the physical actions taken by the individual during the response execution time to respond to the task at substantially the same time as the computing device collects the data indicative of the physical actions taken by the individual to respond to the computer-implemented time-varying element. The capabilities of the computing devices and programmed processing units to render the task and/or the interference in real time to a user interface, and to measure the data indicative of the individual's responses to the task and/or the interference and the computer-implemented time-varying element in real time and substantially simultaneously can provide quantifiable measures of an individual's cognitive capabilities. In some examples, the computing devices and programmed processing units are configured to rapidly switch to and from different tasks and interferences. In some examples, the computing devices and programmed processing units are configured to perform multiple, different, tasks or interferences in a row (including for single-tasking, where the individual is required to perform a single type of task for a set period of time).

In some examples herein, the task and/or interference includes a response deadline, such that the user interface imposes a limited time period for receiving at least one type of response from the individual interacting with the apparatus or computing device. For example, the period of time that an individual is required to interact with a computing device or other apparatus to perform a primary task and/or an interference can be a predetermined amount of time, such as but not limited to about 30 seconds, about 1 minute, about 4 minutes, about 7 minutes, about 10 minutes, or greater than 10 minutes.

The example systems, methods, and apparatus can be configured to implement a form of multi-tasking to provide measures of the individual's capabilities in deciding whether to perform one action instead of another and to activate the rules of the current task in the presence of an interference such that the interference diverts the individual's attention from the task, as a measure of an individual's cognitive abilities in executive function control.

The example systems, methods, and apparatus can be configured to implement a form of single-tasking, where measures of the individual's performance at interacting with a single type of task (i.e., with no interference) for a set period of time (such as but not limited to navigation task only or a target discriminating task only) can also be used to provide measure of an individual's cognitive abilities.

The example systems, methods, and apparatus can be configured to implement sessions that involve differing sequences and combinations of single-tasking and multitasking trials. In a first example implementation, a session can include a first single-tasking trial (with a first type of task), a second single-tasking trial (with a second type of task), and a multi-tasking trial (a primary task rendered with an interference). In a second example implementation, a session can include two or more multi-tasking trials (a primary task rendered with an interference). In a third example implementation, a session can include two or more single-tasking trials (all based on the same type of tasks or at least one being based on a different type of task).

The performance can be further analyzed to compare the effects of two different types of interference (e.g. distraction or interruptor) on the performances of the various tasks. Some comparisons can include performance without interference, performance with distraction, and performance with interruption. The cost of each type of interference (e.g. distraction cost and interruptor/multi-tasking cost) on the performance level of a task is analyzed and reported to the individual.

The interference processing provides a quantifiable way to measure and improve the ability to process interference events (interruptions and distractions). Interference susceptibility is recognized as a limiting factor across global executive function (including attention and memory) and is known to be fragile in multiple diseases. Changes in EEG signals are shown to occurred at neurological loci associated with cognitive control. For example, midline frontal theta (MFT) power as measured by stimulus-locked electroencephalography (EEG) before, during, or after an individual performs the interference processing can provide indications of attention and interference susceptibility.

In any example herein, the interference can be an instance of a secondary task that includes a stimulus that is either a non-target (as a distraction) or a target (as an interruptor), or a stimulus that is differing types of targets (e.g., differing degrees of a facial expression or other characteristic/feature difference).

Based on the capability of a programmed processing unit to control the effecting of multiple separate sources (including sensors and other measurement components) and the receiving of data selectively from these multiple different sources at substantially simultaneously (i.e., at roughly the same time or within a short time interval) and in real-time, the example systems, methods, and apparatus herein can be used to collect quantitative measures of the responses form an individual to the task and/or interference, which could not be achieved using normal human capabilities. As a result, the example systems, methods, and apparatus herein can be configured to implement a programmed processing unit to render the interference substantially simultaneously with the task over certain time periods.

In some example implementations, the example systems, methods, and apparatus herein also can be configured to receive the data indicative of the measure of the degree and type of the individual's response to the task substantially simultaneously as the data indicative of the measure of the degree and type of the individual's response to the interference is collected (whether the interference includes a target or a non-target). In some examples, the example systems, methods, and apparatus are configured to perform the analysis by applying scoring or weighting factors to the measured data indicative of the individual's response to a non-target that differ from the scoring or weighting factors applied to the measured data indicative of the individual's response to a target, in order to compute a cost measure (including an interference cost).

In an example systems, methods, and apparatus herein, the cost measure can be computed based on the difference in measures of the performance of the individual at one or more tasks in the absence of interference as compared to the measures of the performance of the individual at the one or more tasks in the presence of interference, where the one or more tasks and/or the interference includes one or more computer-implemented time-varying elements. As described herein, the requirement of the individual to interact with (and provide a response to) the computer-implemented time-varying element(s) can introduce cognitive or emotional load that quantifiably affects the individual's capability at performing the task(s) and/or interference due to the requirement for emotional processing to respond to the computer-implemented time-varying element. In an example, the interference cost computed based on the data collected herein can provide a quantifiable assessment of the individual's susceptibility to interference. The determination the difference between an individual's performance on a task in isolation versus a task in the presence of one or more interference (the task and/or interference including the computer-implemented time-varying element) provides an interference cost metric that can be used to assess and classify cognitive capabilities of the individual. The interference cost computed based on the individuals performance of tasks and/or interference performed can also provide a quantifiable measure of the individual's cognitive condition, disease state, or presence or stage of an executive function disorder, such as but not limited to, Alzheimer's disease, dementia, Parkinson's disease, cerebral amyloid angiopathy, familial amyloid neuropathy, or Huntington's disease.

The example systems, methods, and apparatus herein can be configured to perform the analysis of the individual's susceptibility to interference (including as a cost measure such as the interference cost), as a reiterating, cyclical process. For example, where an individual is determined to have minimized interference cost for a given task and/or interference, the example systems, methods, and apparatus can be configured to require the individual to perform a more challenging task and/or interference (i.e., having a higher difficulty level) until the individual's performance metric indicates a minimized interference cost in that given condition, at which point example systems, methods, and apparatus can be configured to present the individual with an even more challenging task and/or interference until the individual's performance metric once again indicates a minimized interference cost for that condition. This can be repeated any number of times until a desired end-point of the individual's performance is obtained.

As a non-limiting example, the interference cost can be computed based on measurements of the individual's performance at a single-tasking task (without an interference) as compared to a multi-tasking task (with interference), to provide an assessment. For example, an individual's performance at a multi-tasking task (e.g., targeting task with interference) can be compared to their performance at a single-tasking targeting task without interference to provide the interference cost.

Example systems, apparatus and methods herein are configured to analyze data indicative of the degree to which an individual is affected by a computer-implemented time-varying element, and/or the degree to which the performance of the individual at a task is affected in the presence of the computer-implemented time-varying element, to provide performance metric including a quantified indicator of cognitive abilities of the individual. The performance metric can be used as an indicator of the degree to which the individual exhibits a form of emotional or affective bias.

In some example implementations, the example systems, methods, and apparatus herein also can be configured to selectively receive data indicative of the measure of the degree and type of the individual's response to an interference that includes a target stimulus (i.e., an interruptor) substantially simultaneously (i.e., at substantially the same time) as the data indicative of the measure of the degree and type of the individual's response to the task is collected and to selectively not collect the measure of the degree and type of the individual's response to an interference that includes a non-target stimulus (i.e., a distraction) substantially simultaneously (i.e., at substantially the same time) as the data indicative of the measure of the degree and type of the individual's response to the task is collected. That is, the example systems, methods, and apparatus are configured to discriminate between the windows of response of the individual to the target versus non-target by selectively controlling the state of the sensing/measurement components for measuring the response either temporally and/or spatially. This can be achieved by selectively activating or de-activating sensing/measurement components based on the presentation of a target or non-target, or by receiving the data measured for the individual's response to a target and selectively not receiving (e.g., disregarding, denying, or rejecting) the data measured for the individual's response to a non-target.

As described herein, using the example systems, methods, and apparatus herein can be implemented to provide a measure of the cognitive abilities of an individual in the area of attention, including based on capabilities for sustainability of attention over time, selectivity of attention, and reduction of attention deficit. Other areas of an individual's cognitive abilities that can be measured using the example systems, methods, and apparatus herein include affective bias, mood, level of cognitive bias, impulsivity, inhibition, perceptive abilities, reaction and other motor functions, visual acuity, long-term memory, working memory, short-term memory, logic, and decision-making.

As described herein, using the example systems, methods, and apparatus herein can be implemented to adapt the tasks and/or interference (at least one including a computer-implemented time-varying element) from one user session to another (or even from one user trial to another) to enhance the cognitive skills of an individual based on the science of brain plasticity. Adaptivity is a beneficial design element for any effective plasticity-harnessing tool. In example systems, methods, and apparatus, the processing unit is configured to control parameters of the tasks and/or interference, such as but not limited to the timing, positioning, and nature of the stimuli, so that the physical actions of the individual can be recorded during the interaction(s). As described hereinabove, the individual's physical actions are affected by their neural activity during the interactions with the computing device to perform single-tasking and multi-tasking tasks. The science of interference processing shows (based on the results from physiological and behavioral measurements) that the aspect of adaptivity can result in changes in the brain of an individual in response to the training from multiple sessions (or trials) based on neuroplasticity, thereby enhancing the cognitive skills of the individual. The example systems, methods, and apparatus are configured to implement tasks and/or interference with at least one computer-implemented time-varying element, where the individual performs the interference processing. As supported in the published research results described hereinabove, the effect on an individual of performing tasks can tap into novel aspects of cognitive training to enhance the cognitive abilities of the individual.

FIGS. 5A-7D show non-limiting example user interfaces that can be rendered using example systems, methods, and apparatus herein to render the tasks and/or interferences (either or both with computer-implemented time-varying element) for user interactions. The non-limiting example user interfaces of FIGS. 5A-7D also can be used for one or more of: to display instructions to the individual for performing the tasks and/or interferences, interact with the computer-implemented time-varying element, to collect the data indicative of the individual's responses to the tasks and/or the interferences and the computer-implemented time-varying element, to show progress metrics, and to provide analysis metrics.

FIGS. 5A-5D show non-limiting example user interfaces rendered using example systems, methods, and apparatus herein. As shown in FIGS. 5A-5B, an example programmed processing unit can be used to render to the user interfaces (including graphical user interfaces) display features 500 for displaying instructions to the individual for performing the tasks and/or interference, and metric features 502 to show status indicators from progress metrics and/or results from application of analytics to the data collected from the individual's interactions (including the responses to tasks/interferences) to provide the analysis metrics. In any example systems, methods, and apparatus herein, the predictive model can be used to provide the analysis metrics provided as a response output. In any example systems, methods, and apparatus herein, the data collected from the user interactions can be used as input to train the predictive model. As shown in FIGS. 5A-5B, an example programmed processing unit also may be used to render to the user interfaces (including graphical user interfaces) an avatar or other processor-rendered guide 504 that an individual is required to control (such as but not limited to navigate a path or other environment in a visuo-motor task, and/or to select an object in a target discrimination task). As shown in FIG. 5B, the display features 500 can be used to instruct the individual what is expected to perform a navigation task while the user interface depicts (using the dashed line) the type of movement of the avatar or other processor-rendered guide 504 required for performing the navigation task. In an example, the navigation task may include milestone objects 510 that the individual is required to steer an avatar to cross or avoid, in order to determine the scoring. As shown in FIG. 5C, the display features 500 can be used to instruct the individual what is expected to perform a target discrimination task while the user interface depicts the type of object(s) 506 and 508 that may be rendered to the user interface, with one type of object 506 designated as a target while the other type of object 508 that may be rendered to the user interface is designated as a non-target, e.g., by being crossed out in this example. As shown in FIG. 5D, the display features 500 can be used to instruct the individual what is expected to perform both a navigation task as a primary task and a target discrimination as a secondary task (i.e., an interference) while the user interface depicts (using the dashed line) the type of movement of the avatar or other processor-rendered guide 504 required for performing the navigation task, and the user interface renders the object type designated as a target object 506 and the object type designated as a non-target object 508.

The measured data indicative of the individual's response to the single-tasking task rendered as a targeting task can be analyzed to provide quantitative insight into the cognitive domains of perception (detection & discrimination), motor function (detection & discrimination), impulsivity/inhibitory control, and visual working memory. The measured data indicative of the individual's response to the single-tasking task rendered as a navigation task can be analyzed to provide quantitative insight into the cognitive domains of visuomotor tracking and motor function. The measured data indicative of the individual's response to a primary task (rendered as a navigation task) in the presence of an interference (rendered as a targeting task), in a multi-tasking task, can be analyzed to provide quantitative insight into the cognitive domains of divided attention and interference management.

Figure 6A:
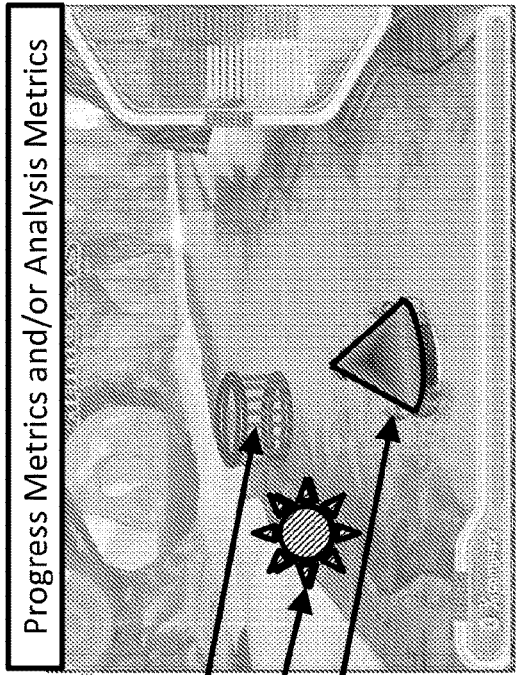
FIGS. 6A-6T show examples of the rendering of tasks and interferences at user interfaces, according to the principles herein.
Figure 6B:
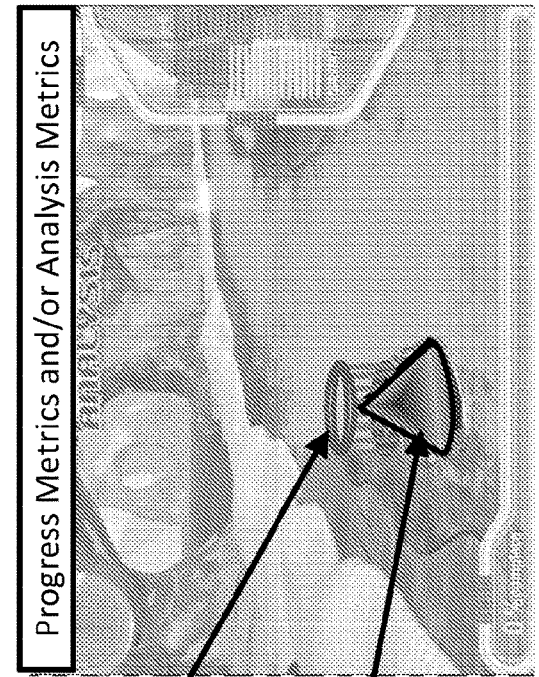
Figure 6C:
Figure 6D:
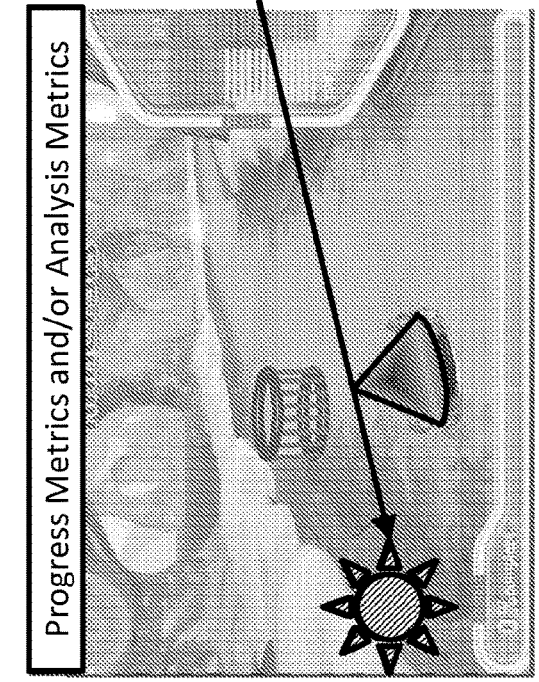
Figure 6E:
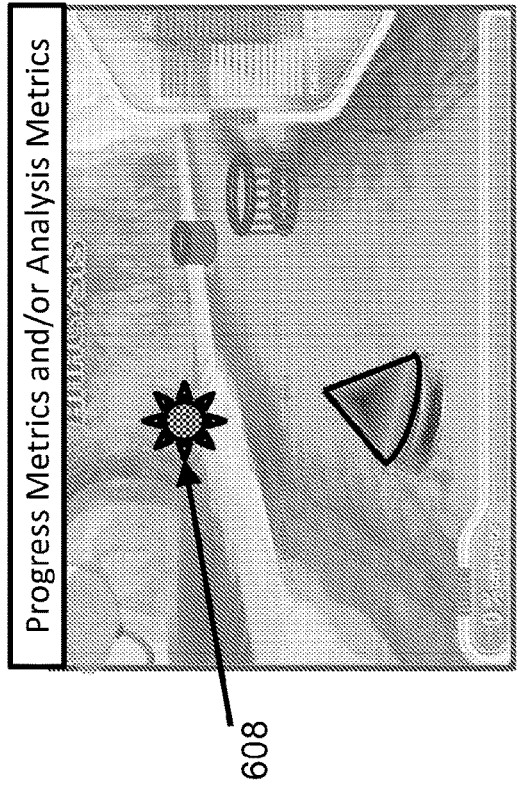
Figure 6G:
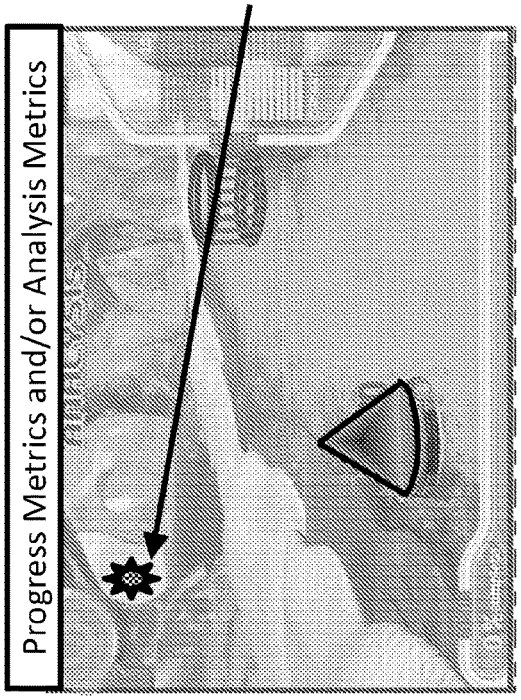
Figure 6F:
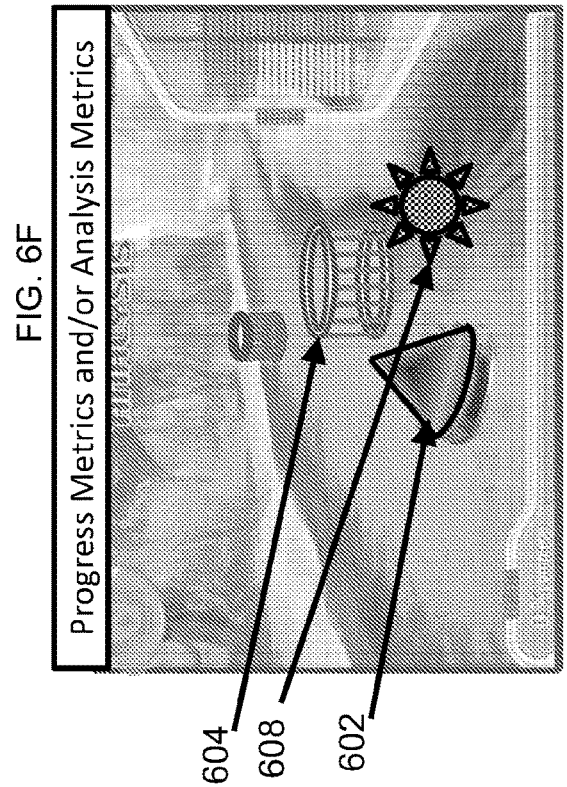
Figure 6H:
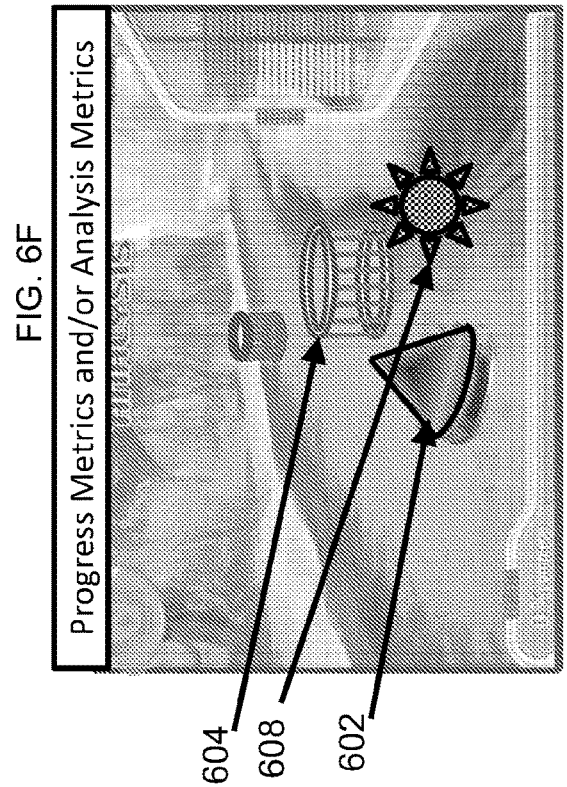
Figure 6I:
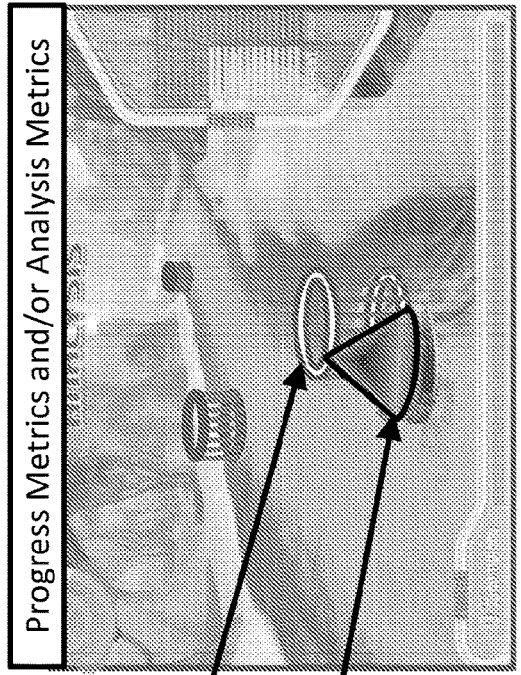
Figure 6J:
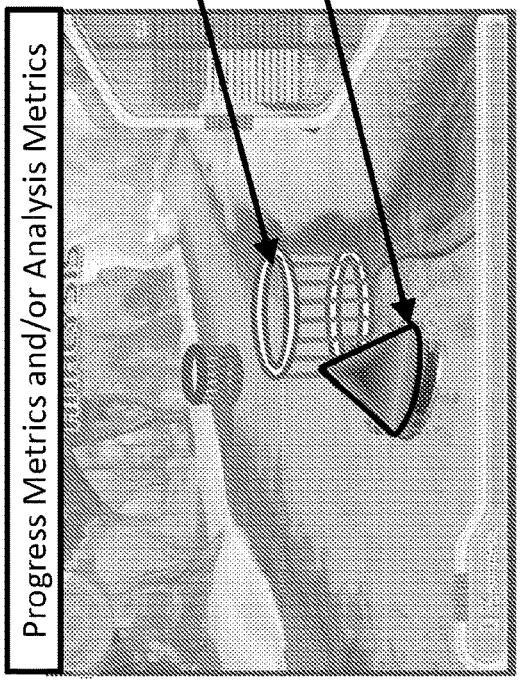
Figure 6K:
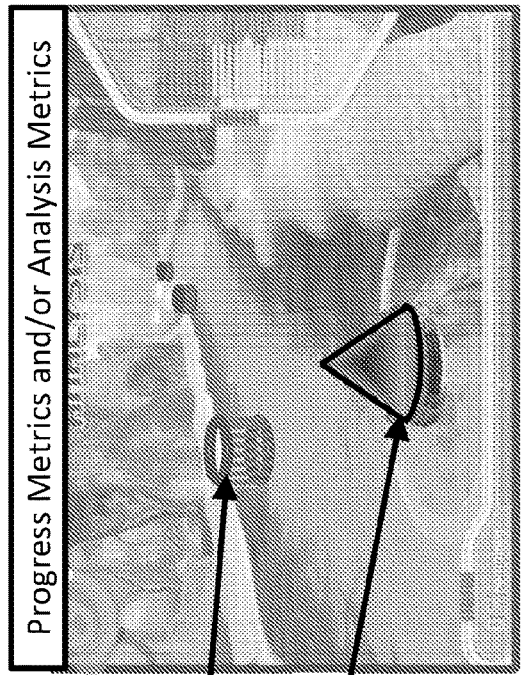
Figure 6L:
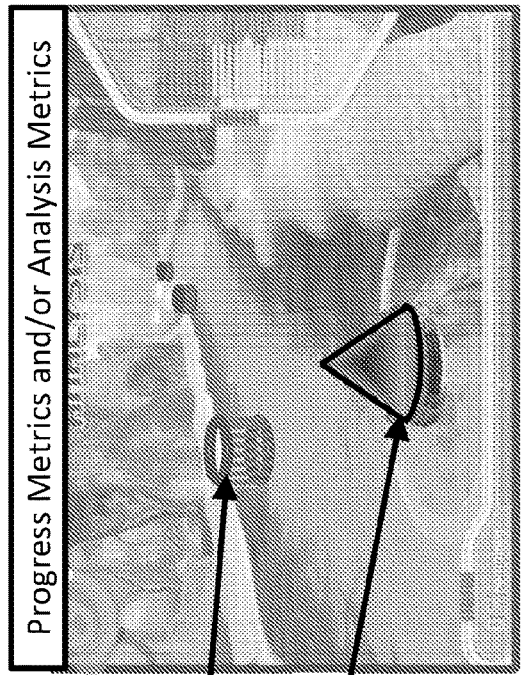
Figure 6M:
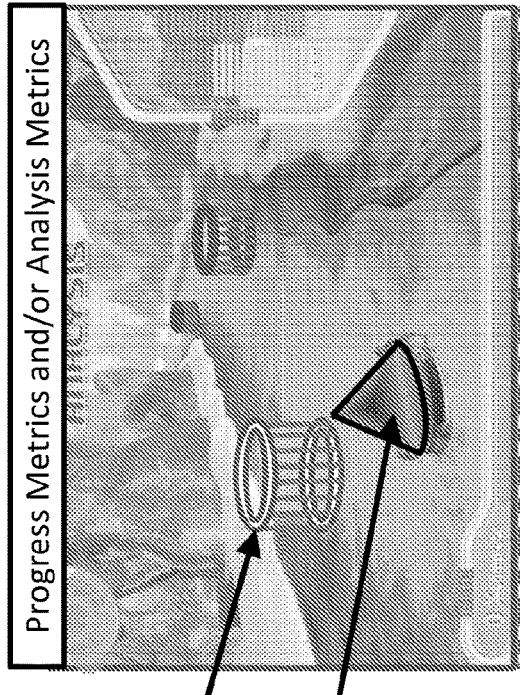
Figure 6N:
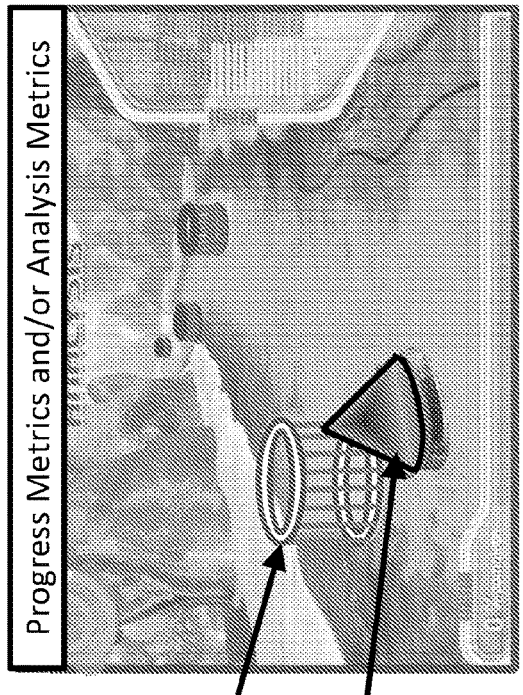
Figure 6O:
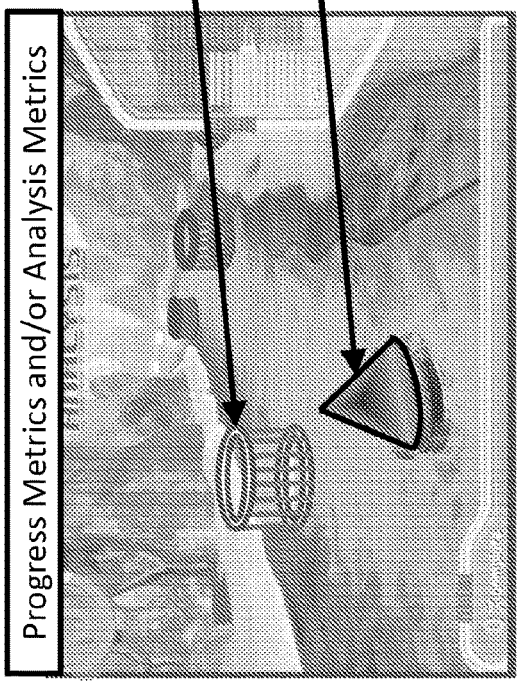
Figure 6P:
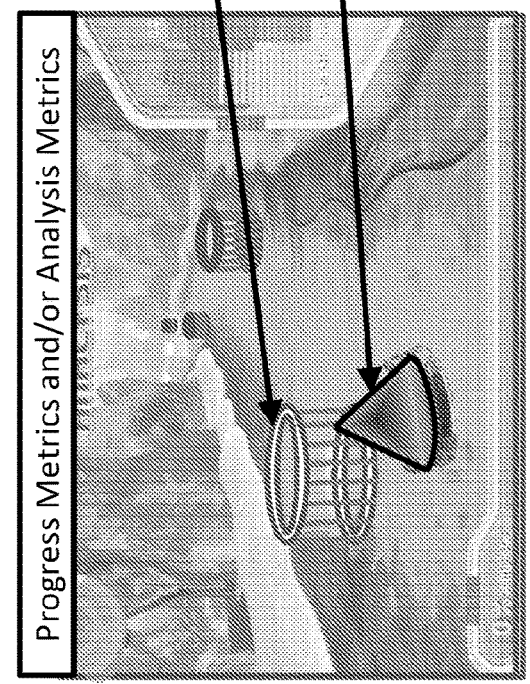
Figure 6Q:
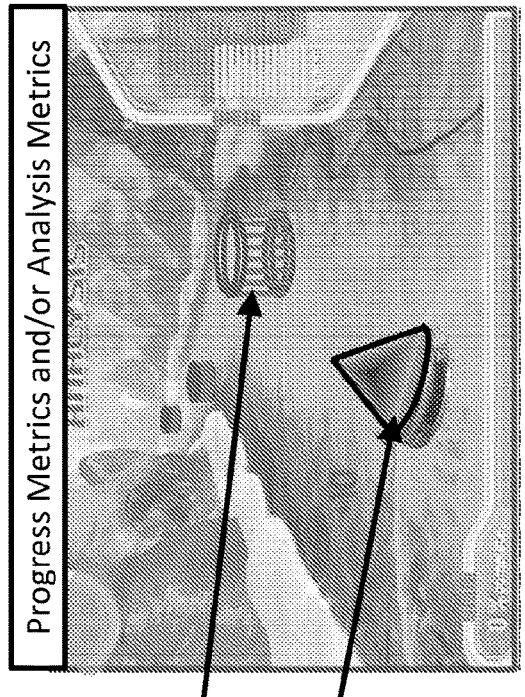
Figure 6R:
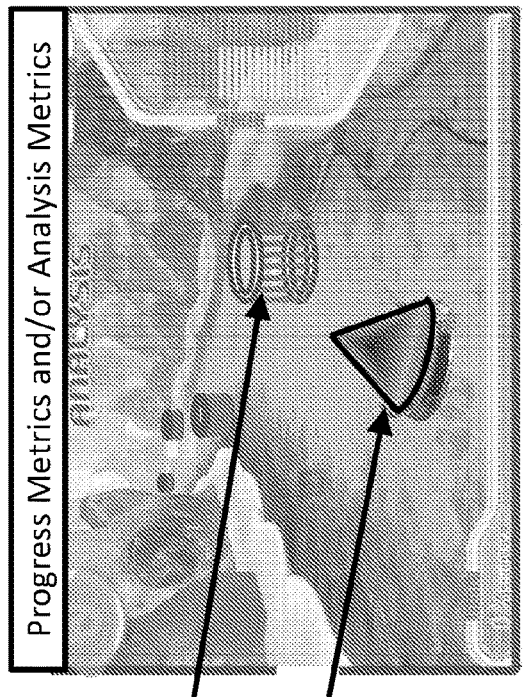
Figure 6S:
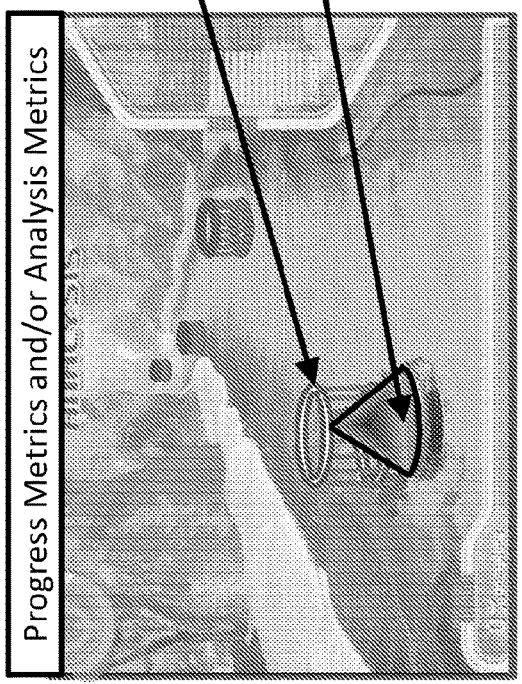
Figure 6T:
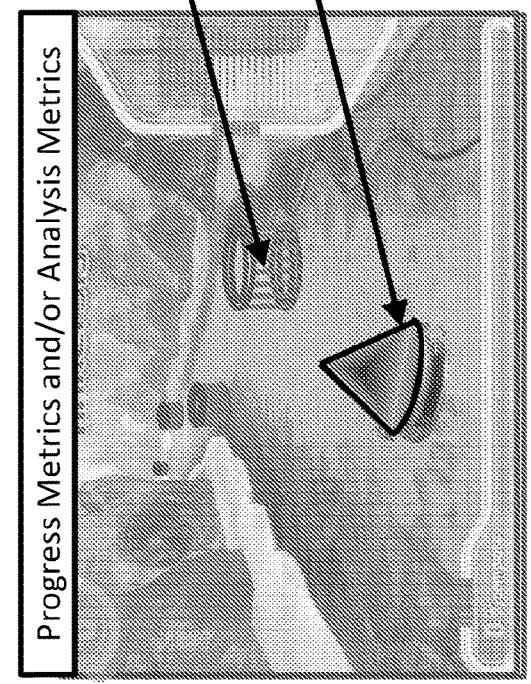
Figure 7A:
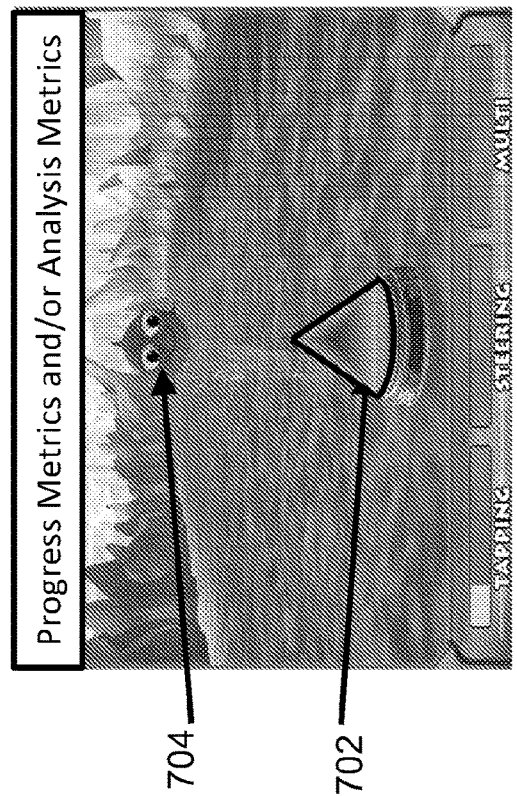
FIGS. 7A-7D show examples of the rendering of tasks and interferences at user interfaces, according to the principles herein.
Figure 7B:
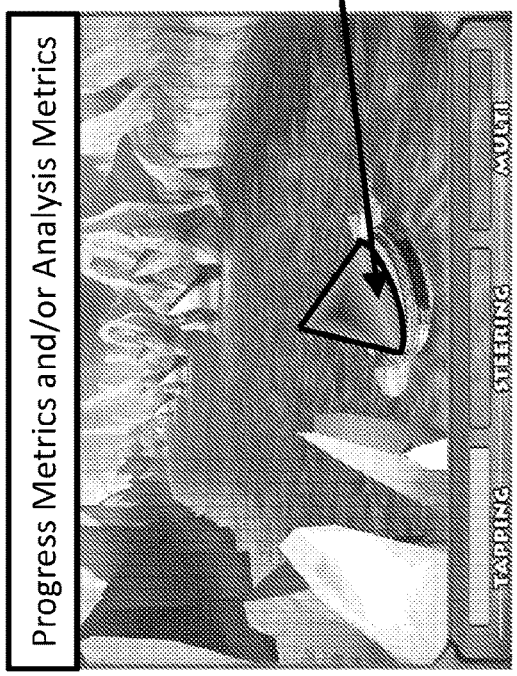
Figure 7C:
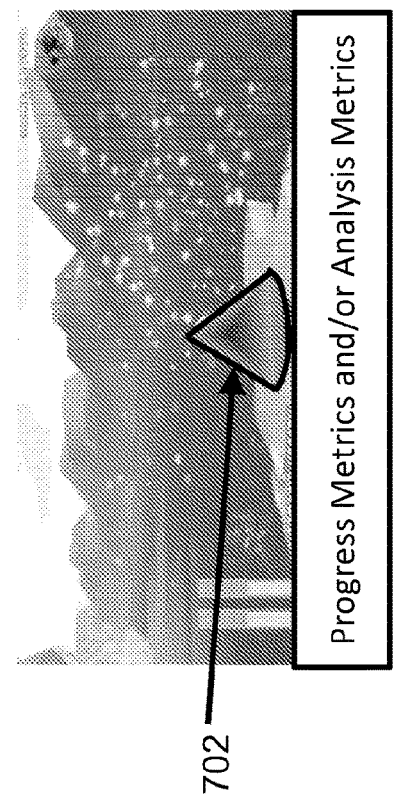
Figure 7D:
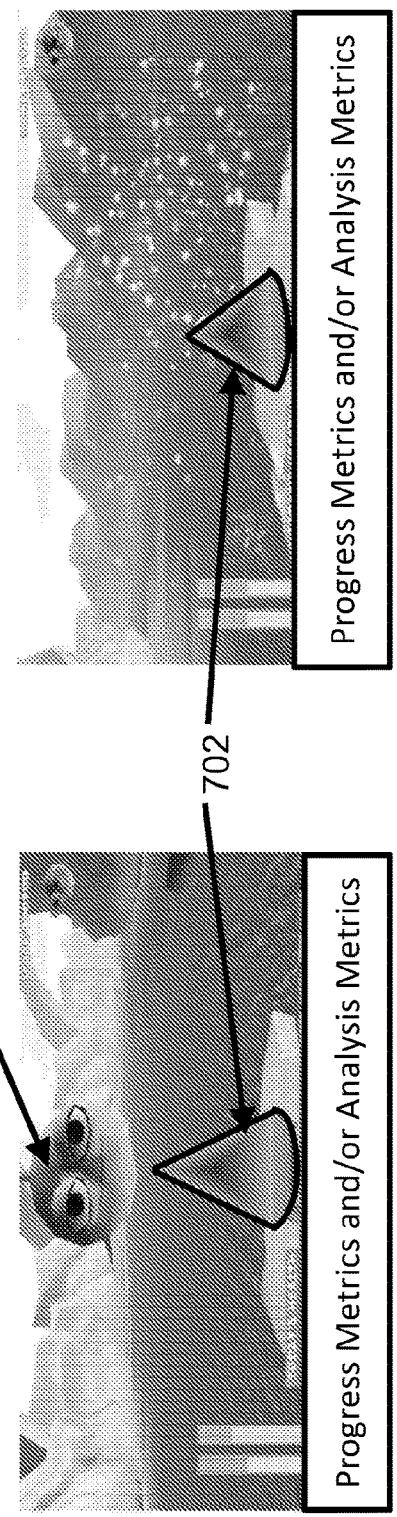

FIGS. 6A-6T show a non-limiting example of the dynamics of tasks and interferences that can be rendered at user interfaces, according to the principles herein. In this example, the primary task is a visuo-motor navigation task, and the interference is target discrimination (as a secondary task). As shown in FIGS. 6D, 6I-6K, and 6O-6Q, the individual is required to perform the navigation task by controlling the motion of the avatar 602 along a path that coincides with the milestone objects 604. FIGS. 6A-6T show a non-limiting example implementation where the individual is expected to actuate an apparatus or computing device (or other sensing device) to cause the avatar 602 to coincide with the milestone object 604 as the response in the navigation task, with scoring based on the success of the individual at crossing paths with (e.g., hitting) the milestone objects 604. In another example, the individual is expected to actuate an apparatus or computing device (or other sensing device) to cause the avatar 602 to miss the milestone object 604, with scoring based on the success of the individual at avoiding the milestone objects 604. FIGS. 6A-6C show the dynamics of a target object 606 (a star having a first type of pattern). FIGS. 6E-6H show the dynamics of a non-target object 608 (a star having a second type of pattern). FIGS. 6I-6T show the dynamics of other portions of the navigation task, where the individual is expected to guide the avatar 602 to cross paths with the milestone object 604 in the absence of an interference (an instance of a secondary task).

In the example of FIGS. 6A-6T, the processing unit of the example system, method, and apparatus is configured to receive data indicative of the individual's physical actions to cause the avatar 602 to navigate the path. For example, the individual may be required to perform physical actions to "steer" the avatar, e.g., by changing the rotational orientation or otherwise moving a computing device. Such action can cause a gyroscope or accelerometer or other motion or position sensor device to detect the movement, thereby providing measurement data indicative of the individual's degree of success in performing the navigation task.

In the example of FIGS. 6A-6C and 6E-6H, the processing unit of the example system, method, and apparatus is configured to receive data indicative of the individual's physical actions to perform the target discrimination task. For example, the individual may be instructed prior to a trial or other session to tap, or make other physical indication, in response to display of a target object 606, and not to tap to make the physical indication in response to display of a non-target object 608. In FIGS. 6A-6C and 6E-6H, the target discrimination task acts as an interference (i.e., an instance of a secondary task) to the primary navigation task, in an interference processing multi-tasking implementation. As described hereinabove, the example systems, methods, and apparatus can cause the processing unit to render a display feature to display the instructions to the individual as to the expected performance. As also described hereinabove, the processing unit of the example system, method, and apparatus can be configured to (i) receive the data indicative of the measure of the degree and type of the individual's response to the primary task substantially simultaneously as the data indicative of the measure of the degree and type of the individual's response to the interference is collected (whether the interference includes a target or a non-target), or (ii) to selectively receive data indicative of the measure of the degree and type of the individual's response to an interference that includes a target stimulus (i.e., an interruptor) substantially simultaneously (i.e., at substantially the same time) as the data indicative of the measure of the degree and type of the individual's response to the task is collected and to selectively not collect the measure of the degree and type of the individual's response to an interference that includes a non-target stimulus (i.e., a distraction) substantially simultaneously (i.e., at substantially the same time) as the data indicative of the measure of the degree and type of the individual's response to the task is collected.

FIGS. 7A-7D show other non-limiting examples of the dynamics of tasks and interferences that can be rendered at user interfaces, according to the principles herein. In this example, the primary task is a visuo-motor navigation task, and the interference is target discrimination (as an instance of a secondary task). Similarly to FIGS. 6A-6T, the individual is required to perform the navigation task by controlling the motion of the avatar 602 along a path. The individual is required to provide a response to the tasks in the presence or absence of an interference 704 (rendered as a target for discrimination).

In a non-limiting example, the adaptation of the difficulty of a task and/or interference may be adapted with each different stimulus that is presented as a computer-implemented time-varying element.

In another non-limiting example, the example system, method, and apparatus herein can be configured to adapt a difficulty level of a task and/or interference one or more times in fixed time intervals or in other set schedule, such as but not limited to each second, in 10 second intervals, every 30 seconds, or on frequencies of once per second, 2 times per second, or more (such as but not limited to 30 times per second).

In a non-limiting example of a visuo-motor task (a type of navigation task), one or more of navigation speed, shape of the course (changing frequency of turns, changing turning radius), and number and/or size of obstacles can be changed to modify the difficulty of a navigation game level, with the difficulty level increasing with increasing speed and/or increasing numbers and/or sizes of obstacles (including types of milestone objects (e.g., some milestone objects to avoid or some milestone objects to cross/coincide with).

In a non-limiting example, the difficulty level of a task and/or interference of a subsequent level can also be changed in real-time as feedback, e.g., the difficulty of a subsequent level can be increased or decreased in relation to the data indicative of the performance of the task.

In an example, the response recorded for the targeting task can be, but is not limited to, a touch, swipe or other gesture relative to a user interface or image collection device (including a touch-screen or other pressure sensitive screen, or a camera) to interact with a user interface. In another example, the response recorded for the targeting task can be, but is not limited to, user actions that cause changes in a position, orientation, or movement of a computing device including the cognitive platform, that is recorded using a sensor disposed in or otherwise coupled to the computing device (such as but not limited to a motion sensor or position sensor).

In this example and any other example herein, the cData and/or nData can be collected in real-time.

In this example and any other example herein, the adjustments to the type of tasks and/or CSIs can be made in real-time.

FIGS. 8A-11 show the results of non-limiting example measurements made using an example system, method, and apparatus described herein.

FIGS. 8A-8B show physiological measurement data (nData) and other data for a set of individuals with ages from 70 years or older (both male and female individuals). The example physiological measurement data include data indicative of an amyloid grouping of the individuals (i.e., whether determined to the amyloid positive (+) or amyloid negative (−)), an ApoEε4 status, standard uptake value ratios (SUVR) computed based on positron emission tomography (PET) imaging data, cortical thickness in signature regions for Alzheimer's disease (AD Signature regions), normalized bilateral hippocampal volumes, normalized bilateral whole-brain volumes, and MRI microbleed count (deep vs. lobar). FIGS. 8A-8B also shows that certain of the individuals are also administered a drug (methylphenidate) as compared to a placebo. None of the structural MRI measures differentiated the populations (i.e., the amyloid positive (+) vs. the amyloid negative (−) individuals).

FIGS. 8A-8B show example data (including nData) which can be used as part of a training dataset for training a predictive model to generate a scoring output indicative of, e.g., amyloid status or APOE expression levels. In another example, FIGS. 8A-8B show the type of data that can be used as part of a training dataset for training another predictive model to generate an output indicative of, e.g., a likelihood of an individual experiencing an adverse event in response to administration of an amount, concentration, or dose titration of the drug methylphenidate, or changes to that amount, concentration, or dose titration of the drug methylphenidate. The example data can be used as part of a training dataset for training a predictive model to generate a scoring output indicative of, e.g., amyloid status or APOE status, or other type of output indicative of a likelihood of the individual experiencing an adverse event in response to administration of the drug methylphenidate, or a likelihood of the individual experiencing an adverse event in response to a change in one or more of the amount, concentration, or dose titration of the drug methylphenidate. The predictive model could also be trained as a classifier to generate a classification output to classify individuals as to amyloid status. The generated indication of amyloid status (whether a scoring output or classification output) may be used to give some insight into the likelihood of onset or stage of progression of Alzheimer's disease.

Figure 9A:
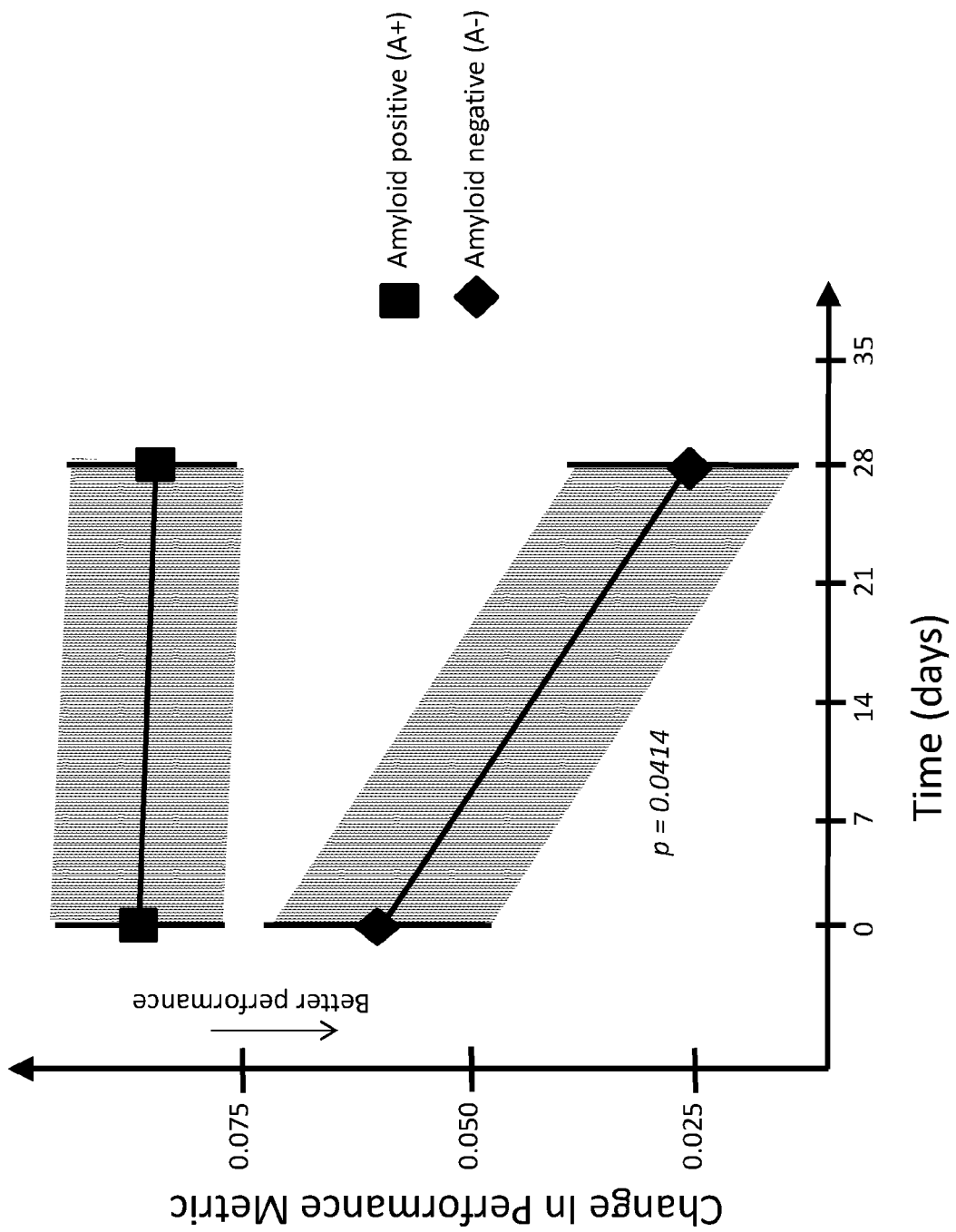
FIGS. 9A-9B show plots of example performance metrics derived from measures of the individuals' performance, according to the principles herein.
Figure 9B:
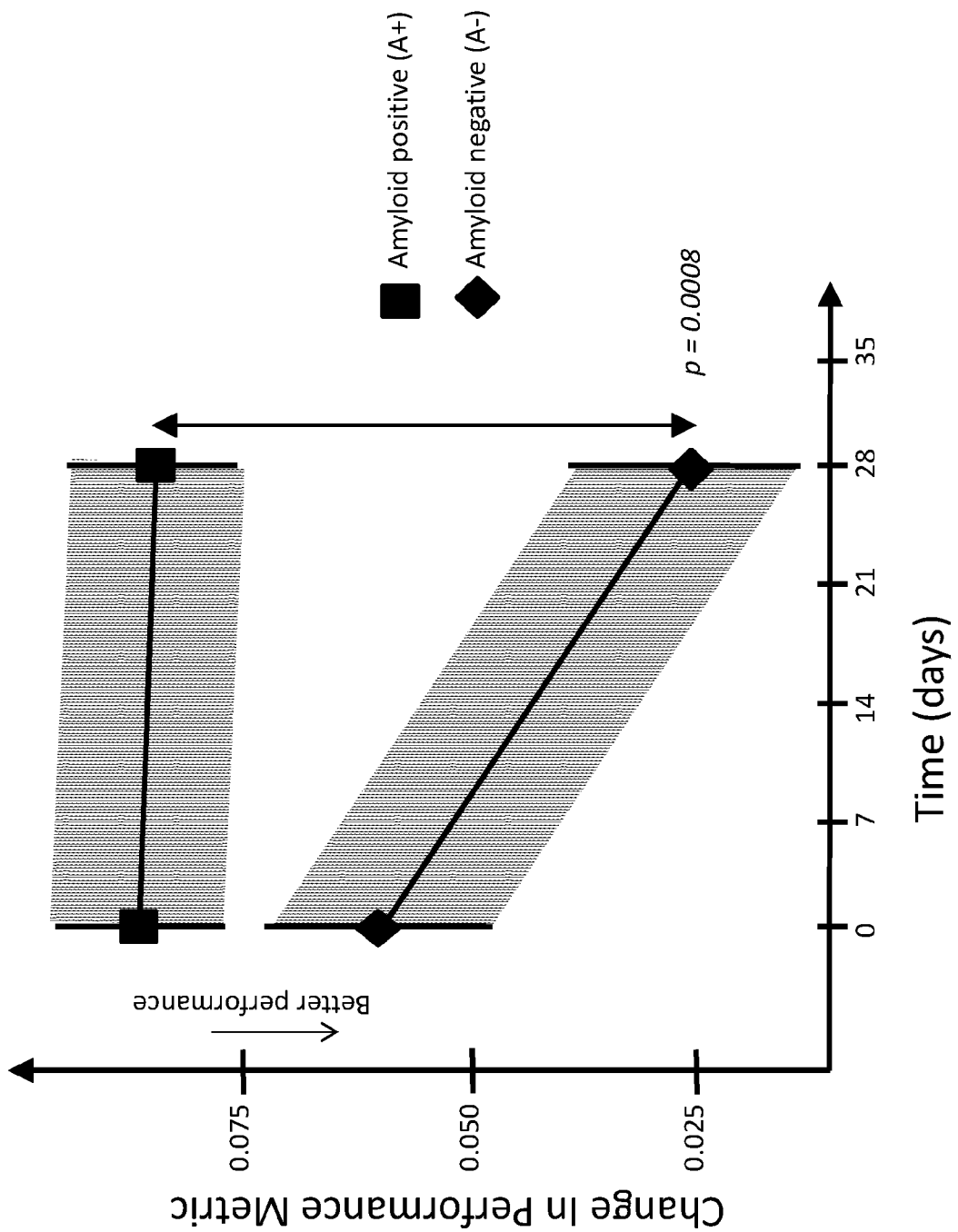

FIGS. 9A-9B show plots of the results of performance metrics computed based on the response data measured from multiple interactions of the individuals (characteristics/measurements summarized in FIGS. 8A-8B) from day 0 to day 28, with an example system or apparatus (configured as a cognitive platform). The analyses are adjusted for the covariates. The computed performance metrics act as indicators, to provide an indication of the effect of the multiple interactions with the cognitive training on divided attention, based on computation of a performance metric (as an interference cost) on reaction time on hits. As shown in FIGS. 9A-9B, the example performance metric act as indicators, to provide an indication of better performance for lower values. The analysis of the data indicates that the amyloid (−) individuals have a measurable (and quantifiably significant) improvement after multiple interactions between day 0 and day 28 days with the example cognitive platform, whereas no measurable statistical change is indicated from the measured response data from the amyloid (+) individuals. After multiple interactions with the example cognitive platform, the effect on divided attention as measured by reaction time on hits show a positive training effect in both populations (p<0.001) in both conditions, with greater reduction in the amyloid (−) population in the performance metric (interference cost) after training (p<0.003). The results indicate that, after multiple interactions with the example cognitive platform, the performance metrics computed based on the individual's interactions provides a distinction in performance metric between individuals having differing amyloid condition, thereby providing a classification of the individuals as to amyloid group. The amyloid status of an individual potentially may be used to correlate with (or at least provide insight into) a potential likelihood of onset of and/or a stage of progression of Alzheimer's disease (a neurodegenerative condition).

Similar analysis described in connection with any one of Impl. 1 through 6 and Table 1 is performed based on the data from the individuals' interactions with the cognitive platform to generate the data shown in FIGS. 8A-8B.

Figure 10:
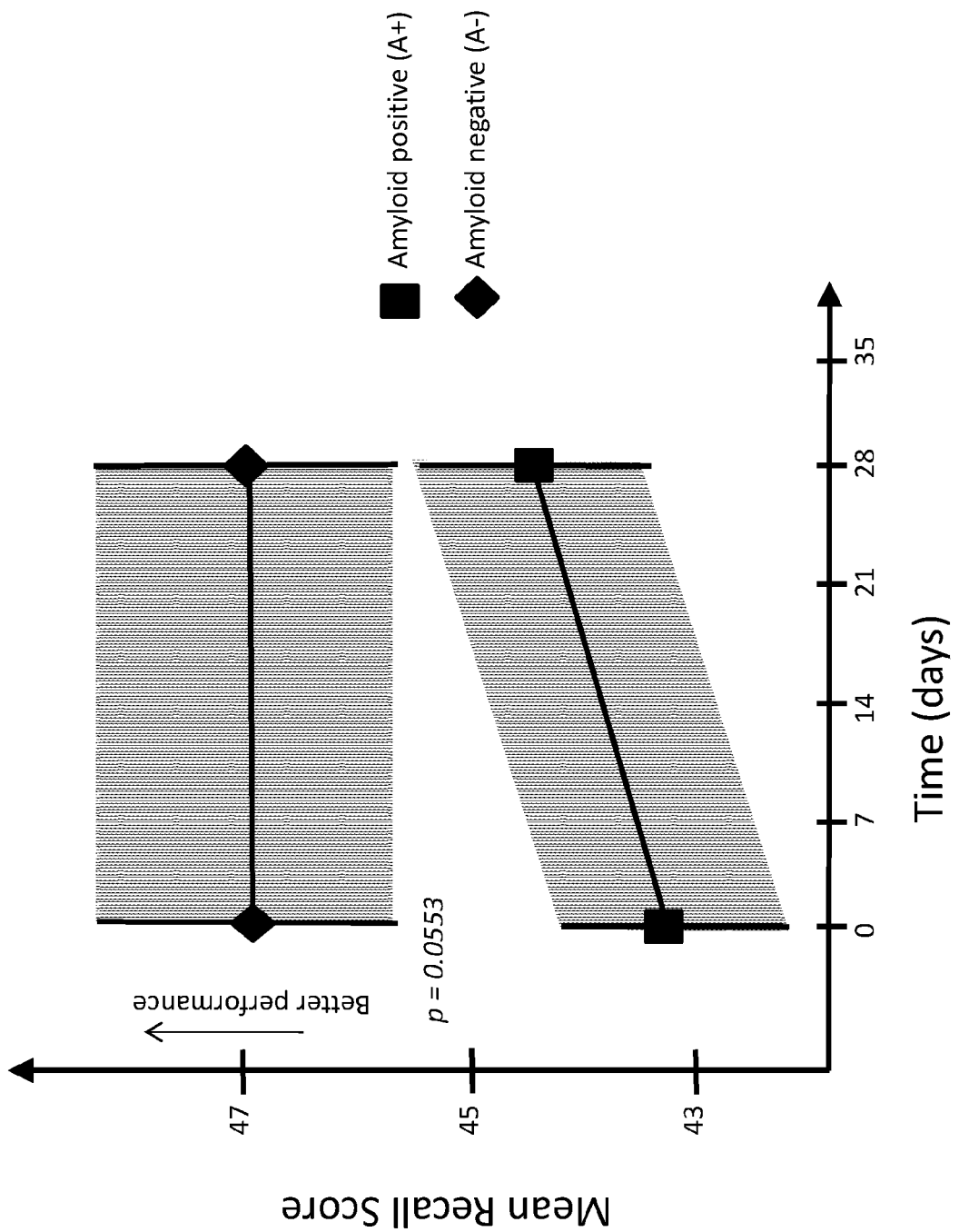
FIG. 10 shows plots of the results of measures of a test for episodic memory, according to the principles herein.

FIG. 10 shows plots of the results of measures from the Rey Auditory Verbal Learning (RAVLT™) test (a test for episodic memory), where some difference is shown between populations (i.e., the amyloid positive (+) vs. the amyloid negative (−) individuals) on the RAVLT™ test on Day 0 (p=0.0553) for total recall score. The RAVLT™ test is observed to provide some differentiation between the amyloid (+) and (−) individuals of the population.

Figure 11:
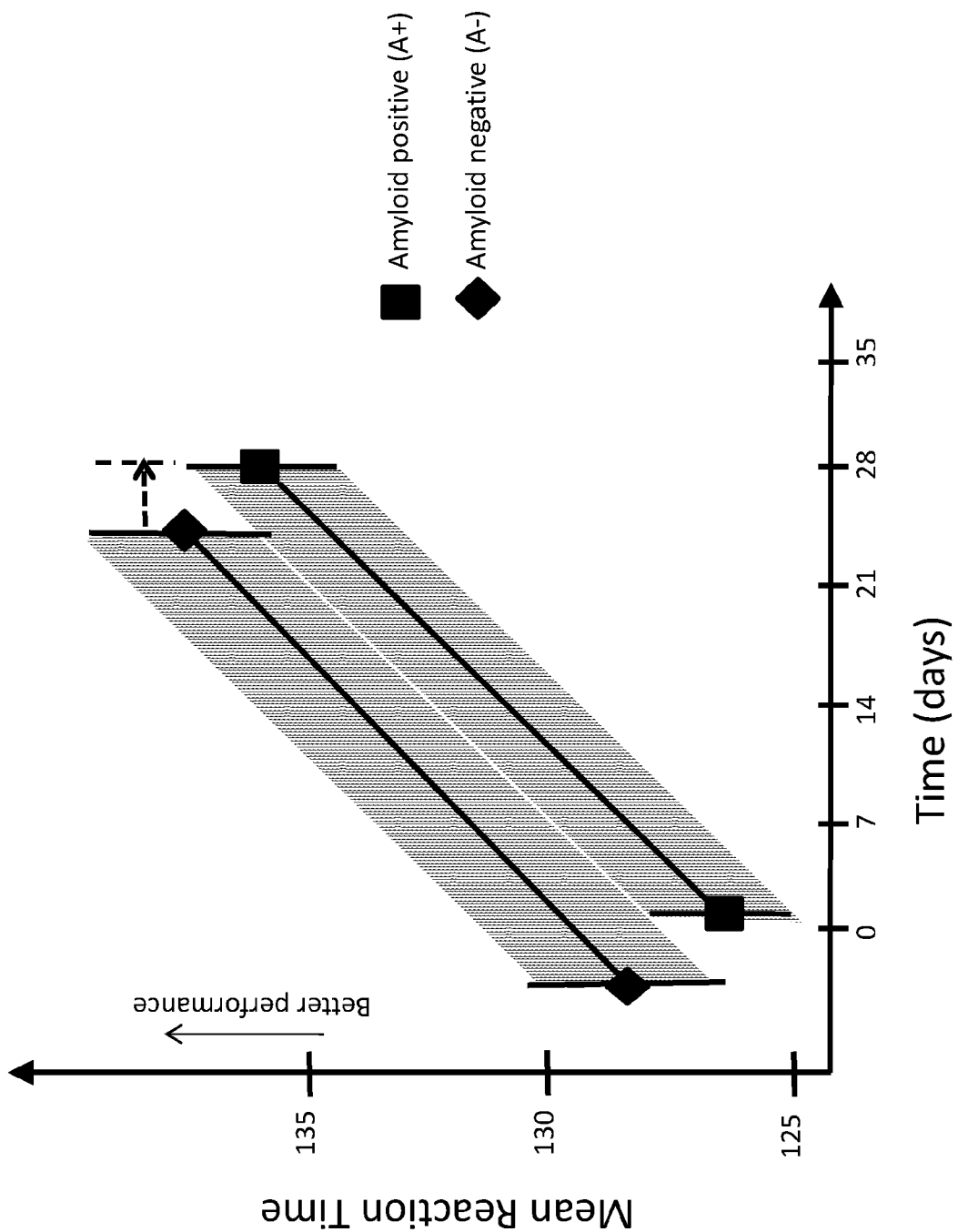
FIG. 11 shows plots of the results of measures of a test for sustained attention, according to the principles herein.

FIG. 11 shows plots of the results of measures from the Test of Variables of Attention (TOVA®) test (a test for sustained attention), where greater performance at Day 28 is observed for both populations p<0.001 (i.e., the amyloid positive (+) vs. the amyloid negative (−) individuals), where the numerical improvement in standardized score are 9.0 for amyloid (−) and 9.4 for amyloid (+). No performance differences are observed between populations at either time point.

Figure 12A:
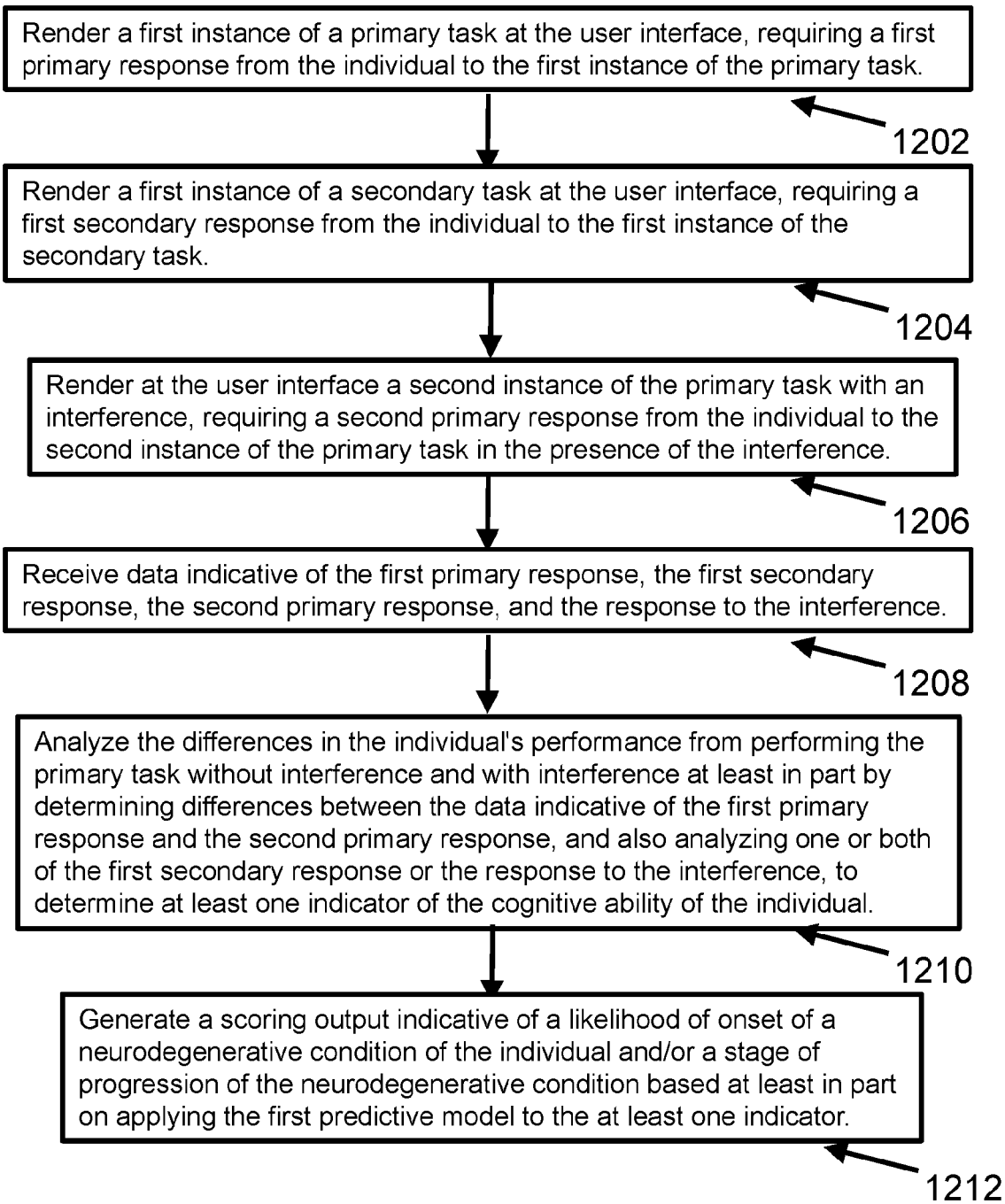

FIG. 12A shows a flowchart of a non-limiting example method that can be implemented using a cognitive platform or platform product that includes at least one processing unit. In block 1202, the at least one processing unit is used to render a first instance of a primary task at the user interface, requiring a first primary response from the individual to the first instance of the primary task. In block 1204, the at least one processing unit is used to render a first instance of a secondary task at the user interface, requiring a first secondary response from the individual to the first instance of the secondary task. In block 1206, the at least one processing unit is used to render at the user interface a second instance of the primary task with an interference, requiring a second primary response from the individual to the second instance of the primary task in the presence of the interference. The interference is configured to divert the individual's attention from the second instance of the primary task, as a second instance of the secondary task that is rendered as an interruptor or a distraction. In the example of FIG. 12A, the user interface can be configured to instruct the individual not to respond to the interference that is configured as a distraction and to respond to the interference that is configured as an interruptor. In block 1208, the at least one processing unit is used to receive data indicative of the first primary response, the first secondary response, the second primary response, and the response to the interference. In block 1210, the user interface can be configured to analyze the differences in the individual's performance from performing the primary task without interference and with interference at least in part by determining differences between the data indicative of the first primary response and the second primary response, and also analyzing one or both of the first secondary response or the response to the interference, to determine at least one indicator of the cognitive ability of the individual. In block 1212, the at least one processing unit is used to generate a scoring output indicative of a likelihood of onset of a neurodegenerative condition of the individual and/or a stage of progression of the neurodegenerative condition based at least in part on applying the first predictive model to the at least one indicator.

Figure 12B:
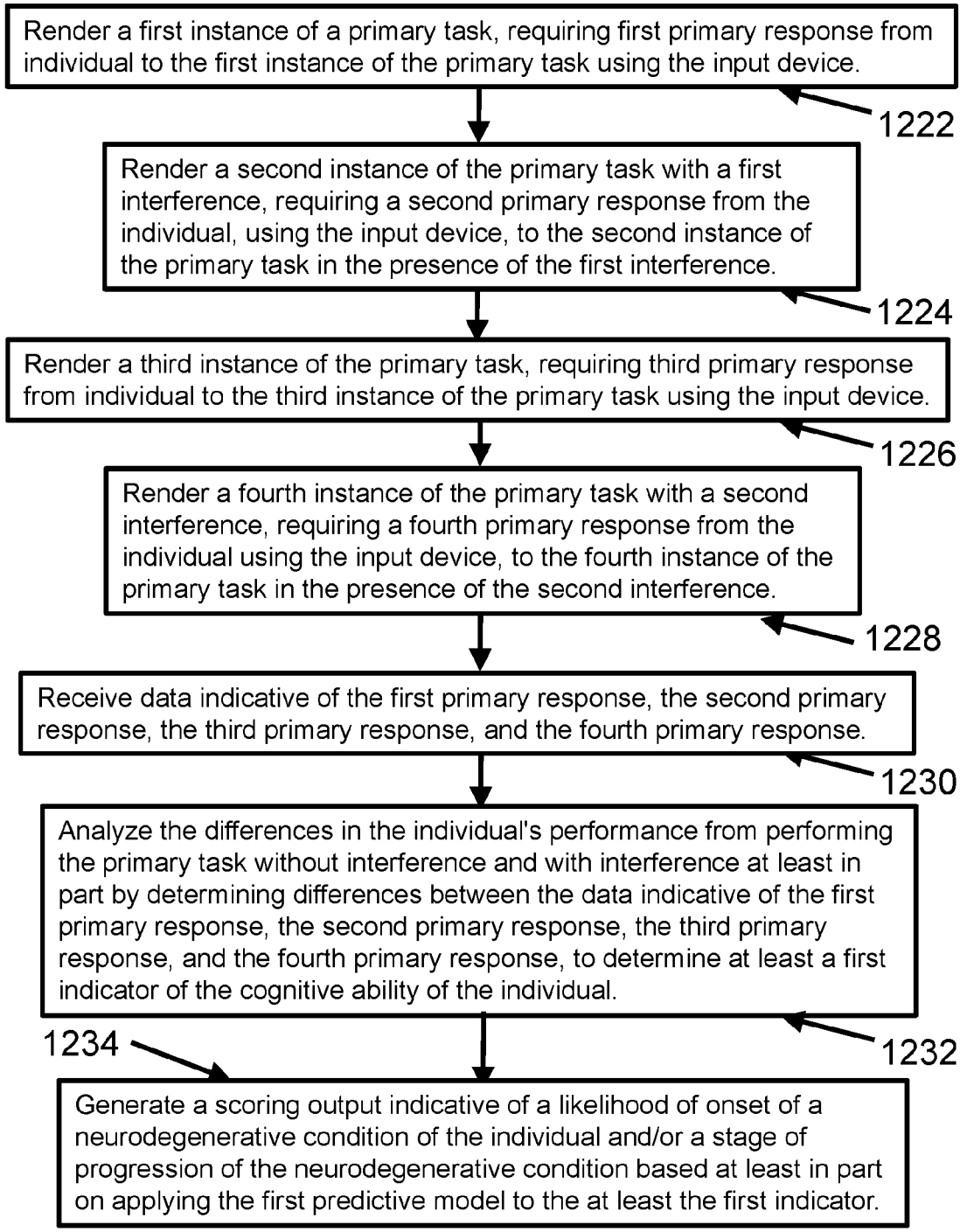

FIG. 12B shows a flowchart of a non-limiting example method that can be implemented using a cognitive platform or platform product that includes at least one processing unit. In block 1222, the at least one processing unit is used to render a first instance of a primary task at the user interface, requiring a first primary response from the individual to the first instance of the primary task. In block 1224, the at least one processing unit is used to render at the user interface a second instance of the primary task with a first interference, requiring a second primary response from the individual to the second instance of the primary task in the presence of the first interference. The first interference is configured to divert the individual's attention from the second instance of the primary task and is rendered as an interruptor or a distraction. In block 1226, the at least one processing unit is used to render a third instance of the primary task at the user interface, requiring a third primary response from the individual to the third instance of the primary task. In block 1228, the at least one processing unit is used to render at the user interface a fourth instance of the primary task with a second interference, requiring a fourth primary response from the individual to the fourth instance of the primary task in the presence of the second interference. The second interference is configured to divert the individual's attention from the fourth instance of the primary task and is rendered as an interruptor or a distraction. In the example of FIG. 12B, the user interface can be configured to instruct the individual not to respond to an interference (whether the first or the second interference) that is configured as a distraction and to respond to the interference (whether the first or the second interference) that is configured as an interruptor. In block 1230, the at least one processing unit is used to receive data indicative of the first primary response, the second primary response, the third primary response, and the fourth primary response. In block 1232, the at least one processing unit is used to analyze the differences in the individual's performance from performing the primary task without interference and with interference at least in part by determining differences between the data indicative of the first primary response and the second primary response, and analyzing one or both of the first secondary response or the response to the interference, to determine at least one indicator of the cognitive ability of the individual. In block 1234, the at least one processing unit is used to generate a scoring output indicative of a likelihood of onset of a neurodegenerative condition of the individual and/or a stage of progression of the neurodegenerative condition based at least in part on applying the first predictive model to the at least the first indicator.

FIGS. 12C-1-12C-2 show a flowchart of a non-limiting example method that can be implemented using a cognitive platform or platform product that includes at least one processing unit. In block 1252, the at least one processing unit is used to render at least one user interface to present a computerized stimuli or interaction (CSI) or other interactive elements to the user, or cause an actuating component of the cognitive platform or platform product to effect auditory, tactile, or vibrational computerized elements (including CSIs) to effect the stimulus or other interaction with a user. In block 1254, the at least one processing unit is used to cause a component of the program product to receive data indicative of at least one user response based on the user interaction with the CSI or other interactive element (such as but not limited to cData). In an example where at least one user interface is rendered to present the computerized stimuli or interaction (CSI) or other interactive elements to the user, the at least one processing unit can be programmed to cause the user interface to receive the data indicative of the at least one user response. In block 1256, the at least one processing unit is used to cause a component of the program product to receive nData indicative of the measurements made using the one or more nData components (including the one or more physiological or monitoring components and/or cognitive testing components) before, during, and/or after the user interacts with the cognitive platform. In an example implementation of the method, block 1254 may be performed in a similar timeframe, or substantially simultaneously with block 1256. In another example implementation of the method, block 1254 may be performed at different timepoints than block 1256. In block 1258, the at least one processing unit also is used to: analyze the cData and/or nData to provide a measure of the individual's physiological condition and/or cognitive condition, and/or analyze the differences in the individual's performance based on determining the differences between the user's responses (including based on differences in the cData) and differences in the associated the nData, and/or adjust the difficulty level of the task(s) including the computerized stimuli or interaction (CSI) or other interactive elements based on the analysis of the cData and/or nData (including the measures of the individual's performance and/or physiological condition determined in the analysis), and/or provide an output or other feedback from the platform product that can be indicative of the individual's performance, and/or cognitive assessment, and/or response to cognitive treatment, and/or assessed measures of cognition, and/or to classify an individual as to amyloid group, and/or APOE expression group (or other expression group based on the expression level of other protein(s) that can be of clinical interest in a neurodegenerative condition), and/or potential efficacy of use of the cognitive platform or platform product when the individual is administered a drug, biologic or other pharmaceutical agent, and/or an expected score from the individual's performance of a TOVA® test and/or a RAVLT™ test, and/or to classify an individual as to likelihood of onset and/or stage of progression of a neurodegenerative condition, and/or to determine a change in dosage of a drug, biologic or other pharmaceutical agent to the individual or to determine an optimal type or combination of drug, biologic or other pharmaceutical agent to the individual.

Figure 13:
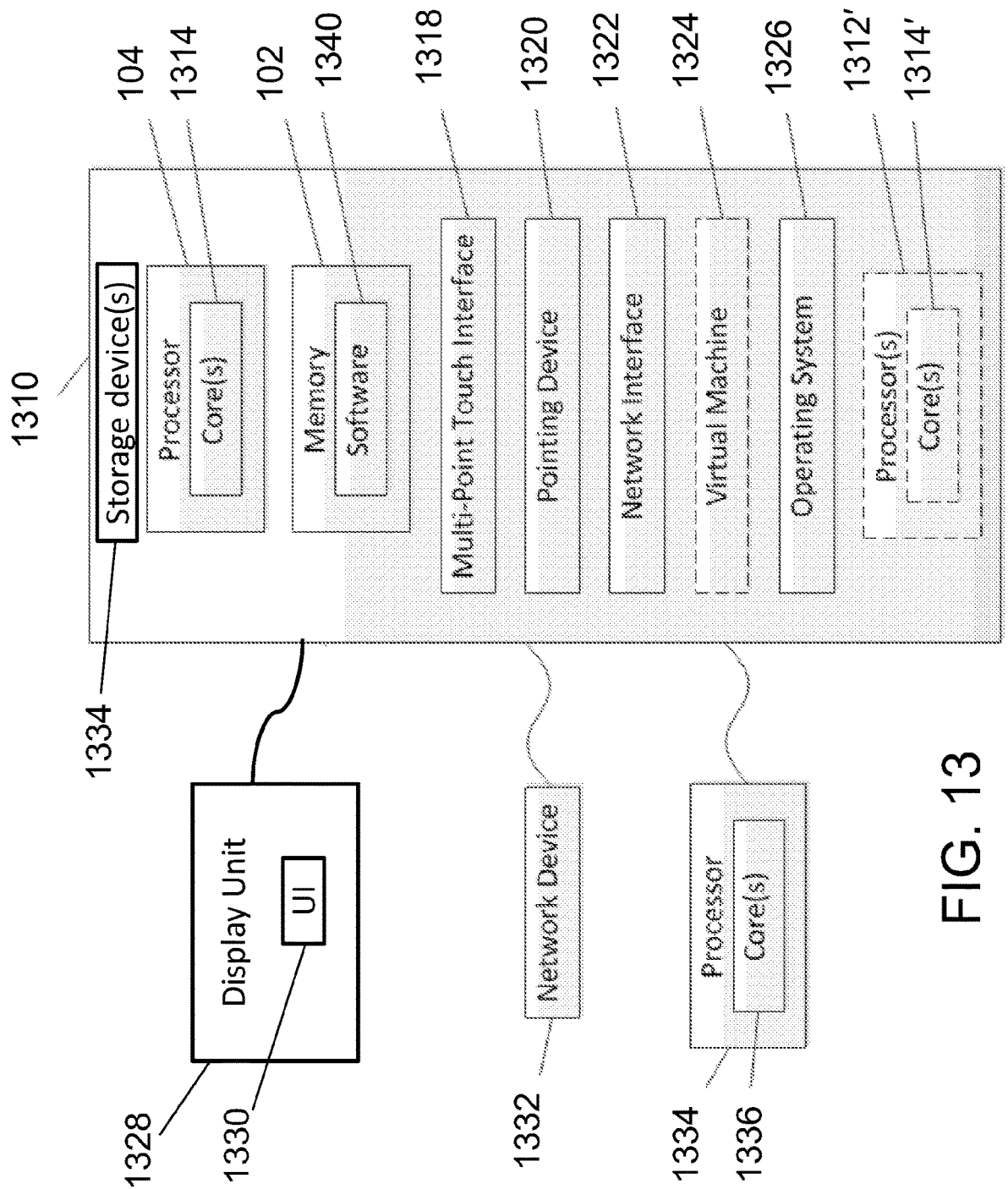
FIG. 13 shows a block diagram of an example computer system, according to the principles herein.

FIG. 13 is a block diagram of an example computing device 1310 that can be used as a computing component according to the principles herein. In any example herein, computing device 1310 can be configured as a console that receives user input to implement the computing component, including to compute a performance metric (including an indicator), apply a first predictive model to generate a scoring output, and/or apply any other predictive model described herein. For clarity, FIG. 13 also refers back to and provides greater detail regarding various elements of the example system of FIG. 1. The computing device 1310 can include one or more non-transitory computer-readable media for storing one or more computer-executable instructions or software for implementing examples. The non-transitory computer-readable media can include, but are not limited to, one or more types of hardware memory, non-transitory tangible media (for example, one or more magnetic storage disks, one or more optical disks, one or more flash drives), and the like. For example, memory 102 included in the computing device 1310 can store computer-readable and computer-executable instructions or software for performing the operations disclosed herein. For example, the memory 102 can store a software application 1340 which is configured to perform various of the disclosed operations (e.g., analyze cognitive platform measurement data and response data, compute a performance metric (including an indicator), apply a first predictive model to generate a scoring output, and/or apply any other predictive model described herein. The computing device 1310 also includes configurable and/or programmable processor 104 and an associated core 1314, and optionally, one or more additional configurable and/or programmable processing devices, e.g., processor(s) 1312' and associated core(s) 1314' (for example, in the case of computational devices having multiple processors/cores), for executing computer-readable and computer-executable instructions or software stored in the memory 102 and other programs for controlling system hardware. Processor 104 and processor(s) 1312' can each be a single core processor or multiple core (1314 and 1314') processor.

Virtualization can be employed in the computing device 1310 so that infrastructure and resources in the console can be shared dynamically. A virtual machine 1324 can be provided to handle a process executing on multiple processors so that the process appears to be using only one computing resource rather than multiple computing resources. Multiple virtual machines can also be used with one processor.

Memory 102 can include a computational device memory or random access memory, such as but not limited to DRAM, SRAM, EDO RAM, and the like. Memory 102 can include a non-volatile memory, such as but not limited to a hard-disk or flash memory. Memory 102 can include other types of memory as well, or combinations thereof.

In a non-limiting example, the memory 102 and at least one processing unit 104 can be components of a peripheral device, such as but not limited to a dongle (including an adapter) or other peripheral hardware. The example peripheral device can be programmed to communicate with or otherwise couple to a primary computing device, to provide the functionality of any of the example cognitive platform and/or platform product, and implement any of the example analyses (including the associated computations) described herein. In some examples, the peripheral device can be programmed to directly communicate with or otherwise couple to the primary computing device (such as but not limited to via a USB or HDMI input), or indirectly via a cable (including a coaxial cable), copper wire (including, but not limited to, PSTN, ISDN, and DSL), optical fiber, or other connector or adapter. In another example, the peripheral device can be programmed to communicate wirelessly (such as but not limited to Wi-Fi or Bluetooth®) with the primary computing device. The example primary computing device can be a smartphone (such as but not limited to an iPhone®, a BlackBerry®, or an Android™-based smartphone), a television, a workstation, a desktop computer, a laptop, a tablet, a slate computer, an electronic-reader (e-reader), a digital assistant, or other electronic reader or hand-held, portable, or wearable computing device, or any other equivalent device, an Xbox®, a Wii®, or other equivalent form of computing device.

A user can interact with the computing device 1310 through a visual display unit 1328, such as a computer monitor, which can display one or more user interfaces 1330 that can be provided in accordance with example systems and methods. While the example of FIG. 13 shows a visual display unit 1328 as a component in communication with the computing device 1310, the visual display 1328 may be configured as a display that is an integral portion of the computing device 1310 (such as but not limited to a touch screen or other contact or pressure sensitive screen). The computing device 1310 can include other input/output (I/O) devices for receiving input from a user, for example, a keyboard or any suitable multi-point touch interface 1318, a pointing device 1320 (e.g., a mouse), a camera or other image recording device, a microphone or other sound recording device, an accelerometer, a gyroscope, a sensor for tactile, vibrational, or auditory signal, and/or at least one actuator. The keyboard 1318 and the pointing device 1320 can be coupled to the visual display unit 1328. The computing device 1310 can include other suitable conventional I/O peripherals.

The computing device 1310 can also include one or more storage devices 1334, such as a hard-drive, CD-ROM, or other computer readable media, for storing data and computer-readable instructions and/or software that perform operations disclosed herein. Example storage device 1334 can also store one or more databases for storing any suitable information required to implement example systems and methods. The databases can be updated manually or automatically at any suitable time to add, delete, and/or update one or more items in the databases.

The computing device 1310 can include a network interface 1322 configured to interface via one or more network devices 1332 with one or more networks, for example, Local Area Network (LAN), metropolitan area network (MAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 1322 can include a built-in network adapter, network interface card, PCMCIA network card, card bus network adapter, wireless network adapter, USB network adapter, modem or any other device suitable for interfacing the computing device 1310 to any type of network capable of communication and performing the operations described herein. Moreover, the computing device 1310 can be any computational device, such as a smartphone (such as but not limited to an iPhone®, a BlackBerry®, or an Android™-based smartphone), a television, a workstation, a desktop computer, a server, a laptop, a tablet, a slate computer, an electronic-reader (e-reader), a digital assistant, or other electronic reader or hand-held, portable, or wearable computing device, or any other equivalent device, an Xbox®, a Wii®, or other equivalent form of computing or telecommunications device that is capable of communication and that has or can be coupled to sufficient processor power and memory capacity to perform the operations described herein. The one or more network devices 1332 may communicate using different types of protocols, such as but not limited to WAP (Wireless Application Protocol), TCP/IP (Transmission Control Protocol/Internet Protocol), NetBEUI (NetBIOS Extended User Interface), or IPX/SPX (Internetwork Packet Exchange/Sequenced Packet Exchange).

The computing device 1310 can execute any operating system 1326, such as any of the versions of the Microsoft® Windows® operating systems, iOS® operating system, Android™ operating system, the different releases of the Unix and Linux operating systems, any version of the MacOS® for Macintosh computers, any embedded operating system, any real-time operating system, any open source operating system, any proprietary operating system, or any other operating system capable of executing on the console and performing the operations described herein. In some examples, the operating system 1326 can be executed in native mode or emulated mode. In an example, the operating system 1326 can be executed on one or more cloud machine instances.

Examples of the systems, methods and operations described herein can be implemented in digital electronic circuitry, or in computer software, firmware, or hardware, including the structures disclosed in this specification and their structural equivalents, or in combinations of one or more thereof. Examples of the systems, methods and operations described herein can be implemented as one or more computer programs, i.e., one or more modules of computer program instructions, encoded on computer storage medium for execution by, or to control the operation of, data processing apparatus. The program instructions can be encoded on an artificially generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" or "computing device" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, software, software application, script, application or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing on one or more computer programs to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), for example. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, for displaying information to the user and a keyboard and a pointing device, e.g., a mouse, a stylus, touch screen or a trackball, by which the user can provide input to the computer. Other kinds of devices can be used to provide for interaction with a user as well. For example, feedback (i.e., output) provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

In some examples, a system, method or operation herein can be implemented in a computing system that includes a back end component, e.g., as a data server, or that includes a middleware component, e.g., an application server, or that includes a front end component, e.g., a client computer having a user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Example computing system herein can include clients and servers. A client and server are generally remote from each other and typically interact through a communication network. The relationship of client and server arises by virtue of computer programs executing on the respective computers and having a client-server relationship to each other. In some embodiments, a server transmits data to a client device (e.g., for purposes of displaying data to and receiving user input from a user interacting with the client device). Data generated at the client device (e.g., a result of the user interaction) can be received from the client device at the server.

CONCLUSION

The above-described embodiments can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

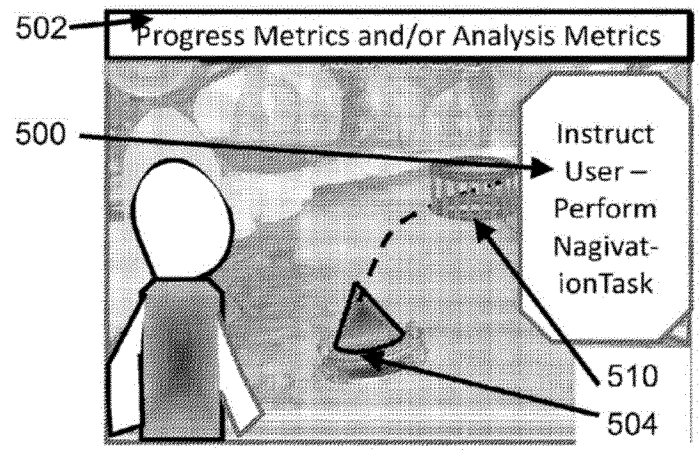

What is claimed is:

1. A computer-implemented method for enhancing one or more cognitive skills in an individual to provide an indication of a neurodegenerative condition of the individual, said method being implemented using a computing device comprising a processing unit, a graphical user interface, and an input device, said method comprising:

using the processing unit, executing a first trial at a first time interval, the first trial comprising:
rendering a first instance of a primary task at the graphical user interface, the first instance of the primary task requiring a first primary response from the individual to the first instance of the primary task using the input device,
wherein the primary task comprises one or more computerized stimuli or interactions comprising one or more interactive elements rendered at the graphical user interface,
wherein the primary task comprises a time-varying task having a response deadline;
rendering a second instance of the primary task with a first interference at the graphical user interface, the second instance of the primary task requiring a second primary response from the individual, using the input device, wherein the first interference comprises one or more graphical elements presented at the graphical user interface at one or more time intervals during the primary task;
wherein the first interference is configured to divert the individual's attention from the second instance of the primary task and is rendered as an interruptor or a distraction,
wherein the individual is instructed not to respond to the first interference that is configured as a distraction and to respond to the first interference that is configured as an interruptor;
using the processing unit, executing a second trial at a second time interval that is subsequent to the first time interval, the second trial comprising:
rendering a third instance of the primary task at the graphical user interface, the third instance of the primary task requiring a third primary response from the individual to the third instance of the primary task using the input device;
rendering a fourth instance of the primary task with a second interference at the graphical user interface, the fourth instance of the primary task requiring a fourth primary response from the individual using the input device, wherein the second interference comprises the one or more graphical elements presented at the graphical user interface at the one or more time intervals during the primary task,
wherein the processing unit is configured to adjust a difficulty level of the second interference in real-time in response to receiving one or more inputs from the individual via the input device, wherein adjusting the difficulty level comprises modifying one or more of a number, speed and size of the one or more graphical elements presented at the graphical user interface in real-time;
wherein the second interference is configured to divert the individual's attention from the fourth instance of the primary task and is rendered as the interruptor or the distraction,
wherein the individual is instructed not to respond to the second interference that is configured as the distraction and to respond to the second interference that is configured as the interruptor;
receiving, with the processing unit via the input device, data indicative of the first primary response, the second primary response, the third primary response, and the fourth primary response;
using the processing unit, analyzing one or more differences in the individual's performance from performing the primary task without interference and with interference at least in part by determining differences between the data indicative of the first primary response, the second primary response, the third primary response, and the fourth primary response, to determine at least one first indicator of the cognitive ability of the individual; and
using the processing unit, generating a scoring output indicative of a likelihood of onset of a neurodegenerative condition of the individual and/or a stage of progression of the neurodegenerative condition based at least in part on applying a first predictive model to the at least one first indicator,
wherein the scoring output comprises a classification output of the first predictive model,
wherein the first predictive model is configured to classify the individual as having an amyloid positive status or an amyloid negative status based on the data indicative of the first primary response, the second primary response, the third primary response, and the fourth primary response.

2. The method of claim 1, further comprising training, using the processing unit, the first predictive model using a plurality of training datasets, wherein each training dataset in the plurality of training datasets corresponds to a previously classified individual in a plurality of individuals, wherein each training dataset comprises data representing the at least one first indicator of the cognitive ability of the classified individual and data indicative of a diagnosis of a status or progression of the neurodegenerative condition in the classified individual.

3. The method of claim 1, wherein the processing unit is further configured to execute instructions and perform: applying at least one adaptive procedure to modify the primary task and/or the first interference, such that analysis of the data indicative of the third primary response and/or the fourth primary response indicates a modification of the at least one first indicator.

4. The method of claim 1, wherein the processing unit is configured to render the first instance of the primary task as a continuous visuo-motor tracking task, and wherein the first instance of the primary task and the second instance of the primary task are a first time interval of the continuous visuo-motor task.

5. The method of claim 1, wherein the processing unit is configured to render the first interference and second interference as a target discrimination interference.

6. The method of claim 1, wherein the processing unit is configured to:
   receive a secondary response to the first interference at the same time as the processing unit receives the second primary response; or
   (ii) receive the secondary response to the first interference that is an interruptor at the same time as the processing unit receives the first primary response and not receive the secondary response to the first interference that is a distraction at the same time that the processing unit receives the first primary response.

7. The method of claim 1, further comprising adjusting a difficulty of one or both of the primary task or the first interference such that the computing device renders at a second difficulty level one or more of: the third instance of the primary task, the fourth instance of the primary task, or the second interference.

8. The method of claim 1, further comprising using the computing device, executing a third trial at a third time interval that is subsequent to the second time interval, the third trial comprising:
   rendering a fifth instance of the primary task, requiring a fifth primary response from the individual to the fifth instance of the primary task using the input device;
   render a sixth instance of the primary task with a third interference, requiring a sixth primary response from the individual using the input device, to the sixth instance of the primary task in the presence of the third interference;
   wherein the third interference is configured to divert the individual's attention from the sixth instance of the primary task and is rendered as the interruptor or the distraction; and
   wherein the individual is instructed not to respond to the third interference that is configured as the distraction and to respond to the third interference that is configured as the interruptor;
   receive data indicative of the fifth primary response and the sixth primary response;
   using the computing device, analyze the differences in the individual's performance from performing the primary task without interference and with interference at least in part by determining differences between the data indicative of the first primary response, the second primary response, the third primary response, the fourth primary response, the fifth primary response, and the sixth primary response, to determine at least one second indicator of the cognitive ability of the individual; and
   using the computing device, generate the scoring output indicative of the likelihood of onset of the neurodegenerative condition of the individual and/or the stage of progression of the neurodegenerative condition, based at least in part on applying the first predictive model to the at least one second indicator.

9. The method of claim 8, further comprising adjusting a difficulty of one or both of the primary task or the second interference such that the computing device renders at a second difficulty level one or more of: the fifth instance of the primary task, the sixth instance of the primary task, or the third interference.

* * * * *

UNITED STATES PATENT AND TRADEMARK OFFICE
CERTIFICATE OF CORRECTION

PATENT NO. : 11,690,560 B2
APPLICATION NO. : 16/344074
DATED : July 4, 2023
INVENTOR(S) : Jeffrey Bower and Titiimaea Alailima It is certified that error appears in the above-identified patent and that said Letters Patent is hereby corrected as shown below:

On the Title Page

Delete the title page and substitute therefore with the attached title page showing the corrected number of claims.

In the Claims

Column 86, Line 37, insert the following claims:

--10. The method of claim 1 wherein the neurodegenerative condition is selected from the group consisting of Alzheimer's disease, dementia, Parkinson's disease, cerebral amyloid angiopathy, familial amyloid neuropathy, or Huntington's disease.

11. The method of claim 1, wherein the processing unit is configured to control one or more sensor components configured to measure the data indicative of one or more of the first primary response, the second primary response, the third primary response, or the fourth primary response.

12. The method of claim 11 wherein the one or more sensor components comprises one or more of a gyroscope, an accelerometer, a motion sensor, a position sensor, a pressure sensor, an optical sensor, a video camera, an auditory sensor, and a vibrational sensor.

13. The method of claim 1 wherein the primary task comprises a visuo-motor navigation task.

14. The method of claim 13 wherein the first primary response from the individual to the first instance of the primary task comprises at least one navigation response from the individual via the input device.

15. The method of claim 14 wherein the at least one navigation response comprises guiding an interactive element in the one or more interactive elements to coincide with a target object at the graphical user interface and avoid a non-target object at the graphical user interface.

Signed and Sealed this
Fourth Day of March, 2025

Coke Morgan Stewart
*Acting Director of the United States Patent and Trademark Office*

16. The method of claim 11 further comprising selectively activating or deactivating, with the processing unit, the one or more sensor components based on the presentation of the first interference or the second interference.

17. The method of claim 1 wherein the processing unit is configured to modify a temporal length of the response deadline for the time-varying task.

18. The method of claim 1 further comprising receiving, with at least one physiological component, at least one physiological data input for the individual.

19. The method of claim 18 wherein the at least one physiological data input for the individual is received concurrently with receiving the data indicative of the first primary response, the second primary response, the third primary response, and the fourth primary response.

20. The method of claim 1 wherein the first predictive model is further configured to classify the individual as to a level of expression of one or more of a cystatin, an alpha-synuclein, a huntingtin protein, a tau protein, or an apolipoprotein E based on the data indicative of the first primary response, the second primary response, the third primary response, and the fourth primary response.--.

CERTIFICATE OF CORRECTION (continued)

(12) United States Patent
Bower et al.

(10) Patent No.: US 11,690,560 B2
(45) Date of Patent: Jul. 4, 2023

(54) COGNITIVE PLATFORM CONFIGURED AS A BIOMARKER OR OTHER TYPE OF MARKER

(71) Applicant: Akili Interactive Labs, Inc., Boston, MA (US)

(72) Inventors: Jeffrey Bower, Norwood, MA (US); Titiimaea Alailima, Cambridge, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 856 days.

(21) Appl. No.: 16/344,074

(22) PCT Filed: Oct. 24, 2017

(86) PCT No.: PCT/US2017/058103
§ 371 (c)(1),
(2) Date: Apr. 23, 2019

(87) PCT Pub. No.: WO2018/081134
PCT Pub. Date: May 3, 2018

(65) Prior Publication Data
US 2020/0060603 A1   Feb. 27, 2020

Related U.S. Application Data

(60) Provisional application No. 62/412,215, filed on Oct. 24, 2016.

(51) Int. Cl.
*A61B 5/00* (2006.01)
*G16H 50/50* (2018.01)
(Continued)

(52) U.S. Cl.
CPC .......... *A61B 5/4088* (2013.01); *A61B 5/0024* (2013.01); *A61B 5/0075* (2013.01);
(Continued)

(58) Field of Classification Search
CPC ....... A61B 5/4088; A61B 5/246; A61B 5/377; A61B 5/0024; A61B 5/0075;
(Continued)

(56) References Cited

U.S. PATENT DOCUMENTS

2004/0175683 A1   9/2004   Duffy et al.
2008/0280276 A1   11/2008  Raber et al.
(Continued)

FOREIGN PATENT DOCUMENTS

JP   2005-137629 A   6/2005
JP   2011-083403 A   4/2011
(Continued)

OTHER PUBLICATIONS

International Search Report, International application No. PCT/US2017/058103, dated Dec. 28, 2017. ISA/US, Alexandria, VA.
(Continued)

*Primary Examiner* — Daniel L Cerioni
(74) *Attorney, Agent, or Firm* — Gregory Finch; Finch Paolino, LLC

(57) ABSTRACT

Example systems, methods, and apparatus are provided for using data collected from the responses of an individual with the computerized tasks of a cognitive platform to derive performance metrics as an indicator of cognitive abilities, and applying predictive models to generate an indication of neurodegenerative condition. The example systems, methods, and apparatus also can be configured to adapt the computerized tasks to enhance the individual's cognitive abilities, and for using data collected from the responses of an individual with the adapted computerized tasks to derive performance metrics and applying predictive models to generate the indication of neurodegenerative condition.

20 Claims, 22 Drawing Sheets